(12) United States Patent
Conaty et al.

(10) Patent No.: US 6,828,148 B2
(45) Date of Patent: Dec. 7, 2004

(54) MINIRIBOZYMES ACTIVE AT LOW MAGNESIUM ION CONCENTRATIONS

(75) Inventors: Jason Francis Conaty, Birchgrove (AU); Philip Hendry, Leichhardt (AU); Trevor John Lockett, Denistone (AU)

(73) Assignee: Gene Shears Pty. Limited, Canberra (AU)

( * ) Notice: Subject to any disclaimer, the term of this patent is extended or adjusted under 35 U.S.C. 154(b) by 15 days.

(21) Appl. No.: 09/887,880

(22) Filed: Jun. 22, 2001

(65) Prior Publication Data

US 2002/0155454 A1 Oct. 24, 2002

Related U.S. Application Data

(63) Continuation of application No. PCT/AU99/01162, filed on Dec. 24, 1999.

(30) Foreign Application Priority Data

Dec. 24, 1998 (AU) .............................................. 7951/98

(51) Int. Cl.[7] .......................... C12N 5/00; C12N 5/02; C12N 15/00; C07H 21/04; A61K 31/70
(52) U.S. Cl. ........................ 435/375; 435/6; 435/91.31; 435/320.1; 435/325; 514/44; 536/23.2; 536/24.5
(58) Field of Search ..................... 436/6, 91.31, 320.1, 436/325, 375, 93.1; 536/23.1, 23.2, 24.5; 514/44

(56) References Cited

FOREIGN PATENT DOCUMENTS

| WO | WO9413688 | 6/1994 | |
|---|---|---|---|
| WO | WO9531541 | 11/1995 | |
| WO | WO9640906 | 12/1996 | |
| WO | WO9715662 | 5/1997 | |
| WO | WO 9832843 A2 * | 7/1998 | ........... C12N/15/00 |
| WO | WO9832843 | 7/1998 | |
| WO | WO 9833893 A2 * | 8/1998 | ........... C12N/9/00 |
| WO | WO9850530 | 11/1998 | |

OTHER PUBLICATIONS

Branch A good antisense molecule is hard to find. TIBS, Feb. 1998, vol. 23, pp. 45–50.*
Jen et al. Suppression of Gene Expression by Targeted Disruption of Messenger RNA: Available Options and Current Stategie (2000) Stem Cells. vol. 18, pp. 307–319.*
Crooke, S. T. Antisense Research and Application, Chapter 1, Basic Principles of Antisense Therapeutics, (1998) pp. 1–50. Springer–Verlag Press, Berlin, Heidelberg, New York.*
Biochemical and Biophysical Research Communications (1998), 250(3), 711–719.*
Hertel et al. "Numbering system for the hammerhead" 1992 Nucleic Acid Res. 20 3252 (Exhibit B).
Conaty, J., Hendry, P., and Lockett, T., "Selected classes of minimised hammerhead ribozyme have very high cleavage rates at low $Mg^{2+}$ concetration", *Nucleic Acids Research* 1999; 27: (11) 2400–2407; (Exhibit 7).
Goodchild, J. and Kohli, V., "Ribozymes That Cleave an RNA Sequence from Human Immunodeficiency Virus: The Effect of Flanking Sequence on Rate[1]", *Archives of Ribochemistry and Biophysics* 1991; 284: (2) 386–391; (Exhibit 8).
Long, D.M. and Uhlenbeck, Olke C., "Kinetic Characterization of intramolecular and intermolecular hammerhead RNAs with stem II deletions", *Proc. Natl. Acad. Sci. USA* 1994; 9: 6977–6981. (Exhibit 9).
International Search Report, Feb. 23, 2001 (Exhibit 10).

* cited by examiner

*Primary Examiner*—Janet L. Epps-Ford
(74) *Attorney, Agent, or Firm*—John P. White; Cooper & Dunham LLP

(57) ABSTRACT

This invention is directed to a class of miniribozymes, capable of hybridizing with a target RNA to be cleaved and exhibiting very high cleavage rates at low $Mg^{2+}$ concentration. The miniribozymes may be used in vitro or in vivo. They may be used as diagnostic or therapeutic agents.

30 Claims, 11 Drawing Sheets

Figure 2
a
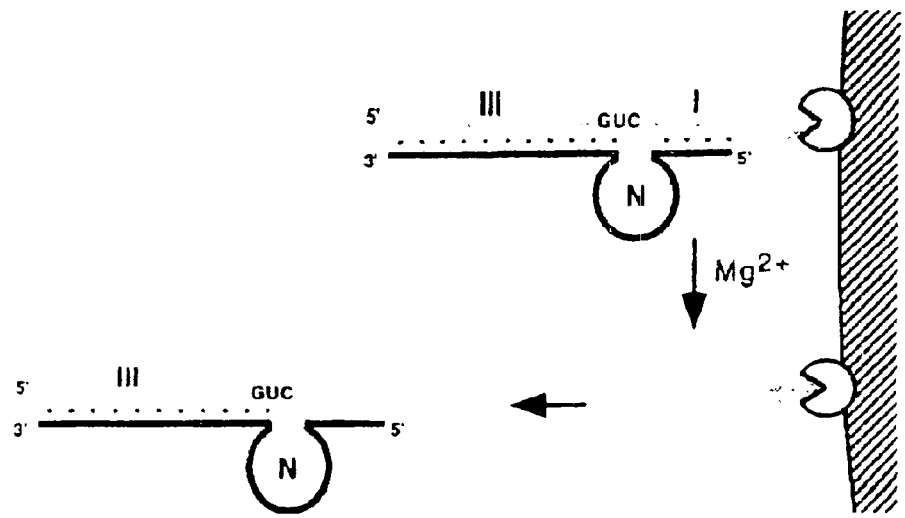
b
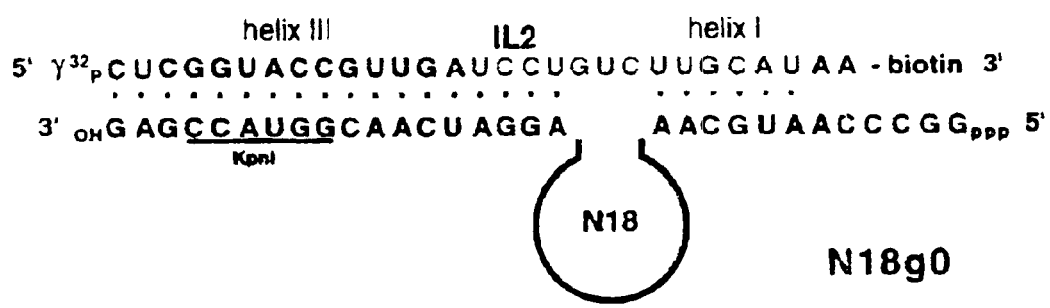
c
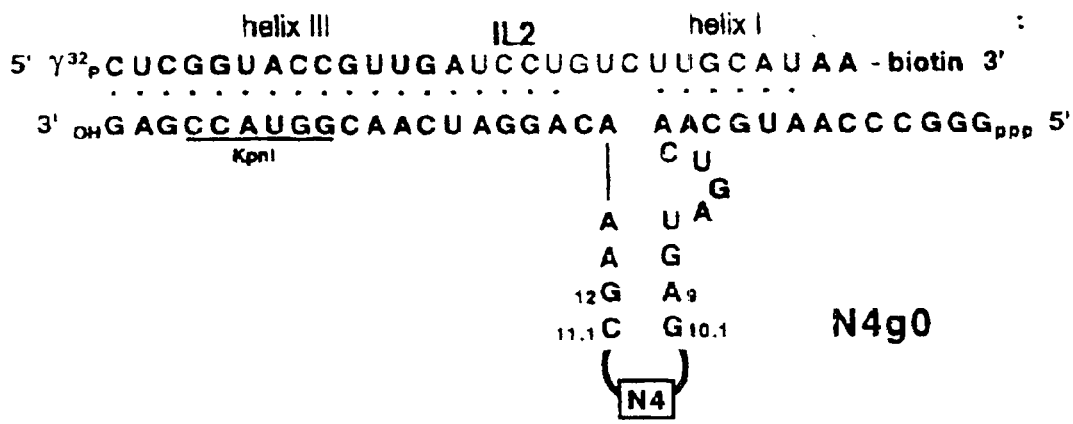

|  |  |
|---|---|
| 4.1 | CUGAUGAUAUAUAGAAAC- |
| 4.3 | CUGACGAACUCAUGAAAC- |
| 4.4 | CUGAUGAUAAACUGAAAC- |
| 4.5 | CUGAUGAACUUCUGAAAC- |
| 4.7 | CUGACGAUGAAACGAAAC- |
| 4.9 | CUGACGACAACGUGAAAC- |
| 4.10 | CUGAUGACGCACUGAAAC- |
| 4.12 | CUGAUGAAGCAGUGAAAC- |
| 4.13 | CUGAUGAGUAU-UGAAAC- |
| 4.14 | CUGAUGAGAAU-CGAAAC- |
| 4.15 | CUGACGACCAAGAGAAAC- |
| 4.19 | CUGAUGACACAUCGAAAC- |
| 4.21 | CUGAUGAUCCACUGAAAC- |
| 4.23 | CUGAGGAGGAGUCGAAAC- |
| 4.26 | CUGAUGAUGCCUUGAAAC- |
| 4.27 | CUGAAGAGAAUCUGAAAC- |
| 4.28 | CUGAUGACAUGCCGAAAC- |
| 4.29 | CUGAUGAUACCUUGAAAC- |
| 4.30 | CUGAUGAGUUAUUGAAAC- |
| 4.31 | CUGAUGAUUAU-UGAAACU |
| 4.32 | CUGACGAACAAAUGAAAC- |
| 4.34 | CUGAUGACAUUAAGAAAC- |
| 4.35 | CUGAAGAAUAAAAGAAAC- |
| 4.36 | CUGAUGAAACCCUGAAAC- |
| 4.37 | CUGAAGAAAGCCUGAAAC- |
| 4.38 | CUGAUGAUGACUGGAAAC- |
| 4.39 | CUGACGAUUCUACGAAAC- |
| 4.40 | CUGACGAAGUAUUGAAAC- |
| 4.43 | CUGAUGAACUAGGGAAAC- |
| 4.45 | CUGAUGAUUGUUAGAAAC- |
| 4.46 | CUGAUGAUUAGGCGAAAC- |

N18 g4

L.1 L.2 L.3 L.4
10.1    11.1 b

5'-3'

|  |  |
|---|---|
| 6.1 | CUGACGACGCCCCGAAAC |
| 6.2 | CUGAAGAGACCACGAAAC |
| 6.3 | CUGAUGAAGAAAUGAAAC |
| 6.4 | CUGACGAAUUUUGGAAAC |
| 6.5 | CUGAUGAGGGACGAAAC |
| 6.6 | CUGAUGAUUUGGUGAAAC |
| 6.7 | CUGAUGAGCUAACGAAAC |
| 6.8 | CUGAUGAAACGCCGAAAC |
| 6b9 | CUGAUGAAUAU-UGAAAC |
| 6b10 | CUGAUGAAACCAUGAAAC |
| 6b11 | CUGAUGAAUCUGUGAAAC | g6b

|  |  |
|---|---|
| 6.9 | CUGAUGAUAUUUGAAAC |
| 6.10 | CUGAUGAGGGACGAAAC |
| 6.11 | CUGAUGAGCAAACGAAAC |
| 6.12 | CUGACGACUUGGAGAAAC |
| 6.13 | CUGAUGAUAUUAUGAAAC |
| 6.14 | CUGACGAGUCUACGAAAC |
| 6.15 | CUGAUGAGGCAACGAAAC |
| 6.16 | CUGAUGAGGCAACGAAAC |
| 6c9 | CUGAUGAGUCCCCGAAAC |
| 6c10 | CUGACGAGGUAACGAAAC |
| 6c11 | CUGAUGACGCCAGGAAAC |
| 6c12 | CUGAAGAGCAACCGAAAC |
| CS1 | CUGAAGAGCUACCGAAAC |
| CS2 | CUGAUGAGUGACCGAAAC |
| CS3 | CUGACGAGUUUACGAAAC |
| CS4 | CUGAAGAGUUUACGAAAC |
| CS5 | CUGAAGAGUAAUCGAAAC |
| CS6 | CUGAAGAGUAACCGAAAC | g6c

|  |  |
|---|---|
| 6.17 | CUGAUGAGUCCACGAAAC |
| 6.18 | CUGAUGAGCACCCGAAAC |
| 6.19 | CUGAUGAGCUAACGAAAC |
| 6.20 | CUGACGAGCUCCCGAAAC |
| 6.21 | CUGAUGAGUUUUCGAAAC |
| 6.22 | CUGAUGAGCAUACGAAAC |
| 6.23 | CUGAGGAGAAACGAAAC |
| 6.24 | CUGACGAGUUAACGAAAC |
| 6d10 | CUGACGAUGGUAUGAAAC |
| D11 | CUGAUGAGCUACCGAAAC |
| D12 | CUGAAGAGUUACCGAAAC |
| D13 | CUGAUGAGCUAACGAAAC |
| D14 | CUGAUGAGCAAACGAAAC |
| D15 | CUGAAGAGCCAUCGAAAC |
| D16 | CUGAUGAGCGAACGAAAC |
| D17 | CUGAUGAGCUCACGAAAC |
| D18 | CUGAUGAGACCACGAAAC | g6d

Figure 6

NNHH class I — YRHH: CGUU, UGUU, UAAC class II — WYHH: ACCC 3, AUUU, UCCC, AUUC, AUUA class III — GHHA: GUAA 2, GAUA pyrimidine rich subclass (II)

UUHH: UUUU 3, UUAC 4, UUCC, UUUC 2, UUUA 2

Ribonuclease protection assay of PDGF mRNA

SEQUENCE LISTING

<160> NUMBER OF SEQ ID NOS: 153

<210> SEQ ID NO 1
<211> LENGTH: 15
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (8)..(9)
<223> OTHER INFORMATION: n = c, g, a, u/t
<220> FEATURE:
<221> NAME/KEY: misc_feature
<222> LOCATION: (10)..(11)
<223> OTHER INFORMATION: h = c, a, u/t

```
<400> SEQUENCE: 1
cugagagnnh hcgaa                                                15

<210> SEQ ID NO 2
<211> LENGTH: 16
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (9)..(9)
<223> OTHER INFORMATION: n = c, g, a, u/t
<220> FEATURE:
<221> NAME/KEY: misc_feature
<222> LOCATION: (8)..(8)
<223> OTHER INFORMATION: h = c,  a, u/t
<220> FEATURE:
<221> NAME/KEY: misc_feature
<222> LOCATION: (10)..(12)
<223> OTHER INFORMATION: h = c,  a, u/t

<400> SEQUENCE: 2
cugagaghnh hhcgaa                                               16

<210> SEQ ID NO 3
<211> LENGTH: 65
<212> TYPE: DNA
<213> ORGANISM: Artificial Sequence
<220> FEATURE:
<223> OTHER INFORMATION: N18gOT65mer (T3 promoter)
<220> FEATURE:
<221> NAME/KEY: misc_feature
<222> LOCATION: (19)..(36)
<223> OTHER INFORMATION: n = c, g, a, t

<400> SEQUENCE: 3
ctcggtaccg ttgatcctnn nnnnnnnnnn nnnnnnttgc attgggcctt tagtgagggt    60
taatt                                                               65

<210> SEQ ID NO 4
<211> LENGTH: 29
<212> TYPE: RNA
<213> ORGANISM: Artificial Sequence
<220> FEATURE:
<223> OTHER INFORMATION: IL2bioS29mer (cleavage substrate)

<400> SEQUENCE: 4
cucgguaccg uugauccugu cuugcauaa                                 29

<210> SEQ ID NO 5
<211> LENGTH: 66
<212> TYPE: DNA
<213> ORGANISM: Artificial Sequence
<220> FEATURE:
<223> OTHER INFORMATION: N4gOT66mer (T7 promoter)
<220> FEATURE:
<221> NAME/KEY: misc_feature
<222> LOCATION: (25)..(28)
<223> OTHER INFORMATION: n = c, g, a, t

<400> SEQUENCE: 5
ctcggtaccg ttgatcctgt ttcgnnnnct catcagttgc attgggccct atagtgattc    60
gtatta                                                              66

<210> SEQ ID NO 6
```

```
<211> LENGTH: 69
<212> TYPE: DNA
<213> ORGANISM: Artificial Sequence
<220> FEATURE:
<223> OTHER INFORMATION: N5gOT 67-mer (T7 promoter)
<220> FEATURE:
<221> NAME/KEY: misc_feature
<222> LOCATION: (27)..(31)
<223> OTHER INFORMATION: all n = c, g, a, t

<400> SEQUENCE: 6
mrctcggtac cgttgatcct gtttcgnnnn nctcatcagt tgcattgggc cctatagtga      60
gtcgtatta                                                              69

<210> SEQ ID NO 7
<211> LENGTH: 15
<212> TYPE: DNA
<213> ORGANISM: Artificial Sequence
<220> FEATURE:
<223> OTHER INFORMATION: T3 15mer (T7 promoter)

<400> SEQUENCE: 7
aattaaccct cacta                                                       15

<210> SEQ ID NO 8
<211> LENGTH: 17
<212> TYPE: DNA
<213> ORGANISM: Artificial Sequence
<220> FEATURE:
<223> OTHER INFORMATION: P1 17mer (T7 promoter)

<400> SEQUENCE: 8
ctcggtaccg ttgatcc                                                     17

<210> SEQ ID NO 9
<211> LENGTH: 38
<212> TYPE: DNA
<213> ORGANISM: Artificial Sequence
<220> FEATURE:
<223> OTHER INFORMATION: P2 38mer (T7 promoter)

<400> SEQUENCE: 9
gagggatcct aatacgactc actataggcc caatgcaa                              38

<210> SEQ ID NO 10
<211> LENGTH: 40
<212> TYPE: DNA
<213> ORGANISM: Artificial Sequence
<220> FEATURE:
<223> OTHER INFORMATION: P3 40mer (T7 promoter)

<400> SEQUENCE: 10
gagggatcct aatacgactc actatagggc ccaatgcaac                            40

<210> SEQ ID NO 11
<211> LENGTH: 17
<212> TYPE: RNA
<213> ORGANISM: Artificial Sequence
<220> FEATURE:
<223> OTHER INFORMATION: KrS17 (17mer substrate)

<400> SEQUENCE: 11
uugcgagucc acacugg                                                     17

<210> SEQ ID NO 12
<211> LENGTH: 19
```

```
<212> TYPE: RNA
<213> ORGANISM: Artificial Sequence
<220> FEATURE:
<223> OTHER INFORMATION: IL2S19 (19mer substrate)

<400> SEQUENCE: 12
aacuccuguc uugcauugc                                                        19

<210> SEQ ID NO 13
<211> LENGTH: 15
<212> TYPE: RNA
<213> ORGANISM: Artificial Sequence
<220> FEATURE:
<223> OTHER INFORMATION: IL2S15 (15mer substrate)

<400> SEQUENCE: 13
uccugucuug cauug                                                            15

<210> SEQ ID NO 14
<211> LENGTH: 34
<212> TYPE: RNA
<213> ORGANISM: Artificial Sequence
<220> FEATURE:
<223> OTHER INFORMATION: KrMc10 (34mer miniribozyme)

<400> SEQUENCE: 14
uccagugugc ugaugaggua acgaaacucg caaa                                       34

<210> SEQ ID NO 15
<211> LENGTH: 42
<212> TYPE: DNA
<213> ORGANISM: Artificial Sequence
<220> FEATURE:
<223> OTHER INFORMATION: KrRz (42mer ribozyme)

<400> SEQUENCE: 15
cuccagugug cugaugaguc cuuuggacg aaacucgcaa at                               42

<210> SEQ ID NO 16
<211> LENGTH: 34
<212> TYPE: DNA
<213> ORGANISM: Artificial Sequence
<220> FEATURE:
<223> OTHER INFORMATION: IL2Mc10 (34mer miniribozyme)

<400> SEQUENCE: 16
gcaaugcaac ugaugaggua acgaaacagg agut                                       34

<210> SEQ ID NO 17
<211> LENGTH: 40
<212> TYPE: DNA
<213> ORGANISM: Artificial Sequence
<220> FEATURE:
<223> OTHER INFORMATION: IL2Rz (40mer ribozyme)

<400> SEQUENCE: 17
gcaaugcaac ugaugagucc uuuggacga aacaggagut                                  40

<210> SEQ ID NO 18
<211> LENGTH: 36
<212> TYPE: DNA
<213> ORGANISM: Artificial Sequence
<220> FEATURE:
<223> OTHER INFORMATION: PDGF293 MR1 (36-mer miniribozyme)

<400> SEQUENCE: 18
```
cagcuuccuc cugaugaggu aacgaaaugc uucuct				36

<210> SEQ ID NO 19
<211> LENGTH: 36
<212> TYPE: DNA
<213> ORGANISM: Artificial Sequence
<220> FEATURE:
<223> OTHER INFORMATION: PDGF293 MR2 (36-mer miniribozyme)

<400> SEQUENCE: 19
cagcuuccuc cugaugaggt aacgaaaugc uucuct				36

<210> SEQ ID NO 20
<211> LENGTH: 36
<212> TYPE: DNA
<213> ORGANISM: Artificial Sequence
<220> FEATURE:
<223> OTHER INFORMATION: PDGF293 MR3 (36-mer miniribozyme)

<400> SEQUENCE: 20
cagcttcctc cugaugaggt aacgaaaugc ttctct				36

<210> SEQ ID NO 21
<211> LENGTH: 36
<212> TYPE: DNA
<213> ORGANISM: Artificial Sequence
<220> FEATURE:
<223> OTHER INFORMATION: PDGF293 MR4 (36-mer miniribozyme)

<400> SEQUENCE: 21
cagcttcctc cugaugaggu aacgaaaugc uucuct				36

<210> SEQ ID NO 22
<211> LENGTH: 34
<212> TYPE: DNA
<213> ORGANISM: Artificial Sequence
<220> FEATURE:
<223> OTHER INFORMATION: PDGF293 MR5 (36-mer miniribozyme)
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (21)..(21)
<223> OTHER INFORMATION: fC= 2' fluorocytidine

<400> SEQUENCE: 22
cagcuuccuc cugaugagua cgaaaugcuu cuct				34

<210> SEQ ID NO 23
<211> LENGTH: 40
<212> TYPE: DNA
<213> ORGANISM: Artificial Sequence
<220> FEATURE:
<223> OTHER INFORMATION: PDGF293 MR6 (38-mer miniribozyme)
<220> FEATURE:
<221> NAME/KEY: modified_base
<222> LOCATION: (12)..(13)
<223> OTHER INFORMATION: ps=phosphorothioate linkage
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base

```
<222> LOCATION: (7)..(8)
<223> OTHER INFORMATION: cm
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (5)..(6)
<223> OTHER INFORMATION: um
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (31)..(32)
<223> OTHER INFORMATION: um
<220> FEATURE:
<221> NAME/KEY: modified_base
<222> LOCATION: (34)..(34)
<223> OTHER INFORMATION: um
<220> FEATURE:
<221> NAME/KEY: modified_base
<222> LOCATION: (36)..(37)
<223> OTHER INFORMATION: ps=phosphorothioate linkage
<220> FEATURE:
<221> NAME/KEY: modified_base
<222> LOCATION: (38)..(39)
<223> OTHER INFORMATION: ps=phosphorothioate linkage

<400> SEQUENCE: 23
cagcuuccuc cugaugaggt aacgaaaugc uucuctstst                40

<210> SEQ ID NO 24
<211> LENGTH: 28
<212> TYPE: DNA
<213> ORGANISM: Artificial Sequence
<220> FEATURE:
<223> OTHER INFORMATION: PDGF293 MR7 (28-mer miniribozyme)
<220> FEATURE:
<221> NAME/KEY: modified_base
<222> LOCATION: (1)..(2)
<223> OTHER INFORMATION: um
<220> FEATURE:
<221> NAME/KEY: modified_base
<222> LOCATION: (5)..(5)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (24)..(24)
<223> OTHER INFORMATION: um
<220> FEATURE:
```

```
<221> NAME/KEY: modified_base
<222> LOCATION: (28)..(28)
<223> OTHER INFORMATION: um
<220> FEATURE:
<221> NAME/KEY: modified_base
<222> LOCATION: (3)..(4)
<223> OTHER INFORMATION: cm
<220> FEATURE:
<221> NAME/KEY: modified_base
<222> LOCATION: (6)..(7)
<223> OTHER INFORMATION: cm
<220> FEATURE:
<221> NAME/KEY: modified_base
<222> LOCATION: (26)..(26)
<223> OTHER INFORMATION: cm
<220> FEATURE:
<221> NAME/KEY: modified_base
<222> LOCATION: (8)..(9)
<223> OTHER INFORMATION: ps = phosphorothioate linkage

<400> SEQUENCE: 24
uuccuccuga ugaggtaacg aaaugcut                                28

<210> SEQ ID NO 25
<211> LENGTH: 32
<212> TYPE: DNA
<213> ORGANISM: Artificial Sequence
<220> FEATURE:
<223> OTHER INFORMATION: PDGF293 MR8 (32-mer miniribozyme)
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (5)..(6)
<223> OTHER INFORMATION: cm
<220> FEATURE:
<221> NAME/KEY: modified_base
<222> LOCATION: (8)..(9)
<223> OTHER INFORMATION: cm
<220> FEATURE:
<221> NAME/KEY: modified_base
<222> LOCATION: (28)..(28)
<223> OTHER INFORMATION: cm
<220> FEATURE:
<221> NAME/KEY: modified_base
<222> LOCATION: (31)..(31)
<223> OTHER INFORMATION: cm
<220> FEATURE:
<221> NAME/KEY: modified_base
<222> LOCATION: (3)..(4)
<223> OTHER INFORMATION: um
<220> FEATURE:
<221> NAME/KEY: modified_base
<222> LOCATION: (7)..(7)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (26)..(26)
<223> OTHER INFORMATION: um
<220> FEATURE:
<221> NAME/KEY: modified_base
<222> LOCATION: (29)..(30)
<223> OTHER INFORMATION: um
<220> FEATURE:
<221> NAME/KEY: modified_base
<222> LOCATION: (10)..(11)
<223> OTHER INFORMATION: ps = phosphorothioate linkage

<400> SEQUENCE: 25
gcuuccuccu gaugaggtaa cgaaaugcuu ct                           32
```

```
<210> SEQ ID NO 26
<211> LENGTH: 36
<212> TYPE: DNA
<213> ORGANISM: Artificial Sequence
<220> FEATURE:
<223> OTHER INFORMATION: PDGF293 MR9 (36-mer miniribozyme)
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (7)..(8)
<223> OTHER INFORMATION: cm
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (5)..(6)
<223> OTHER INFORMATION: um
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (31)..(32)
<223> OTHER INFORMATION: um
<220> FEATURE:
<221> NAME/KEY: modified_base
<222> LOCATION: (34)..(34)
<223> OTHER INFORMATION: um
<220> FEATURE:
<221> NAME/KEY: modified_base
<222> LOCATION: (12)..(13)
<223> OTHER INFORMATION: ps = phosphorothioate linkage

<400> SEQUENCE: 26
cagcuuccuc cugaugaggt aacgaaaugc uucuct                     36

<210> SEQ ID NO 27
<211> LENGTH: 40
<212> TYPE: DNA
<213> ORGANISM: Artificial Sequence
<220> FEATURE:
<223> OTHER INFORMATION: PDGF293 MR10 (40-mer miniribozyme)
<220> FEATURE:
<221> NAME/KEY: modified_base
<222> LOCATION: (3)..(3)
```

```
<223> OTHER INFORMATION: cm
<220> FEATURE:
<221> NAME/KEY: modified_base
<222> LOCATION: (6)..(6)
<223> OTHER INFORMATION: cm
<220> FEATURE:
<221> NAME/KEY: modified_base
<222> LOCATION: (9)..(10)
<223> OTHER INFORMATION: cm
<220> FEATURE:
<221> NAME/KEY: modified_base
<222> LOCATION: (12)..(13)
<223> OTHER INFORMATION: cm
<220> FEATURE:
<221> NAME/KEY: modified_base
<222> LOCATION: (32)..(32)
<223> OTHER INFORMATION: cm
<220> FEATURE:
<221> NAME/KEY: modified_base
<222> LOCATION: (37)..(37)
<223> OTHER INFORMATION: cm
<220> FEATURE:
<221> NAME/KEY: modified_base
<222> LOCATION: (7)..(8)
<223> OTHER INFORMATION: um
<220> FEATURE:
<221> NAME/KEY: modified_base
<222> LOCATION: (11)..(11)
<223> OTHER INFORMATION: um
<220> FEATURE:
<221> NAME/KEY: modified_base
<222> LOCATION: (17)..(17)
<223> OTHER INFORMATION: um
<220> FEATURE:
<221> NAME/KEY: modified_base
<222> LOCATION: (30)..(30)
<223> OTHER INFORMATION: um
<220> FEATURE:
<221> NAME/KEY: modified_base
<222> LOCATION: (33)..(34)
<223> OTHER INFORMATION: um
<220> FEATURE:
<221> NAME/KEY: modified_base
<222> LOCATION: (36)..(36)
<223> OTHER INFORMATION: um
<220> FEATURE:
<221> NAME/KEY: modified_base
<222> LOCATION: (38)..(39)
<223> OTHER INFORMATION: um
<220> FEATURE:
<221> NAME/KEY: modified_base
<222> LOCATION: (14)..(15)
<223> OTHER INFORMATION: ps = phosphorothioate linkage

<400> SEQUENCE: 27
gacagcuucc uccugaugag gtaacgaaau gcuucucuuc                40

<210> SEQ ID NO 28
<211> LENGTH: 44
<212> TYPE: DNA
<213> ORGANISM: Artificial Sequence
<220> FEATURE:
<223> OTHER INFORMATION: PDGF293 MR11 (44-mer miniribozyme)
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (8)..(8)
<223> OTHER INFORMATION: cm
<220> FEATURE:
<221> NAME/KEY: modified_base
<222> LOCATION: (11)..(12)
<223> OTHER INFORMATION: cm
<220> FEATURE:
<221> NAME/KEY: modified_base
```

```
<222> LOCATION: (14)..(15)
<223> OTHER INFORMATION: cm
<220> FEATURE:
<221> NAME/KEY: modified_base
<222> LOCATION: (34)..(34)
<223> OTHER INFORMATION: cm
<220> FEATURE:
<221> NAME/KEY: modified_base
<222> LOCATION: (37)..(37)
<223> OTHER INFORMATION: cm
<220> FEATURE:
<221> NAME/KEY: modified_base
<222> LOCATION: (39)..(39)
<223> OTHER INFORMATION: cm
<220> FEATURE:
<221> NAME/KEY: modified_base
<222> LOCATION: (42)..(43)
<223> OTHER INFORMATION: cm
<220> FEATURE:
<221> NAME/KEY: modified_base
<222> LOCATION: (9)..(10)
<223> OTHER INFORMATION: um
<220> FEATURE:
<221> NAME/KEY: modified_base
<222> LOCATION: (13)..(13)
<223> OTHER INFORMATION: um
<220> FEATURE:
<221> NAME/KEY: modified_base
<222> LOCATION: (19)..(19)
<223> OTHER INFORMATION: um
<220> FEATURE:
<221> NAME/KEY: modified_base
<222> LOCATION: (32)..(32)
<223> OTHER INFORMATION: um
<220> FEATURE:
<221> NAME/KEY: modified_base
<222> LOCATION: (35)..(36)
<223> OTHER INFORMATION: um
<220> FEATURE:
<221> NAME/KEY: modified_base
<222> LOCATION: (38)..(38)
<223> OTHER INFORMATION: um
<220> FEATURE:
<221> NAME/KEY: modified_base
<222> LOCATION: (40)..(41)
<223> OTHER INFORMATION: um
<220> FEATURE:
<221> NAME/KEY: modified_base
<222> LOCATION: (16)..(17)
<223> OTHER INFORMATION: ps = phosphorothioate linkage

<400> SEQUENCE: 28
gggacagcuu ccuccugaug aggtaacgaa augcuucucu ucct                     44

<210> SEQ ID NO 29
<211> LENGTH: 36
<212> TYPE: DNA
<213> ORGANISM: Artificial Sequence
<220> FEATURE:
<223> OTHER INFORMATION: PDGF293 MR12 (36-mer miniribozyme)
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (7)..(8)
<223> OTHER INFORMATION: cm
<220> FEATURE:
<221> NAME/KEY: modified_base
<222> LOCATION: (10)..(11)
<223> OTHER INFORMATION: cm
<220> FEATURE:
```

```
<221> NAME/KEY: modified_base
<222> LOCATION: (23)..(23)
<223> OTHER INFORMATION: cm
<220> FEATURE:
<221> NAME/KEY: modified_base
<222> LOCATION: (30)..(30)
<223> OTHER INFORMATION: cm
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (5)..(6)
<223> OTHER INFORMATION: um
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (20)..(20)
<223> OTHER INFORMATION: um
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (31)..(32)
<223> OTHER INFORMATION: um
<220> FEATURE:
<221> NAME/KEY: modified_base
<222> LOCATION: (34)..(34)
<223> OTHER INFORMATION: um
<220> FEATURE:
<221> NAME/KEY: modified_base
<222> LOCATION: (12)..(13)
<223> OTHER INFORMATION: ps = phosphorothioate linkage

<400> SEQUENCE: 29
cagcuuccuc cugaugaggu aacgaaaugc uucuct                                 36

<210> SEQ ID NO 30
<211> LENGTH: 36
<212> TYPE: DNA
<213> ORGANISM: Artificial Sequence
<220> FEATURE:
<223> OTHER INFORMATION: PDGF293 MR13 (36-mer inactive miniribozyme)
<220> FEATURE:
<221> NAME/KEY: modified_base
<222> LOCATION: (1)..(1)
<223> OTHER INFORMATION: cm
<220> FEATURE:
<221> NAME/KEY: modified_base
<222> LOCATION: (4)..(4)
<223> OTHER INFORMATION: cm
<220> FEATURE:
<221> NAME/KEY: modified_base
<222> LOCATION: (7)..(8)
<223> OTHER INFORMATION: cm
<220> FEATURE:
<221> NAME/KEY: modified_base
<222> LOCATION: (10)..(11)
<223> OTHER INFORMATION: cm
<220> FEATURE:
<221> NAME/KEY: modified_base
<222> LOCATION: (30)..(30)
<223> OTHER INFORMATION: cm
```

```
<220> FEATURE:
<221> NAME/KEY: modified_base
<222> LOCATION: (33)..(33)
<223> OTHER INFORMATION: cm
<220> FEATURE:
<221> NAME/KEY: modified_base
<222> LOCATION: (35)..(35)
<223> OTHER INFORMATION: cm
<220> FEATURE:
<221> NAME/KEY: modified_base
<222> LOCATION: (5)..(6)
<223> OTHER INFORMATION: um
<220> FEATURE:
<221> NAME/KEY: modified_base
<222> LOCATION: (9)..(9)
<223> OTHER INFORMATION: um
<220> FEATURE:
<221> NAME/KEY: modified_base
<222> LOCATION: (15)..(15)
<223> OTHER INFORMATION: um
<220> FEATURE:
<221> NAME/KEY: modified_base
<222> LOCATION: (28)..(28)
<223> OTHER INFORMATION: um
<220> FEATURE:
<221> NAME/KEY: modified_base
<222> LOCATION: (31)..(32)
<223> OTHER INFORMATION: um
<220> FEATURE:
<221> NAME/KEY: modified_base
<222> LOCATION: (34)..(34)
<223> OTHER INFORMATION: um
<220> FEATURE:
<221> NAME/KEY: modified_base
<222> LOCATION: (12)..(13)
<223> OTHER INFORMATION: ps = phosphorothioate

<400> SEQUENCE: 30
cagcuuccuc cugaugaggt aacgagaugc uucuct                          36

<210> SEQ ID NO 31
<211> LENGTH: 25
<212> TYPE: RNA
<213> ORGANISM: Artificial Sequence
<220> FEATURE:
<223> OTHER INFORMATION: PDGF S25

<400> SEQUENCE: 31
aggaagagaa gcaucgagga agcug                                      25

<210> SEQ ID NO 32
<211> LENGTH: 19
<212> TYPE: DNA
<213> ORGANISM: Artificial Sequence
<220> FEATURE:
<223> OTHER INFORMATION: PDGF293 Antisense

<400> SEQUENCE: 32
agcttcctcg atgcttctc                                             19

<210> SEQ ID NO 33
<211> LENGTH: 18
<212> TYPE: DNA
<213> ORGANISM: Artificial Sequence
<220> FEATURE:
<223> OTHER INFORMATION: N4g5-1 clone

<400> SEQUENCE: 33
ctgatgagtt atcgaaac                                              18

<210> SEQ ID NO 34
```

```
<211> LENGTH: 18
<212> TYPE: DNA
<213> ORGANISM: Artificial Sequence
<220> FEATURE:
<223> OTHER INFORMATION: N4g5-2 clone

<400> SEQUENCE: 34
ctgatgaggt aacgaaac                                                 18

<210> SEQ ID NO 35
<211> LENGTH: 18
<212> TYPE: DNA
<213> ORGANISM: Artificial Sequence
<220> FEATURE:
<223> OTHER INFORMATION: N4g5-3 clone

<400> SEQUENCE: 35
ctgatgagac cccgaaac                                                 18

<210> SEQ ID NO 36
<211> LENGTH: 18
<212> TYPE: DNA
<213> ORGANISM: Artificial Sequence
<220> FEATURE:
<223> OTHER INFORMATION: N4g5-4 clone

<400> SEQUENCE: 36
ctgatgagat aacgaaac                                                 18

<210> SEQ ID NO 37
<211> LENGTH: 17
<212> TYPE: DNA
<213> ORGANISM: Artificial Sequence
<220> FEATURE:
<223> OTHER INFORMATION: N4g5-5 clone

<400> SEQUENCE: 37
ctgatgagac cccgaac                                                  17

<210> SEQ ID NO 38
<211> LENGTH: 18
<212> TYPE: DNA
<213> ORGANISM: Artificial Sequence
<220> FEATURE:
<223> OTHER INFORMATION: N4g5-7 clone

<400> SEQUENCE: 38
ctgatgagac cccgaaac                                                 18

<210> SEQ ID NO 39
<211> LENGTH: 18
<212> TYPE: DNA
<213> ORGANISM: Artificial Sequence
<220> FEATURE:
<223> OTHER INFORMATION: N4g5-9 clone

<400> SEQUENCE: 39
ctgatgagat accgaaac                                                 18

<210> SEQ ID NO 40
<211> LENGTH: 18
<212> TYPE: DNA
<213> ORGANISM: Artificial Sequence
<220> FEATURE:
<223> OTHER INFORMATION: N4g5-11 clone

<400> SEQUENCE: 40
```

```
ctgatgagat accgaaac                                               18

<210> SEQ ID NO 41
<211> LENGTH: 18
<212> TYPE: DNA
<213> ORGANISM: Artificial Sequence
<220> FEATURE:
<223> OTHER INFORMATION: N4g5-13 clone

<400> SEQUENCE: 41
ctgatgagtt tccgaaac                                               18

<210> SEQ ID NO 42
<211> LENGTH: 18
<212> TYPE: DNA
<213> ORGANISM: Artificial Sequence
<220> FEATURE:
<223> OTHER INFORMATION: N4g5-14 clone

<400> SEQUENCE: 42
ctgatgagtt ttcgaaac                                               18

<210> SEQ ID NO 43
<211> LENGTH: 18
<212> TYPE: DNA
<213> ORGANISM: Artificial Sequence
<220> FEATURE:
<223> OTHER INFORMATION: N4g5-15 clone

<400> SEQUENCE: 43
ctgatgagtt accgaaac                                               18

<210> SEQ ID NO 44
<211> LENGTH: 18
<212> TYPE: DNA
<213> ORGANISM: Artificial Sequence
<220> FEATURE:
<223> OTHER INFORMATION: N4g5-16 clone

<400> SEQUENCE: 44
ctgatgagac accgaaac                                               18

<210> SEQ ID NO 45
<211> LENGTH: 18
<212> TYPE: DNA
<213> ORGANISM: Artificial Sequence
<220> FEATURE:
<223> OTHER INFORMATION: N4g5-17 clone

<400> SEQUENCE: 45
ctgatgagtt aacgaaac                                               18

<210> SEQ ID NO 46
<211> LENGTH: 18
<212> TYPE: DNA
<213> ORGANISM: Artificial Sequence
<220> FEATURE:
<223> OTHER INFORMATION: N4g5-18 clone

<400> SEQUENCE: 46
ctgatgagtt accgaaac                                               18

<210> SEQ ID NO 47
<211> LENGTH: 18
<212> TYPE: DNA
```

```
<213> ORGANISM: Artificial Sequence
<220> FEATURE:
<223> OTHER INFORMATION: N4g5-19 clone

<400> SEQUENCE: 47
ctgatgagac cccgaaac                                                 18

<210> SEQ ID NO 48
<211> LENGTH: 18
<212> TYPE: DNA
<213> ORGANISM: Artificial Sequence
<220> FEATURE:
<223> OTHER INFORMATION: N4g5-21 clone

<400> SEQUENCE: 48
ctgatgagtt tacgaaac                                                 18

<210> SEQ ID NO 49
<211> LENGTH: 18
<212> TYPE: DNA
<213> ORGANISM: Artificial Sequence
<220> FEATURE:
<223> OTHER INFORMATION: N4g5-23 clone

<400> SEQUENCE: 49
ctgatgagac cccgaaac                                                 18

<210> SEQ ID NO 50
<211> LENGTH: 18
<212> TYPE: DNA
<213> ORGANISM: Artificial Sequence
<220> FEATURE:
<223> OTHER INFORMATION: N4g5-24 clone

<400> SEQUENCE: 50
ctgatgagtt accgaaac                                                 18

<210> SEQ ID NO 51
<211> LENGTH: 18
<212> TYPE: DNA
<213> ORGANISM: Artificial Sequence
<220> FEATURE:
<223> OTHER INFORMATION: N4g5-26 clone

<400> SEQUENCE: 51
ctgatgagtt accgaaac                                                 18

<210> SEQ ID NO 52
<211> LENGTH: 17
<212> TYPE: DNA
<213> ORGANISM: Artificial Sequence
<220> FEATURE:
<223> OTHER INFORMATION: N4g5-27 clone

<400> SEQUENCE: 52
ctgatgagac cccgaac                                                  17

<210> SEQ ID NO 53
<211> LENGTH: 18
<212> TYPE: DNA
<213> ORGANISM: Artificial Sequence
<220> FEATURE:
<223> OTHER INFORMATION: N4g5-28 clone

<400> SEQUENCE: 53
ctgatgagtt atcgaaac                                                 18
```

<210> SEQ ID NO 54
<211> LENGTH: 18
<212> TYPE: DNA
<213> ORGANISM: Artificial Sequence
<220> FEATURE:
<223> OTHER INFORMATION: N4g5-30 clone

<400> SEQUENCE: 54
ctgatgagtt tacgaaac                                                   18

<210> SEQ ID NO 55
<211> LENGTH: 18
<212> TYPE: DNA
<213> ORGANISM: Artificial Sequence
<220> FEATURE:
<223> OTHER INFORMATION: N4g5-31 clone

<400> SEQUENCE: 55
ctgatgagtt tacgaaac                                                   18

<210> SEQ ID NO 56
<211> LENGTH: 18
<212> TYPE: DNA
<213> ORGANISM: Artificial Sequence
<220> FEATURE:
<223> OTHER INFORMATION: N4g5-32 clone

<400> SEQUENCE: 56
ctgatgagac cccgaaac                                                   18

<210> SEQ ID NO 57
<211> LENGTH: 19
<212> TYPE: DNA
<213> ORGANISM: Artificial Sequence
<220> FEATURE:
<223> OTHER INFORMATION: N5g5-2 clone

<400> SEQUENCE: 57
ctgatgagtc ctacgaaac                                                  19

<210> SEQ ID NO 58
<211> LENGTH: 19
<212> TYPE: DNA
<213> ORGANISM: Artificial Sequence
<220> FEATURE:
<223> OTHER INFORMATION: N5g5-7 clone

<400> SEQUENCE: 58
ctgatgagtc ccacgaaac                                                  19

<210> SEQ ID NO 59
<211> LENGTH: 19
<212> TYPE: DNA
<213> ORGANISM: Artificial Sequence
<220> FEATURE:
<223> OTHER INFORMATION: N5g5-10 clone

<400> SEQUENCE: 59
ctgatgagaa tttcgaaac                                                  19

<210> SEQ ID NO 60
<211> LENGTH: 19
<212> TYPE: DNA
<213> ORGANISM: Artificial Sequence
<220> FEATURE:

<223> OTHER INFORMATION: N5g5-11 clone

<400> SEQUENCE: 60
ctgatgagtc ccacgaaac                                                    19

<210> SEQ ID NO 61
<211> LENGTH: 19
<212> TYPE: DNA
<213> ORGANISM: Artificial Sequence
<220> FEATURE:
<223> OTHER INFORMATION: N5g5-16 clone

<400> SEQUENCE: 61
ctgatgagtt aaacgaaac                                                    19

<210> SEQ ID NO 62
<211> LENGTH: 19
<212> TYPE: DNA
<213> ORGANISM: Artificial Sequence
<220> FEATURE:
<223> OTHER INFORMATION: N5g5-19 clone

<400> SEQUENCE: 62
ctgatgagtc ccacgaaac                                                    19

<210> SEQ ID NO 63
<211> LENGTH: 19
<212> TYPE: DNA
<213> ORGANISM: Artificial Sequence
<220> FEATURE:
<223> OTHER INFORMATION: N5g5-20 clone

<400> SEQUENCE: 63
ctgatgagtc ccccgaaac                                                    19

<210> SEQ ID NO 64
<211> LENGTH: 19
<212> TYPE: DNA
<213> ORGANISM: Artificial Sequence
<220> FEATURE:
<223> OTHER INFORMATION: N5g5-21 clone

<400> SEQUENCE: 64
ctgatgagca ccccgaaac                                                    19

<210> SEQ ID NO 65
<211> LENGTH: 19
<212> TYPE: DNA
<213> ORGANISM: Artificial Sequence
<220> FEATURE:
<223> OTHER INFORMATION: N5g5-22 clone

<400> SEQUENCE: 65
ctgatgagtc ccacgaaac                                                    19

<210> SEQ ID NO 66
<211> LENGTH: 19
<212> TYPE: DNA
<213> ORGANISM: Artificial Sequence
<220> FEATURE:
<223> OTHER INFORMATION: N5g5-25 clone

<400> SEQUENCE: 66
ctgatgagtg tcccgaaac                                                    19

```
<210> SEQ ID NO 67
<211> LENGTH: 19
<212> TYPE: DNA
<213> ORGANISM: Artificial Sequence
<220> FEATURE:
<223> OTHER INFORMATION: N5g5-26 clone

<400> SEQUENCE: 67
ctgatgagtt ttacgaaac                                                 19

<210> SEQ ID NO 68
<211> LENGTH: 18
<212> TYPE: DNA
<213> ORGANISM: Artificial Sequence
<220> FEATURE:
<223> OTHER INFORMATION: N5g5-27 clone

<400> SEQUENCE: 68
ctgatgagaa tttcgaac                                                  18

<210> SEQ ID NO 69
<211> LENGTH: 19
<212> TYPE: DNA
<213> ORGANISM: Artificial Sequence
<220> FEATURE:
<223> OTHER INFORMATION: N5g5-31 clone

<400> SEQUENCE: 69
ctgatgagtc ccacgaaac                                                 19

<210> SEQ ID NO 70
<211> LENGTH: 19
<212> TYPE: DNA
<213> ORGANISM: Artificial Sequence
<220> FEATURE:
<223> OTHER INFORMATION: N5g5-32 clone

<400> SEQUENCE: 70
ctgatgagtg ttacgaaac                                                 19

<210> SEQ ID NO 71
<211> LENGTH: 19
<212> TYPE: DNA
<213> ORGANISM: Artificial Sequence
<220> FEATURE:
<223> OTHER INFORMATION: N5g5-33 clone

<400> SEQUENCE: 71
ctgatgagtc ccacgaaac                                                 19

<210> SEQ ID NO 72
<211> LENGTH: 19
<212> TYPE: DNA
<213> ORGANISM: Artificial Sequence
<220> FEATURE:
<223> OTHER INFORMATION: N5g5-36 clone

<400> SEQUENCE: 72
ctgacgagtc ccacgaaac                                                 19

<210> SEQ ID NO 73
<211> LENGTH: 48
<212> TYPE: RNA
<213> ORGANISM: Artificial Sequence
<220> FEATURE:
<223> OTHER INFORMATION: N18g0 Ribozyme
<220> FEATURE:
```

```
<221> NAME/KEY: misc_feature
<222> LOCATION: (13)..(30)
<223> OTHER INFORMATION: n = c, g, a, u

<400> SEQUENCE: 73
ggcccaaugc aannnnnnnn nnnnnnnnnn aggaucaacg guaccgag         48

<210> SEQ ID NO 74
<211> LENGTH: 49
<212> TYPE: RNA
<213> ORGANISM: Artificial Sequence
<220> FEATURE:
<223> OTHER INFORMATION: N4g0 Ribozyme
<220> FEATURE:
<221> NAME/KEY: misc_feature
<222> LOCATION: (22)..(25)
<223> OTHER INFORMATION: n = c, g, a, u

<400> SEQUENCE: 74
gggcccaaug caacugauga gnnnncgaaa caggaucaac gguaccgag        49

<210> SEQ ID NO 75
<211> LENGTH: 32
<212> TYPE: RNA
<213> ORGANISM: Artificial Sequence
<220> FEATURE:
<223> OTHER INFORMATION: ribozyme
<220> FEATURE:
<221> NAME/KEY: misc_feature
<222> LOCATION: (12)..(29)
<223> OTHER INFORMATION: n = c, g, a, u/t

<400> SEQUENCE: 75
ggcccaugca annnnnnnnn nnnnnnnnna gg                          32

<210> SEQ ID NO 76
<211> LENGTH: 14
<212> TYPE: RNA
<213> ORGANISM: Artificial Sequence
<220> FEATURE:
<223> OTHER INFORMATION: ribozyme

<400> SEQUENCE: 76
ccugucuugc auaa                                              14

<210> SEQ ID NO 77
<211> LENGTH: 18
<212> TYPE: RNA
<213> ORGANISM: Artificial Sequence
<220> FEATURE:
<223> OTHER INFORMATION: ribozyme

<400> SEQUENCE: 77
cugaugauau auagaaac                                          18

<210> SEQ ID NO 78
<211> LENGTH: 18
<212> TYPE: RNA
<213> ORGANISM: Artificial Sequence
<220> FEATURE:
<223> OTHER INFORMATION: ribozyme

<400> SEQUENCE: 78
cugacgaacu caugaaac                                          18

<210> SEQ ID NO 79
<211> LENGTH: 18
```

```
<212> TYPE: RNA
<213> ORGANISM: Artificial Sequence
<220> FEATURE:
<223> OTHER INFORMATION: ribozyme

<400> SEQUENCE: 79
cugaugauaa acugaaac                                                    18

<210> SEQ ID NO 80
<211> LENGTH: 18
<212> TYPE: RNA
<213> ORGANISM: Artificial Sequence
<220> FEATURE:
<223> OTHER INFORMATION: ribozyme

<400> SEQUENCE: 80
cugaugaacu ucugaaac                                                    18

<210> SEQ ID NO 81
<211> LENGTH: 18
<212> TYPE: RNA
<213> ORGANISM: Artificial Sequence
<220> FEATURE:
<223> OTHER INFORMATION: ribozyme

<400> SEQUENCE: 81
cugacgauga aacgaaac                                                    18

<210> SEQ ID NO 82
<211> LENGTH: 18
<212> TYPE: RNA
<213> ORGANISM: Artificial Sequence
<220> FEATURE:
<223> OTHER INFORMATION: ribozyme

<400> SEQUENCE: 82
cugacgacaa cgugaaac                                                    18

<210> SEQ ID NO 83
<211> LENGTH: 18
<212> TYPE: RNA
<213> ORGANISM: Artificial Sequence
<220> FEATURE:
<223> OTHER INFORMATION: ribozyme

<400> SEQUENCE: 83
cugaugacgc acugaaac                                                    18

<210> SEQ ID NO 84
<211> LENGTH: 18
<212> TYPE: RNA
<213> ORGANISM: Artificial Sequence
<220> FEATURE:
<223> OTHER INFORMATION: ribozyme

<400> SEQUENCE: 84
cugaugaagc agugaaac                                                    18

<210> SEQ ID NO 85
<211> LENGTH: 17
<212> TYPE: RNA
<213> ORGANISM: Artificial Sequence
<220> FEATURE:
<223> OTHER INFORMATION: ribozyme

<400> SEQUENCE: 85
```
cugaugagua uugaaac 17

<210> SEQ ID NO 86
<211> LENGTH: 17
<212> TYPE: RNA
<213> ORGANISM: Artificial Sequence
<220> FEATURE:
<223> OTHER INFORMATION: ribozyme

<400> SEQUENCE: 86
cugaugagaa ucgaaac 17

<210> SEQ ID NO 87
<211> LENGTH: 18
<212> TYPE: RNA
<213> ORGANISM: Artificial Sequence
<220> FEATURE:
<223> OTHER INFORMATION: ribozyme

<400> SEQUENCE: 87
cugacgacca agagaaac 18

<210> SEQ ID NO 88
<211> LENGTH: 18
<212> TYPE: RNA
<213> ORGANISM: Artificial Sequence
<220> FEATURE:
<223> OTHER INFORMATION: ribozyme

<400> SEQUENCE: 88
cugaugagac aucgaaac 18

<210> SEQ ID NO 89
<211> LENGTH: 18
<212> TYPE: RNA
<213> ORGANISM: Artificial Sequence
<220> FEATURE:
<223> OTHER INFORMATION: ribozyme

<400> SEQUENCE: 89
cugaugaucc acugaaac 18

<210> SEQ ID NO 90
<211> LENGTH: 18
<212> TYPE: RNA
<213> ORGANISM: Artificial Sequence
<220> FEATURE:
<223> OTHER INFORMATION: ribozyme

<400> SEQUENCE: 90
cugaggagga gucgaaac 18

<210> SEQ ID NO 91
<211> LENGTH: 18
<212> TYPE: RNA
<213> ORGANISM: Artificial Sequence
<220> FEATURE:
<223> OTHER INFORMATION: ribozyme

<400> SEQUENCE: 91
cugaugaugc cuugaaac 18

<210> SEQ ID NO 92
<211> LENGTH: 18
<212> TYPE: RNA
<213> ORGANISM: Artificial Sequence

```
<220> FEATURE:
<223> OTHER INFORMATION: ribozyme

<400> SEQUENCE: 92
cugaagagaa ucugaaac                                                    18

<210> SEQ ID NO 93
<211> LENGTH: 18
<212> TYPE: RNA
<213> ORGANISM: Artificial Sequence
<220> FEATURE:
<223> OTHER INFORMATION: ribozyme

<400> SEQUENCE: 93
cugaugacau gccgaaac                                                    18

<210> SEQ ID NO 94
<211> LENGTH: 18
<212> TYPE: RNA
<213> ORGANISM: Artificial Sequence
<220> FEATURE:
<223> OTHER INFORMATION: ribozyme

<400> SEQUENCE: 94
cugaugauac cuugaaac                                                    18

<210> SEQ ID NO 95
<211> LENGTH: 18
<212> TYPE: RNA
<213> ORGANISM: Artificial Sequence
<220> FEATURE:
<223> OTHER INFORMATION: ribozyme

<400> SEQUENCE: 95
cugaugaguu auugaaac                                                    18

<210> SEQ ID NO 96
<211> LENGTH: 18
<212> TYPE: RNA
<213> ORGANISM: Artificial Sequence
<220> FEATURE:
<223> OTHER INFORMATION: ribozyme

<400> SEQUENCE: 96
cugaugauua uugaaacu                                                    18

<210> SEQ ID NO 97
<211> LENGTH: 18
<212> TYPE: RNA
<213> ORGANISM: Artificial Sequence
<220> FEATURE:
<223> OTHER INFORMATION: ribozyme

<400> SEQUENCE: 97
cugacgaaca aaugaaac                                                    18

<210> SEQ ID NO 98
<211> LENGTH: 18
<212> TYPE: RNA
<213> ORGANISM: Artificial Sequence
<220> FEATURE:
<223> OTHER INFORMATION: ribozyme

<400> SEQUENCE: 98
cugaugacau uaagaaac                                                    18
```

<210> SEQ ID NO 99
<211> LENGTH: 18
<212> TYPE: RNA
<213> ORGANISM: Artificial Sequence
<220> FEATURE:
<223> OTHER INFORMATION: ribozyme

<400> SEQUENCE: 99
cugaagaaua aaagaaac                                                    18

<210> SEQ ID NO 100
<211> LENGTH: 18
<212> TYPE: RNA
<213> ORGANISM: Artificial Sequence
<220> FEATURE:
<223> OTHER INFORMATION: ribozyme

<400> SEQUENCE: 100
cugaugaaac ccugaaac                                                    18

<210> SEQ ID NO 101
<211> LENGTH: 18
<212> TYPE: RNA
<213> ORGANISM: Artificial Sequence
<220> FEATURE:
<223> OTHER INFORMATION: ribozyme

<400> SEQUENCE: 101
cugaagaaag ccugaaac                                                    18

<210> SEQ ID NO 102
<211> LENGTH: 18
<212> TYPE: RNA
<213> ORGANISM: Artificial Sequence
<220> FEATURE:
<223> OTHER INFORMATION: ribozyme

<400> SEQUENCE: 102
cugaugauga cuggaaac                                                    18

<210> SEQ ID NO 103
<211> LENGTH: 18
<212> TYPE: RNA
<213> ORGANISM: Artificial Sequence
<220> FEATURE:
<223> OTHER INFORMATION: ribozyme

<400> SEQUENCE: 103
cugacgauuc uaggaaac                                                    18

<210> SEQ ID NO 104
<211> LENGTH: 18
<212> TYPE: RNA
<213> ORGANISM: Artificial Sequence
<220> FEATURE:
<223> OTHER INFORMATION: ribozyme

<400> SEQUENCE: 104
cugacgaagu auugaaac                                                    18

<210> SEQ ID NO 105
<211> LENGTH: 18
<212> TYPE: RNA
<213> ORGANISM: Artificial Sequence
<220> FEATURE:
<223> OTHER INFORMATION: ribozyme

```
<400> SEQUENCE: 105
cugaugaacu agggaaac                                                    18

<210> SEQ ID NO 106
<211> LENGTH: 18
<212> TYPE: RNA
<213> ORGANISM: Artificial Sequence
<220> FEATURE:
<223> OTHER INFORMATION: ribozyme

<400> SEQUENCE: 106
cugaugauug uuagaaac                                                    18

<210> SEQ ID NO 107
<211> LENGTH: 18
<212> TYPE: RNA
<213> ORGANISM: Artificial Sequence
<220> FEATURE:
<223> OTHER INFORMATION: ribozyme

<400> SEQUENCE: 107
cugaugauua ggcgaaac                                                    18

<210> SEQ ID NO 108
<211> LENGTH: 18
<212> TYPE: RNA
<213> ORGANISM: Artificial Sequence
<220> FEATURE:
<223> OTHER INFORMATION: ribozyme

<400> SEQUENCE: 108
cugacgacgc cccgaaac                                                    18

<210> SEQ ID NO 109
<211> LENGTH: 18
<212> TYPE: RNA
<213> ORGANISM: Artificial Sequence
<220> FEATURE:
<223> OTHER INFORMATION: ribozyme

<400> SEQUENCE: 109
cugaagagac cacgaaac                                                    18

<210> SEQ ID NO 110
<211> LENGTH: 18
<212> TYPE: RNA
<213> ORGANISM: Artificial Sequence
<220> FEATURE:
<223> OTHER INFORMATION: ribozyme

<400> SEQUENCE: 110
cugaugaaga aaugaaac                                                    18

<210> SEQ ID NO 111
<211> LENGTH: 18
<212> TYPE: RNA
<213> ORGANISM: Artificial Sequence
<220> FEATURE:
<223> OTHER INFORMATION: ribozyme

<400> SEQUENCE: 111
cugacgaauu uuggaaac                                                    18

<210> SEQ ID NO 112
```

```
<211> LENGTH: 18
<212> TYPE: RNA
<213> ORGANISM: Artificial Sequence
<220> FEATURE:
<223> OTHER INFORMATION: ribozyme

<400> SEQUENCE: 112
cugaugaggg gacgaaac                                                 18

<210> SEQ ID NO 113
<211> LENGTH: 18
<212> TYPE: RNA
<213> ORGANISM: Artificial Sequence
<220> FEATURE:
<223> OTHER INFORMATION: ribozyme

<400> SEQUENCE: 113
cugaugauuu ggugaaac                                                 18

<210> SEQ ID NO 114
<211> LENGTH: 18
<212> TYPE: RNA
<213> ORGANISM: Artificial Sequence
<220> FEATURE:
<223> OTHER INFORMATION: ribozyme

<400> SEQUENCE: 114
cugaugagcu aacgaaac                                                 18

<210> SEQ ID NO 115
<211> LENGTH: 18
<212> TYPE: RNA
<213> ORGANISM: Artificial Sequence
<220> FEATURE:
<223> OTHER INFORMATION: ribozyme

<400> SEQUENCE: 115
cugaugaaac gccgaaac                                                 18

<210> SEQ ID NO 116
<211> LENGTH: 17
<212> TYPE: RNA
<213> ORGANISM: Artificial Sequence
<220> FEATURE:
<223> OTHER INFORMATION: ribozyme

<400> SEQUENCE: 116
cugaugaaua uugaaac                                                  17

<210> SEQ ID NO 117
<211> LENGTH: 18
<212> TYPE: RNA
<213> ORGANISM: Artificial Sequence
<220> FEATURE:
<223> OTHER INFORMATION: ribozyme

<400> SEQUENCE: 117
cugaugaaac caugaaac                                                 18

<210> SEQ ID NO 118
<211> LENGTH: 18
<212> TYPE: RNA
<213> ORGANISM: Artificial Sequence
<220> FEATURE:
<223> OTHER INFORMATION: ribozyme

<400> SEQUENCE: 118
```
cugaugaauc ugugaaac                                                  18

<210> SEQ ID NO 119
<211> LENGTH: 18
<212> TYPE: RNA
<213> ORGANISM: Artificial Sequence
<220> FEATURE:
<223> OTHER INFORMATION: ribozyme

<400> SEQUENCE: 119
cugaugauau uuugaaac                                                  18

<210> SEQ ID NO 120
<211> LENGTH: 18
<212> TYPE: RNA
<213> ORGANISM: Artificial Sequence
<220> FEATURE:
<223> OTHER INFORMATION: ribozyme

<400> SEQUENCE: 120
cugaugaggg gacgaaac                                                  18

<210> SEQ ID NO 121
<211> LENGTH: 18
<212> TYPE: RNA
<213> ORGANISM: Artificial Sequence
<220> FEATURE:
<223> OTHER INFORMATION: ribozyme

<400> SEQUENCE: 121
cugaugagca aacgaaac                                                  18

<210> SEQ ID NO 122
<211> LENGTH: 18
<212> TYPE: RNA
<213> ORGANISM: Artificial Sequence
<220> FEATURE:
<223> OTHER INFORMATION: ribozyme

<400> SEQUENCE: 122
cugacgacuu ggagaaac                                                  18

<210> SEQ ID NO 123
<211> LENGTH: 18
<212> TYPE: RNA
<213> ORGANISM: Artificial Sequence
<220> FEATURE:
<223> OTHER INFORMATION: ribozyme

<400> SEQUENCE: 123
cugaugauau uaugaaac                                                  18

<210> SEQ ID NO 124
<211> LENGTH: 18
<212> TYPE: RNA
<213> ORGANISM: Artificial Sequence
<220> FEATURE:
<223> OTHER INFORMATION: ribozyme

<400> SEQUENCE: 124
cugacgaguc uacgaaac                                                  18

<210> SEQ ID NO 125
<211> LENGTH: 18
<212> TYPE: RNA

<213> ORGANISM: Artificial Sequence
<220> FEATURE:
<223> OTHER INFORMATION: ribozyme

<400> SEQUENCE: 125
cugaugaggc aacgaaac                                           18

<210> SEQ ID NO 126
<211> LENGTH: 18
<212> TYPE: RNA
<213> ORGANISM: Artificial Sequence
<220> FEATURE:
<223> OTHER INFORMATION: ribozyme

<400> SEQUENCE: 126
cugaugaggc aacgaaac                                           18

<210> SEQ ID NO 127
<211> LENGTH: 18
<212> TYPE: RNA
<213> ORGANISM: Artificial Sequence
<220> FEATURE:
<223> OTHER INFORMATION: ribozyme

<400> SEQUENCE: 127
cugaugaguc cccgaaac                                           18

<210> SEQ ID NO 128
<211> LENGTH: 18
<212> TYPE: RNA
<213> ORGANISM: Artificial Sequence
<220> FEATURE:
<223> OTHER INFORMATION: ribozyme

<400> SEQUENCE: 128
cugacgaggu aacgaaac                                           18

<210> SEQ ID NO 129
<211> LENGTH: 18
<212> TYPE: RNA
<213> ORGANISM: Artificial Sequence
<220> FEATURE:
<223> OTHER INFORMATION: ribozyme

<400> SEQUENCE: 129
cugaugacgc caggaaac                                           18

<210> SEQ ID NO 130
<211> LENGTH: 18
<212> TYPE: RNA
<213> ORGANISM: Artificial Sequence
<220> FEATURE:
<223> OTHER INFORMATION: ribozyme

<400> SEQUENCE: 130
cugaagagca accgaaac                                           18

<210> SEQ ID NO 131
<211> LENGTH: 18
<212> TYPE: RNA
<213> ORGANISM: Artificial Sequence
<220> FEATURE:
<223> OTHER INFORMATION: ribozyme

<400> SEQUENCE: 131
cugaagagcu accgaaac                                           18

<210> SEQ ID NO 132
<211> LENGTH: 18
<212> TYPE: RNA
<213> ORGANISM: Artificial Sequence
<220> FEATURE:
<223> OTHER INFORMATION: ribozyme

<400> SEQUENCE: 132
cugaugagug accgaaac                                                18

<210> SEQ ID NO 133
<211> LENGTH: 18
<212> TYPE: RNA
<213> ORGANISM: Artificial Sequence
<220> FEATURE:
<223> OTHER INFORMATION: ribozyme

<400> SEQUENCE: 133
cugacgaguu uacgaaac                                                18

<210> SEQ ID NO 134
<211> LENGTH: 18
<212> TYPE: RNA
<213> ORGANISM: Artificial Sequence
<220> FEATURE:
<223> OTHER INFORMATION: ribozyme

<400> SEQUENCE: 134
cugaagaguu uacgaaac                                                18

<210> SEQ ID NO 135
<211> LENGTH: 18
<212> TYPE: RNA
<213> ORGANISM: Artificial Sequence
<220> FEATURE:
<223> OTHER INFORMATION: ribozyme

<400> SEQUENCE: 135
cugaagagua aucgaaac                                                18

<210> SEQ ID NO 136
<211> LENGTH: 18
<212> TYPE: RNA
<213> ORGANISM: Artificial Sequence
<220> FEATURE:
<223> OTHER INFORMATION: ribozyme

<400> SEQUENCE: 136
cugaugagua accgaaac                                                18

<210> SEQ ID NO 137
<211> LENGTH: 18
<212> TYPE: RNA
<213> ORGANISM: Artificial Sequence
<220> FEATURE:
<223> OTHER INFORMATION: ribozyme

<400> SEQUENCE: 137
cugauguguc cacgaaac                                                18

<210> SEQ ID NO 138
<211> LENGTH: 18
<212> TYPE: RNA
<213> ORGANISM: Artificial Sequence
<220> FEATURE:

```
<223> OTHER INFORMATION: ribozyme

<400> SEQUENCE: 138
cugaugagca cccgaaac                                               18

<210> SEQ ID NO 139
<211> LENGTH: 18
<212> TYPE: RNA
<213> ORGANISM: Artificial Sequence
<220> FEATURE:
<223> OTHER INFORMATION: ribozyme

<400> SEQUENCE: 139
cugaugagcu aacgaaac                                               18

<210> SEQ ID NO 140
<211> LENGTH: 18
<212> TYPE: RNA
<213> ORGANISM: Artificial Sequence
<220> FEATURE:
<223> OTHER INFORMATION: ribozyme

<400> SEQUENCE: 140
cugacgagcu cccgaaac                                               18

<210> SEQ ID NO 141
<211> LENGTH: 18
<212> TYPE: RNA
<213> ORGANISM: Artificial Sequence
<220> FEATURE:
<223> OTHER INFORMATION: ribozyme

<400> SEQUENCE: 141
cugaugaguu uucgaaac                                               18

<210> SEQ ID NO 142
<211> LENGTH: 18
<212> TYPE: RNA
<213> ORGANISM: Artificial Sequence
<220> FEATURE:
<223> OTHER INFORMATION: ribozyme

<400> SEQUENCE: 142
cugaugagca uacgaaac                                               18

<210> SEQ ID NO 143
<211> LENGTH: 18
<212> TYPE: RNA
<213> ORGANISM: Artificial Sequence
<220> FEATURE:
<223> OTHER INFORMATION: ribozyme

<400> SEQUENCE: 143
cugaggagaa accgaaac                                               18

<210> SEQ ID NO 144
<211> LENGTH: 18
<212> TYPE: RNA
<213> ORGANISM: Artificial Sequence
<220> FEATURE:
<223> OTHER INFORMATION: ribozyme

<400> SEQUENCE: 144
cugacgaguu aacgaaac                                               18
```

```
<210> SEQ ID NO 145
<211> LENGTH: 18
<212> TYPE: RNA
<213> ORGANISM: Artificial Sequence
<220> FEATURE:
<223> OTHER INFORMATION: ribozyme

<400> SEQUENCE: 145
cugacgaugg uaugaaac                                                   18

<210> SEQ ID NO 146
<211> LENGTH: 18
<212> TYPE: RNA
<213> ORGANISM: Artificial Sequence
<220> FEATURE:
<223> OTHER INFORMATION: ribozyme

<400> SEQUENCE: 146
cugaugagcu accgaaac                                                   18

<210> SEQ ID NO 147
<211> LENGTH: 18
<212> TYPE: RNA
<213> ORGANISM: Artificial Sequence
<220> FEATURE:
<223> OTHER INFORMATION: ribozyme

<400> SEQUENCE: 147
cugaagaguu accgaaac                                                   18

<210> SEQ ID NO 148
<211> LENGTH: 18
<212> TYPE: RNA
<213> ORGANISM: Artificial Sequence
<220> FEATURE:
<223> OTHER INFORMATION: ribozyme

<400> SEQUENCE: 148
cugaugagcu aacgaaac                                                   18

<210> SEQ ID NO 149
<211> LENGTH: 18
<212> TYPE: RNA
<213> ORGANISM: Artificial Sequence
<220> FEATURE:
<223> OTHER INFORMATION: ribozyme

<400> SEQUENCE: 149
cugaugagca aacgaaac                                                   18

<210> SEQ ID NO 150
<211> LENGTH: 18
<212> TYPE: RNA
<213> ORGANISM: Artificial Sequence
<220> FEATURE:
<223> OTHER INFORMATION: ribozyme

<400> SEQUENCE: 150
cugaagagcc aucgaaac                                                   18

<210> SEQ ID NO 151
<211> LENGTH: 18
<212> TYPE: RNA
<213> ORGANISM: Artificial Sequence
<220> FEATURE:
<223> OTHER INFORMATION: ribozyme
```

```
<400> SEQUENCE: 151
cugaugagcg aacgaaac                                                 18

<210> SEQ ID NO 152
<211> LENGTH: 18
<212> TYPE: RNA
<213> ORGANISM: Artificial Sequence
<220> FEATURE:
<223> OTHER INFORMATION: ribozyme

<400> SEQUENCE: 152
cugaugagcu cacgaaac                                                 18

<210> SEQ ID NO 153
<211> LENGTH: 18
<212> TYPE: RNA
<213> ORGANISM: Artificial Sequence
<220> FEATURE:
<223> OTHER INFORMATION: ribozyme

<400> SEQUENCE: 153
cugaugagac cacgaaac                                                 18
```

MINIRIBOZYMES ACTIVE AT LOW MAGNESIUM ION CONCENTRATIONS

This application is a continuation of PCT International Application No. PCT/AU99/01162, filed 24 Dec. 1999, designating the United States of America, which claims priority of Australian Application No. PP7951/98, filed Dec. 24, 1998, the contents of which are hereby incorporated by reference into the present application.

FIELD OF THE INVENTION

This invention relates to minimised ribozymes, herein referred to as "miniribozymes", and in particular it relates to a class of miniribozymes which has been selected on the basis of the very high cleavage rates by the members of the class at low $Mg^{2+}$ concentration. This invention also extends to compositions comprising these miniribozymes, to transfer vectors and host cells as well as methods of cleaving a target RNA in a subject and other methods of use of these miniribozymes.

Throughout this application, various references are cited in brackets. The full citations may be found in the numerical list of references immediately following the Example(s). These publications are hereby incorporated by reference into the present application.

BACKGROUND OF THE INVENTION

There is currently much interest in the catalytic potential of RNA both as a candidate molecule for precellular evolution and as gene targeted therapeutics. To date there are in excess of 30 distinct RNA motifs known to perform catalysis in the absence of protein. These include ribozymes derived from natural RNAs and also those produced by in vitro selection (1). The reactive capacity of any polynucleotide is a function of the chemistry of the individual nucleotides and the secondary and tertiary structure of the polymer, both of which are affected by coordination with metal ions (2,3). Structure within an oligonucleotide can be viewed as a direct function of the sequence identity. The catalytic versatility of a nucleic acid is therefore amenable to combinatorial studies, such as in vitro selection, involving the artificial manipulation of a discrete sequence space in response to selective pressure.

The 2' hydroxyl of ribonucleic acids is a crucial functional entity permitting nucleophilic attack by the deprotonated form on an adjacent bridging phosphate ester leading to hydrolysis (giving 5' OH and 2'-3' cyclic phosphate ends) via a pentacoordinate transition state (4–7). Enzymes of either nucleic acid or protein composition that catalyse reactions of phosphates are invariably metal ion dependent (8). Metals have been recruited by biology for this purpose presumably because phosphates are a favourable metal ion ligand, and because coordination with metals withdraws electron density from the phosphorus centre, making it more susceptible to nucleophilic attack. Metal ions may also assist the deprotonation of the attacking nucleophile and assist the stabilisation of the developing negative charge on the leaving group (8–10).

The hammerhead ribozyme was first identified as a self (cis) cleaving sequence found in a number of small, circular, RNA pathogens (virusoids and viroids) found in plants, and a satellite RNA found in newt (11). Its consensus structure consists of three helical regions which form at their junction, a conserved bed of 15 nucleotides. The bulk of the conserved nucleotides can be located on a single oligoribonucleotide constituting an enzymatic entity capable of cleaving multiple substrates (12,13). Ribozymes designed accordingly can be directed in trans against any RNA substrate containing an endogenous 5' UH (where H=C, U, or A) (14–16). There is significant interest in these enzymes because they offer a means of specifically inactivating deleterious RNA, eg. viral or oncogenic mRNAs, and thereby ameliorating disease.

Hammerhead cleavage of an RNA phosphodiester bond exhibits divalent metal ion dependence (17) typical of this form of catalysis in nature. Generally the metal ion is proposed to act both structurally to augment and direct specific helical interactions, and as a catalytic co-factor functional in the chemical step of the reaction (2,9,18). $Mg^{2+}$ is known to perform both these roles effectively. Bassi et al (19–21) report that there is a two stage folding process leading to formation of the ground state, each with a specific $Mg^{2+}$ requirement. Once the ground state is obtained, $Mg^{2+}$ is thought to play a role in activating the 2' OH nucleophile of C17, either by direct coordination, or by providing an appropriately positioned basic group (Mg—OH), to effect deprotonation, promoting nucleophilic attack on the adjacent phosphorus (22–24).

The role of helix II in the hammerhead ribozyme has been investigated in several deletion studies (25–28). The presence of Watson-Crick base pairing in this region is thought to stabilise the active conformation of the conserved nucleotides stacked above it (28). The role of helix II is therefore seemingly to limit the number of steric possibilities closer to the cleavage site. This effect is no doubt variable and will depend on the composition of nucleotides between positions A9 and G12. Crystal structures for the hammerhead ribozyme show proximity between helix I and helix II (29,30). These structures suggest a plausible interaction (perhaps $Mg^{2+}$ mediated) between helix I and helix II. Whilst this interaction is remote from the cleavage site, it affects the global architecture of the molecule, and thus the cleavage rate. It has been speculated that the interaction between helix I and II may in fact stabilise an inactive conformation (31). The truncation of helix I appears to amend this interaction and allows higher rates of catalysis to be observed (31). Minimisation strategies involving helix II therefore might offer an alternative means of circumventing or closing down this particular equilibrium pathway, and thereby improve the catalytic outcome.

Miniribozymes are derivatives of the hammerhead ribozyme where helix II has been replaced by a linker with a single Watson-Crick base pair (32). This minimisation strategy has created a novel structural format. Whilst the full length ribozyme has been subject to selection over evolutionary time, size constrained, trans cleaving ribozymes have not been exposed to selection in nature. Minimised ribozymes have been shown to cleave long RNAs more efficiently than full length hammerheads (27), and could therefore provide improved trans cleaving activity in a cellular environment.

The work leading to the present invention has included in vitro optimisation of the novel miniribozyme structure. In particular, in vitro selection was used to search an 18 nt RNA sequence space corresponding in size to a miniribozyme (FIG. 1). The aims were primarily to identify all motifs within this size constrained domain, capable of supporting $Mg^{2+}$ dependent phosphodiester cleavage of a 29 mer RNA substrate containing a 13 nt segment of human IL-2 mRNA. Subsequently, the aim was to direct the active component of this population towards optimum catalytic efficiency at low concentrations of $Mg^{2+}$ (0.5–2 mM) such as occur intracellularly (33). This work has shown that the active population consisted almost entirely of molecules containing conserved nucleotides conforming to recognised hammerhead motifs. This set of molecules exhibited highly variable catalytic activity. It was an expectation that hammerhead-like molecules would form a subset of the active sequence space. An important goal was therefore to optimise the nucleotide composition between positions 9 and 12 amongst hammerhead-like molecules, within a context of size constraint, and therefore to evolve a linker between A9 and G12 which most efficiently favours equilibration of the active conformation.

SUMMARY OF THE INVENTION

This invention is directed to a selected class of miniribozymes, capable of hybridising with a target RNA to be cleaved, and exhibiting very high cleavage rates at low $Mg^{2+}$ concentration. These miniribozymes may be used both in vitro and in vivo, and their uses extend to both the diagnostic and therapeutic fields, that is, these miniribozymes may be used as diagnostic or therapeutic agents.

DETAILED DESCRIPTION OF THE INVENTION

In one aspect, the present invention provides a compound of the formula IA (SEQ ID NO:1) or 1B (SEQ ID NO:2):

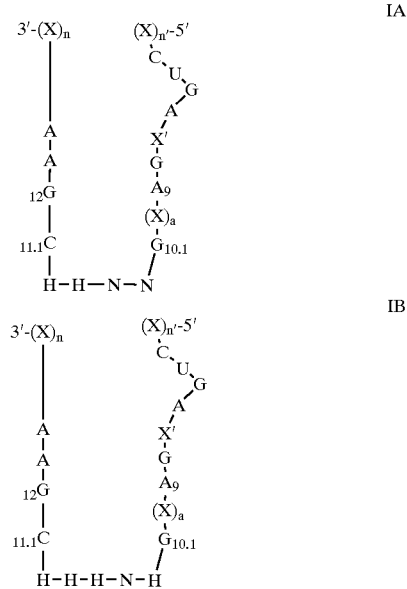

wherein each X represents a nucleotide which may be the same or different and may be substituted or modified in its sugar, base or phosphate; and wherein $G_{10.1}$ and $C_{11.1}$ each represent a nucleotide which may be substituted or modified in its sugar (which may be ribose or deoxyribose), base or phosphate;

wherein each of C, G, A and U represents a ribonucleotide which may be substituted or modified in its sugar, base or phosphate;

wherein each of $(X)_n$ and $(X)_{n'}$ represents an oligonucleotide having a pre-determined sequence which is capable of hybridizing with an RNA target sequence to be cleaved, such RNA target sequence not being present within the compound, and each of n and n' represents an integer which defines the number of nucleotides in the oligonucleotide;

wherein X' represents a ribonucleotide selected from C, G, A and U which may be substituted or modified in its sugar, base or phosphate;

wherein a defines the number of nucleotides in $(X)_a$ and may be 0 or 1 and if 0, the A located 5' of $(X)_a$ is bonded to the G located 3' of $(X)_a$;

wherein each solid line represents a chemical linkage providing covalent bonds between the nucleotides located on either side thereof;

wherein each N represents a nucleotide selected from C, G, A and U/T which may be substituted or modified in its sugar (which may be ribose or deoxyribose), base or phosphate and wherein each H represents a nucleotide selected from C, A and U/T, which may be substituted or modified in its sugar (which may be ribose or deoxyribose), base or phosphate; with the proviso that the sequence 5'-NNHH-3' is not UUUU or TTTT, CUCC, AAUU or GGCA.

In formulae IA and 1B, C represents a nucleotide in which the base is cytosine, G represents a nucleotide in which the base is guanine, A represents a nucleotide in which the base is adenine, U represents a nucleotide in which the base is uracil, and T represents a nucleotide in which the base is thymine.

In one embodiment of the present invention, the oligonucleotide 3'-$(X)_n$- in the compound of formula I is 3'-$(X)_{n-1}$-A-.

The compounds of formula IA as set out above, include the linker sequence 5'-NNHH-3' which is preferably selected from the following classes of linker sequences:

Class I: YRHH, wherein Y is C or U, R is G or A, and H is C, A or U.

Class II: DYHH, wherein D is G, A or U, Y is C or U, and H is C, A or U.

Class III: GHHA, wherein H is C, A or U.

Preferred linker sequences in Class I are the sequences CGUU, UGUU and UAAC. Preferred linker sequences in Class II are sequences of the class WYHH (wherein W is A or U, Y is C or U, and H is C, A or U), particularly the sequences ACCC, AUUU, UCCC, AUUC, AUUA, ACAC, AUAA and AUAC. Particularly preferred linker sequences in Class II are the pyrimidine rich subclass of sequences UUHH, wherein H is C, A or U, in particular the sequences UUAC, UUCC, UUUC, UUUA, UUAA and UUAU. Preferred linker sequences in Class III are the sequences GUAM and GAUA.

The compounds of formula 1B as set out above include the linker sequence 5'-HNHHH-3' which is preferably selected from the sequences UCCCA, UCCCC, UCCUA, AAUUU, UUAAA, UUUUA, UGUCC, UGUUA and CACCC. Particularly preferred sequences are UCCCC, UGUCC and CACCC.

While the preferred linker sequences described above are described as RNA sequences, it will be understood that these preferred linker sequences also include the corresponding DNA sequences.

In general terms, the compounds of the present invention are synthetic, non-naturally occurring oligonucleotide compounds comprising a sequence of nucleotides which includes a catalytic region and hybridizing regions whose sequences are capable of hybridizing with a predetermined RNA target sequence to be cleaved.

The present invention is also directed to compositions comprising a compound of formula IA or 1B above in association with an acceptable carrier.

The invention is also directed to an oligonucleotide transfer vector containing a nucleotide sequence which on transcription gives rise to a compound of formula IA or 1B above. The transfer vector may be a bacterial plasmid, a bacteriophage DNA, a cosmid, an eukaryotic viral DNA, a plant DNA virus, a composite geminivirus, a binary plant expression vector (Ri or Ti), an infective phage particle or a portion thereof. The packaged oligonucleotide transfer vector may contain promoter sequences for RNA polymerase II, human tRNA$^{val}$, plant tRNA, human tRNA, snRNA promoter or RNA polymerase III. The invention also includes a host cell transformed by the transfer vector. The host cell may be a prokaryotic host cell or an eukaryotic host cell, such as an E. coli host cell, a monkey COS host cell, a Chinese hamster ovary host cell, a mammalian host cell, a plant host cell, a plant protoplast host cell, a hematopoietic host cell, a stem cell, a hematopoietic progenitor cell, a lymphoid cell, a T-cell, a B-cell, pre-B cell, a CD4+T-cell or a peripheral blood mononuclear cell.

The invention also provides a method of cleaving a target mRNA in a subject which comprises administering to the subject an effective amount of a compound of formula IA or 1B above or a vector capable of expressing the compound. The administration may be topical in an amount between 1 ng and 10 mg. The administration may also be systemic and administered in an amount between 1 ng and 500 µg/kg weight/day. The administration may also be aerosol administration.

The invention also provides a method of cleaving a target mRNA in a host cell which comprises administering to the host cell an effective amount of a compound of formula IA or 1B or a vector capable of expressing the compound.

The compound of formula IA or 1B may further comprise an antisense nucleic acid which is capable of hybridizing with an RNA target sequence. The compound may further comprise at least one additional non-naturally occurring oligonucleotide compound which comprises nucleotides whose sequence defines a conserved catalytic region and nucleotides whose sequence is capable of hybridizing with a predetermined target sequence. The additional non-naturally occurring oligonucleotide compound may be a hammerhead ribozyme, a miniribozyme, a hairpin ribozyme, a hepatitis delta ribozyme, an RNAase P ribozyme, a Group I intron, or a combination thereof. See for example: hammerhead ribozyme (Haseloff et al. U.S. Pat. No. 5,254,678, issued Oct. 18, 1993; Jennings U.S. Pat. No. 5,298,612, issued Mar. 29, 1994); Group I introns, (Cech et al. U.S. Pat. No. 4,740,463, issued Apr. 26, 1988; Altman et al. U.S. Pat. No. 5,168,053, issued Dec. 1, 1992 or PCT International Publication No WO 92/03566); hepatitis delta ribozymes (PCT International Application No. WO 90/05157) and hairpin ribozymes (European Patent Application No. EP 360,257).

Preferred cleavage sites in the target RNA have the sequence "NUH" (wherein N represents C, G, A or U and H represents C, A or U), preferably GUC, GUU, GUA, UUA and UUC. By way of example, suitable reaction conditions may comprise a temperature from about 4° C. to about 60° C., preferably from about 10° C. to about 45° C., more preferably from about 20° C. to about 43° C.; pH from about 6.0 to about 9.0 and concentration of divalent cation (such as $Mg^{2+}$) from about 0.1 to about 100 mM, preferably from about 1 to about 100 mM (most preferably 1 to 20 mM). The nucleotides of the sequences $(X)_n$ and $(X)_{n'}$ of the compounds above may be of any number and sequence sufficient to enable hybridization with the nucleotides in the target RNA, as described herein. Ribozymes containing a small number of nucleotides in each of the groups $(X)_n$ and $(X)_{n'}$ of the compounds above (such as four nucleotides) would generally be incubated at lower temperatures, such as about 20° C. to about 25° C. to aid hybridizing with the nucleotide sequences in the substrate. The number of nucleotides n and n' in $(X)_n$ and $(X)_{n'}$ are not necessarily equal. Preferably, the sum of n+n' is greater than 14.

The invention is also directed to covalently-linked multiple ribozymes, where each ribozyme is directed to a target sequence which may be the same or different. In addition these compounds may be covalently attached to an antisense molecule which may be 10 to 100 bases in length. Antisense sequences capable of hybridizing to an RNA in a mammal or plant are well known (see Shewmaker et al. U.S. Pat. No. 5,107,065, issued Apr. 21, 1992). As the ribozyme acts as an enzyme, showing turnover, the ratio of ribozyme to substrate may vary widely.

A target RNA containing a suitable cleavage site such as an NUH site as described above may be incubated with a compound described above. The nucleotide sequences $(X)_n$ and $(X)_{n'}$ of the compounds above are selected to hybridize with their substrate. They may be selected so as to be complementary to nucleotide sequences flanking the cleavage site in the target RNA. On incubation of the ribozyme or ribozyme composition and its substrate, an enzyme/substrate complex is formed as a result of base pairing between corresponding nucleotides in the ribozyme and the substrate. Nucleotide sequences complementary to $(X)_{n'}$ and $(X)_{n'}$ of the compounds above flanking the cleavage site in the substrate may form a double stranded duplex with $(X)_n$ and $(X)_{n'}$ as a result of base pairing, which base pairing is well known in the art (see for example: Sambrook, 1989, Molecular Cloning, A Laboratory Manual, 2nd Edition, Cold Spring Harbor Press). The formation of a double stranded duplex between the nucleotides may be referred to as hybridization (Sambrook, 1989). The extent of hybridization or duplex formation between the ribozyme and its substrate can be readily assessed, for example, by labelling one or both components, such as with a radiolabel, and then subjecting the reaction mixture to polyacrylamide gel electrophoresis under non-denaturing conditions (Sambrook, 1989). If the target is cleaved specifically on incubation with the compound, the compound is active and falls within the scope of this invention. Accordingly, a ribozyme containing substituted or modified nucleotides in the conserved region may be simply tested for endonuclease activity in a routine manner.

As will be readily appreciated by workers in the field to which this invention relates, the cleavage of a target RNA may be readily assessed by various methods well known in the art (see for example: Sambrook, 1989). Cleavage may, for example, be assessed by running the reaction products (where the substrate is radioactively labelled) on acrylamide, agarose, or other gel systems under denaturing conditions, and then subjecting the gel to autoradiography or other analytical technique to detect cleavage fragments (Sambrook 1989).

The invention is also directed to an oligonucleotide transfer vector containing a nucleotide sequence or sequences which on transcription gives rise to a compound of formula IA or 1B above. The transfer vector may be a bacterial plasmid, a recombinant bacterial plasmid, a bacteriophage DNA, a cosmid, or an eukaryotic viral DNA. The transfer vector may also contain an appropriate transcription promoter sequence such as that for RNA polymerase II, RNA polymerase III, a viral promoter such as SV40 or HIV LTR, a plant promoter such as CaMV S35 or a promoter associated with animal health. The vector may also contain an appropriate termination sequence. Preferably, the plant or animal promoter is capable of expression in a regulated manner. Such promoter control regions would be regulated by endogenous signals to direct either tissue specific or temporal expression, or by externally administered compounds to elicit transcription of downstream sequences. It may also contain sequences to effect integration into the host genome or episomal replication in the host cell.

The invention also provides a host cell transformed by the transfer vector as mentioned above, which may be a prokaryotic host cell or an eukaryotic host cell e.g. a yeast cell or yeast protoplast, *E. coli* host cell, a monkey host cell (e.g. COS), a Chinese hamster ovary host cell, a mammalian host cell, a plant host cell, or a plant protoplast host cell.

In one embodiment, there is provided a packaged oligonucleotide transfer vector, as mentioned hereinabove, which is a plant virus, a composite mammalian virus, a geminivirus, a Ti or Ri plasmid, an infective phage particle or portion thereof.

The nucleotides X in the compounds of formula IA or 1B may be in the form of deoxyribonucleotides, ribonucleotides, deoxyribonucleotide/ribonucleotide hybrids, or derivatives thereof as herein described.

The flanking sequences $(X)_n$ and $(X)_{n'}$ in the compounds of formula IA or 1B may be chosen to optimize stability of the ribozyme from degradation. For example, deoxyribonucleotides are resistant to the action of ribonucleases. Modified bases, sugars or phosphate linkages of nucleotides, such as phosphoramidate or phosphorothioate linkages in the sugar phosphate chain of $(X)_n$ and $(X)_{n'}$ may also provide resistance to nuclease attack. Binding affinity may also be optimized in particular circumstances, by providing nucleotides solely in the form of ribonucleotides, deoxyribonucleotides, or combinations thereof. In some circumstances it may be necessary to optimize the composition of the sequences $(X)_n$ and $(X)_{n'}$ to maximize target RNA cleavage. The cleavage activity of ribozymes having flanking nucleotide sequences which hybridize to target sequences and which are comprised wholly of deoxyribonucleotides may, in some circumstances, have reduced activity. In such circumstances optimization may involve providing a mixture of deoxyribonucleotides and ribonucleotides in the nucleotide sequences $(X)_n$ and $(X)_{n'}$. For example, nucleotides in the ribozyme which are proximal to the cleavage site in a target RNA may be in the form of ribonucleotides.

The respective 3' and 5' termini of the sequences $(X)_n$ and $(X)_{n'}$ or alternatively the 3' and 5' end termini of the ribozyme, may be modified to stabilize the ribozyme from degradation. For example, blocking groups may be added to prevent terminal nuclease attack, in particular 3'-5' progressive exonuclease activity. By way of example, blocking groups may be selected from substituted or unsubstituted alkyl, substituted or unsubstituted phenyl, and substituted or unsubstituted alkanoyl groups. Substituents may be selected from $C_1$–$C_5$ alkyl; halogens such as F, Cl or Br; hydroxy; amino; $C_1$–$C_5$ alkoxy and the like. Alternatively, nucleotide analogues such as phosphorothioates, methylphosphonates or phosphoramidates, or nucleoside derivatives (such as alpha—anomer of the ribose moiety) which are resistant to nuclease attack may be employed as terminal blocking groups. The blocking group may be an inverted linkage such as a 3'3' thymidine linkage or a 5'5' pyrophosphate linkage as in the guanosine cap.

Alternatively, groups which alter the susceptibility of the ribozyme molecule to nucleases may be inserted into the 3' and/or 5' end of the ribozyme. For example, 9-aminoacridine attached to the ribozyme may act as a terminal blocking group to generate resistance to nuclease attack on the ribozyme molecules and/or as an intercalating agent to aid endonucleolytic activity. It will be readily appreciated that a variety of other chemical groups, e.g. spermine or spermidine, could be used in a related manner.

It is also possible to stabilize the ribozyme from degradation by embedding it in an RNA molecule. These molecules can be produced either in vitro or in vivo by DNA coding sequences being operably linked to transcriptional control sequences as appropriate. Examples of RNA molecules into which ribozymes could be inserted may include, but are not limited to, tRNA, mRNA, rRNA, snRNA or other RNA molecules. In addition, the ribozyme may be inserted into an engineered stable stem loop structure. The compound may also be coupled with other stabilizing structures such as a transcription terminator on the 3' end such as the T7 terminator, p-independent terminator, cry element (Gelfand et al. U.S. Pat. No. 4,666,848, issued May 19, 1987) or the TrpE terminator. Furthermore, sequences such as the poly (A) addition signal AAUAAA may be added. In addition, strategies involving changing the length of the 3' noncoding region may be used (see Gillies, U.S. Pat. No. 5,149,635, issued Sep. 22, 1992). Alternatively, a stabilizing sequence or protein binding domain (see PCT International application WO 94/10301) may be used. Further, it is possible to insert the compound into a DNA molecule as well.

The compounds of this invention may be covalently or non-covalently associated with affinity agents such as proteins, steroids, hormones, lipids, nucleic acid sequences, intercalating molecules (such as acridine derivatives, for example 9-amino acridine) or the like to modify binding affinity for a substrate nucleotide sequence or increase affinity for target cells, or localization in cellular compartments or the like. For example, the ribozymes of the present invention may be associated with RNA binding peptides or proteins which may assist in bringing the ribozyme into juxtaposition with a target nucleic acid such that hybridization and cleavage of the target sequence may take place. Nucleotide sequences may be added to the respective 3' and 5' termini of the sequences $(X)_n$ and $(X)_{n'}$ or alternatively the 3' and 5' end termini of the ribozyme to increase affinity for substrates. Such additional nucleotide sequences may form triple helices with target sequences which may enable interaction with an intramolecularly folded substrate. Alternatively, modified bases (for example, non-natural or modified bases as described in Saenger, 1984, Principles of Nucleic Acid Structure, Springer-Verlag N.Y.) within the additional nucleotide sequences may be used that will associate with either single stranded or duplex DNA generating base pair, triplet, or quadruplet, interactions with nucleotides in the substrate. Suitable bases would include inosine, 5-methylcytosine, 5-bromouracil and other such bases as are well known in the art, as described, for example, in Saenger, 1984.

The compounds of this invention may be produced by oligonucleotide synthetic techniques which are known in the art. Generally, such synthetic procedures involve the sequential coupling of activated and protected nucleotide bases to give a protected nucleotide chain, whereafter protecting groups may be removed by suitable treatment. Preferably the compounds will be synthesized on an automated synthesizer such as those made by Applied Biosystems (a Division of Perkin Elmer), Pharmacia or Millipore. Alternatively, the ribozymes in accordance with this invention may be produced by transcription of nucleotide sequences encoding said ribozymes in host-cells or in cell free systems utilizing enzymes such as T3, SP6 or T7 RNA-polymerase.

In addition to being synthesized chemically, ribozymes with modified nucleotides may be synthesized enzymatically. The phosphodiester bonds of RNA can be replaced by phosphorothioate linkages by in vitro transcription using nucleoside α-phosphorothiotriphosphates. T7 RNA polymerase specifically incorporates the Sp isomer of α-phosphorothiotriphosphate with inversion of configuration to produce the Rp isomer of the phosphorothioate linkage. Similarly, T7 RNA polymerase is also able to incorporate 2' O modified nucleotide triphosphates, including 2' O-methyl, 2' O-fluoro and 2' amino modified nucleoside triphosphates.

Nucleotides represented in the compounds for formula I above comprise a sugar, base, and a monophosphate group or a phosphodiester linkage. Accordingly, nucleotide derivatives or modifications may be made at the level of the sugar, base, monophosphate groupings or phosphodiester linkages. It is preferred that the nucleotides in the compounds above be ribonucleotides or RNA/DNA hybrids, however, other substitutions or modifications in the nucleotide are possible providing that endonuclease activity is not lost.

In one aspect of this invention, the sugar of the nucleotide may be a ribose or a deoxyribose such that the nucleotide is either a ribonucleotide or a deoxyribonucleotide, respectively. Furthermore, the sugar moiety of the nucleotide may be modified according to well known methods in the art (see for example: Saenger, 1984) This invention embraces various modifications to the sugar moiety of nucleotides as long as such modifications do not abolish cleavage activity of the ribozyme. Examples of modified sugars include replacement of secondary hydroxyl groups with halogen, amino or azido groups; 2'-alkylation; conformational variants such as the 2'-hydroxyl being cis-oriented to the glycosyl $C_1$-N link to provide arabino-nucleosides, and conformational isomers at carbon $C_1$ to give alpha-nucleosides, and the like. In addition, the invention is directed to compounds with a substituted 2'-hydroxyl, such as 2' O-allyl or 2' O-methyl. Alternatively, the carbon backbone of the sugar may be substituted, such as in 2' C-allyl.

Accordingly, the base of the nucleotide may be adenine, 2-amino adenine, cytosine, guanine, hypoxanthine, inosine, methyl cytosine, thymine, xanthine, uracil, or other modified bases.

Nucleotide bases, deoxynucleotide bases, and ribonucleotide bases are well known in the art and are described, for example in Saenger, (1984). Furthermore, nucleotide, ribonucleotide, and deoxyribonucleotide derivatives, substitutions and/or modifications are well known in the art (see for example: Saenger, 1984); and these may be incorporated in the ribozyme made with the proviso that endonuclease activity of the ribozyme is not lost. As mentioned previously, endoribonuclease activity may be readily and routinely assessed.

In addition, a large number of modified bases are found in nature, and a wide range of modified bases have been synthetically produced (see for example: Saenger, 1984). For example, amino groups and ring nitrogens may be alkylated, such as alkylation of ring nitrogen atoms or carbon atoms such as $N_1$ and $N_7$ of guanine and $C_5$ of cytosine; substitution of keto by thioketo groups; saturation of carbon-carbon double bonds, and introduction of a C-glycosyl link in pseudouridine. Examples of thioketo derivatives are 6-mercaptopurine and 6-mercaptoguanine. Bases may be substituted with various groups, such as halogen, hydroxy, amine, alkyl, azido, nitro, phenyl and the like.

The phosphate moiety of nucleotides or the phosphodiester linkages of oligonucleotides are also subject to derivatization or modifications, which are well known in the art. For example, replacement of oxygen with nitrogen, sulphur or carbon gives phosphoramidates, phosphorothioates or phosphorodithioates, and phosphonates, respectively. Substitutions of oxygen with nitrogen, sulphur or carbon derivatives may be made in bridging or non bridging positions. It has been well established from work involving antisense oligonucleotides that phosphodiester and phosphorothioate derivatives may efficiently enter cells (particularly when of short length), possibly due to association with a cellular receptor. Methylphosphonates are readily taken up by cells probably by virtue of the electrical neutrality.

A further aspect of the invention provides alternative linkages such as an amide, a sulfonamide, a hydroxylamine, a formacetal, a 3'-thioformacetal, a sulfide, or an ethylene glycol function to replace the conventional phosphodiester linkage. These modifications may increase resistance towards cellular nucleases and/or improve pharmacokinetics.

Detailed information on synthesis of protected nucleotides and their incorporation into modified ribozymes is provided in International Patent Application No. PCT/AU96/00343 (WO 96/40806), the contents of which are incorporated by reference into the present application.

Possible nucleotide modifications include the following, by way of example:

Sugar modifications may be 2' fluoro, 2' amino, 2' O-allyl, 2' C-allyl, 2' O-methyl, 2' O-alkyl, 4'-thio-ribose, α-anomer, arabinose, other sugars, or non-circular analogues.

Phosphate modifications may be phosphorothioate (non-bridging), phosphorodithioate (non-bridging), 3' bridging phosphorothioate, 5' bridging phosphorothioate, phosphoramidate, 3' bridging phosphoramidate, 5' bridging phosphoramidate, methyl phosphonate, other alky/phosphonates or phosphate triesters The phosphodiester linkage may be replaced by an amide, carbamate, thiocarbamate, urea, amine, hydroxylamine, formacetal, thioformacetal, allyl ether, allyl, ether, or thioether linkage. Alternatively, the phosphodiester linkage and the ribose may be replaced by the amide backbone in a PNA (peptide nucleic acid) linkage.

Base modifications may be purine, 2,6-diaminopurine, 2-aminopurine, $O^6$-methylguanosine, C-5-alkenylpyrimidine derivatives, C-5-propynylpyrmidine derivatives, inosine, 5-methylcytosine, pseudouridine, abasic (ribose or deoxyribose).

Some nucleotides may be replaced with the following chemical linkers: 1,3-propane-diol, alkane-diols, or various polymers of ethyleneglycol, tetraethylene glycol or hexaethyleneglycol.

Other modifications to the 3' end may be selected from: 3'-3' inverted linkage (inverted nucleotide or inverted abasic nucleotide), 3'-3' linked abasic ribose, or end-capped (methoxyethylamine phosphoramidate).

International Patent Application No. PCT/AU96/00343 sets out in detail methods by which these modified nucleotides may be synthesised, as well as nucleotide modifications which have been tested in ribozymes.

Any combination of the above listed nucleotide modifications, substitutions, or derivatizations, made at the level of the sugar, base, monophosphate groupings or phosphodiester linkages, may be made in the compounds of the present invention provided that endonuclease activity is not lost.

The compounds of this invention may be incorporated and expressed in cells as a part of a DNA or RNA transfer vector, or a combination thereof, for the maintenance, replication and transcription of the ribozyme sequences of this invention.

Nucleotide sequences encoding the compounds of this invention may be integrated into the genome of a eukaryotic or prokaryotic host cell for subsequent expression (for example as described by Sambrook, 1989). Genomic integration may be facilitated by transfer vectors which integrate into the host genome. Such vectors may include nucleotide sequences, for example of viral or regulatory origin, which facilitate genomic integration. Methods for the insertion of nucleotide sequences into host genome are described for example in Shambrook et al. (1989).

Nucleic acid sequences encoding the ribozymes of this invention and integrated into the genome of a host cell preferably include promoter and enhancer elements operably linked to the nucleotide sequence encoding the ribozyme of this invention, together with an appropriate termination sequence, so as to be capable of expressing said ribozyme in a eukaryotic (such as animal or plant) or prokaryotic (such as bacteria) host cell. Ideally, the promoter and enhancer elements are designed for expression in a tissue and/or developmentally specific manner.

Additionally, the compounds of the present invention may be prepared by methods known per se in the art for the synthesis of RNA molecules, (for example, according to recommended protocols of Promega, Madison, Wis., USA). In particular, the ribozymes of the invention may be prepared from a corresponding DNA sequence (DNA which on transcription yields a ribozyme, and which may be synthesized according to methods known per se in the art for the synthesis of DNA) operably linked to an RNA polymerase promoter such as a promoter for T3 or T7 polymerase or SP6 RNA polymerase. A DNA sequence corresponding to a ribozyme of the present invention may be ligated into a DNA transfer vector, such as plasmid or bacteriophage DNA. Where the transfer vector contains an RNA polymerase promoter operably linked to DNA corresponding to a ribozyme, the ribozyme may be conveniently produced upon incubation with an RNA polymerase. Ribozymes may, therefore, be produced in vitro by incubation of RNA polymerase with an RNA polymerase promoter operably linked to DNA encoding a ribozyme, in the presence of ribonucleotides and an appropriate buffer. In vivo, prokaryotic or eukaryotic cells (including mammalian, plant and yeast cells) may be transfected with an appropriate transfer vector containing genetic material encoding a ribozyme in accordance with the present invention, operably linked to an RNA polymerase promoter such that the ribozyme is transcribed in the host cell. Transfer vectors may be bacterial plasmids or viral (RNA and DNA) or portion thereof. Nucleotide sequences corresponding to ribozymes are generally placed under the control of strong promoters such as the lac, SV40 late, SV40 early, metallothionein, or lambda promoters. Particularly useful are promoters regulated in a tissue or a temporal (developmental) specific manner, or a tightly regulated inducible promoter suitable for gene therapy, which may be under the control of exogenous chemicals. The vector may be an adenovirus or an adeno-associated virus (see for example PCT International Publication No. WO 93/03769, "Adenovirus Mediated Transfer of Genes to the Gastrointestinal Tract", PCT International Publication No. WO 94/11506, "Adenovirus-Mediated Gene Transfer to Cardiac and Vascular Smooth Muscle," PCT International Publication No. WO 94/11522, "Vector for the Expression of Therapy-Relevant Genes," PCT International Publication No. WO 94/11524, "Targetable Vector Particles," PCT International Publication No. WO 94/17832, "Targeting and Delivery of Genes and Antiviral Agents into Cells by the Adenovirus Penton"). Ribozymes may be directly transcribed in vivo from a transfer vector, or alternatively, may be transcribed as part of a larger RNA molecule. For example, DNA corresponding to ribozyme sequences may be ligated into the 3' end of a reporter gene, for example, after a translation stop signal. Larger RNA molecules may help to stabilize the ribozyme molecules against nuclease digestion within cells. On translation, the reporter gene may give rise to a protein, possibly an enzyme whose presence can be directly assayed.

The compounds of this invention may be involved in gene therapy techniques where, for example, cells from a human suffering from a disease, such as HIV, are removed from a patient, treated with the ribozyme or transfer vector encoding the ribozyme to inactivate the infectious agent, and then returned to the patient to repopulate a target site with resistant cells, so called ex vivo therapy. Such cells would be resistant to HIV infection and the progeny thereof would also confer such resistance. In the case of HIV, nucleotide sequences encoding ribozymes of this invention capable of inactivating the HIV virus may be integrated into the genome of lymphocytes or may be expressed by a non-integrating vector such as adenovirus. Alternatively, the nucleotide sequences-may be expressed by a retrovirus or modified retrovirus known for use in the treatment of HIV.

A transfer vector such as a bacterial plasmid or viral RNA or DNA or portion thereof, encoding one or more of the compounds of this invention, may be transfected into cells of an organism in vivo. Once inside the cell, the transfer vector in some cases may replicate and be transcribed by cellular polymerases to produce ribozyme RNAs which may have ribozyme sequences of this invention; the ribozyme RNAs produced may then inactivate a desired target RNA. Alternatively, a transfer vector containing one or more ribozyme sequences may be transfected into cells by electroporation, PEG, high velocity particle bombardment or lipofectants, or introduced into cells by way of micro-manipulation techniques such as microinjection, such that the transfer vector or a part thereof becomes integrated into the genome of the host cell. Transcription of the integrated genetic material gives rise to ribozymes, which act to inactivate a desired target RNA. Transfer vectors expressing ribozymes of this invention may be capable of replication in a host cell for stable expression of ribozyme sequences. Alternatively, transfer vectors encoding ribozyme sequences of this invention may be incapable of replication in host cells, and thus may result in transient expression of ribozyme sequences. Methods for the production of DNA and RNA transfer vectors, such as plasmids and viral constructs are well known in the art and are described for example by Sambrook et al. (1989).

Transfer vectors would generally comprise the nucleotide sequence encoding the ribozyme of this invention, operably linked to a promoter and other regulatory sequences required for expression and optionally replication in prokaryotic and/or eukaryotic cells. Suitable promoters and regulatory sequences for transfer vector maintenance and expression in plant, animal, bacterial, and other cell types are well known in the art.

The ribozymes of the present invention have extensive therapeutic and biological applications. For example, disease-causing viruses in man and animals may be inactivated by administering to a subject infected with a virus, a ribozyme in accordance with the present invention adapted to hybridize to and cleave specific RNA transcripts of the virus. Such ribozymes may be delivered by parenteral or other means of administration. Alternatively, a subject infected with a disease causing virus may be administered a non-virulent virus such as vaccinia or adenovirus which has been genetically engineered to contain DNA corresponding to a ribozyme operably linked to an RNA promoter, such that the ribozyme is transcribed in the cells of the host animal, transfected with the engineered virus, to effect cleavage and/or inactivation of the target RNA transcript of the disease causing virus.

The ribozymes of the present invention have particular application to viral diseases caused for example, by the herpes simplex virus (HSV) or the AIDS virus (HIV). Further examples of human and animal disease which may be treated with the ribozymes of this invention include human disorders such as inflammatory diseases (e.g. arthritis) and circulatory disorders (e.g. artheroscierosis and restenosis), psoriasis, cervical preneoplasia, papilloma disease, bacterial and prokaryotic infection, viral infection and neoplastic conditions associated with the production of aberrant RNAs such as occurs in chronic myeloid leukemia. Diseases or infections which may be treated in plants with ribozymes of this invention include fungal infection, bacterial infections (such as Crown-Gall disease) and disease associated with plant viral infection. Of particular interest would be compounds targeting genes associated with male gametophyte development, (examples include PCT International Publication No. WO 92/18625, entitled "Male-Sterile Plants, Method For Obtaining Male-Sterile Plants And Recombinant DNA For Use Therein"; U.S. Pat. No. 5,254, 802, entitled "Male Sterile Brassica Plants";PCT international Publication No. WO 93/25695, entitled "Maintenance of Male-Sterile Plants";PCT International Publication No. WO 94/25593, entitled "Method For Obtaining Male-Sterile Plants; PCT International Publication No. WO 94/29465, entitled "Process For Generating Male Sterile Plants").

The period of treatment would depend on the particular disease being treated and could be readily determined by a physician or by a plant biologist as appropriate. Generally treatment would continue until the disease being treated was ameliorated.

The ribozymes of the present invention also have particular application to the inactivation of RNA transcripts in bacteria and other prokaryotic cells, plants, animals and yeast cells. In bacteria, RNA transcripts of, for example, bacteriophage (which cause bacterial cell death) may be inactivated by transfecting a cell with a DNA transfer vector which is capable of producing a ribozyme in accordance with the present invention which inactivates the phage RNA. Alternatively, the ribozyme itself may be added to and taken up by the bacterial cell to effect cleavage of the phage RNA. Similarly, eukaryotic and prokaryotic cells in culture may, for example, be protected from infection or disease associated with mycoplasma infection, phage infection, fungal infection and the like.

RNA transcripts in plants may be inactivated using ribozymes encoded by a transfer vector such as the Ti plasmid of *Agrobacterium tumefaciens*. When such vectors are transfected into a plant cell and integrated, the ribozymes are produced under the action of RNA polymerase and may effect cleavage of a specific target RNA sequence. Endogenous gene transcripts in plant, animal or other cell types may be inactivated using the compounds of the present invention. Accordingly, undesirable phenotypes or characteristics may be modulated. It may, for example, be possible using the ribozymes of the present invention to remove stones from fruit or treat diseases in humans which are caused by the production of a deleterious protein, or overproduction of a particular protein. The compounds described above may be used to effect male sterility by destroying the pollen production in a plant. Furthermore, for the in vivo applications of the ribozymes of this invention in humans, animals, plants, and eukaryotic and prokaryotic cells, such as in phenotypic modification and the treatment of disease, it is necessary to introduce the ribozyme into cells whereafter, cleavage of target RNAs takes place. In vivo applications are highly suitable to the compounds as discussed herein. Methods for the introduction of RNA and DNA sequences into cells, and the expression of the same in prokaryotic and eukaryotic cells are well known in the art. The same widely known methods may be utilized in the present invention.

The compounds of this invention may be incorporated into cells by direct cellular uptake, where the ribozymes of this invention would cross the cell membrane or cell wall from the extracellular environment. Agents may be employed to enhance cellular uptake, such as liposomes or lipophilic vehicles, cell permeability agents, such as dimethylsulfoxide, and the like.

The compounds of the present invention may be combined with pharmaceutically and veterinarally acceptable carriers and excipients which are well known in the art, and include carriers such as water, saline, dextrose and various sugar solutions, fatty acids, liposomes, oils, skin penetrating agents, gel forming agents and the like, as described for example in Remington's Pharmaceutical Sciences, 17th Edition, Mack Publishing Co., Easton, Pa., which is incorporated herein by reference.

Agriculturally acceptable carriers and excipients are well known in the art and include water; surfactants; detergents; particularly biodegradable detergents; talc; inorganic and/or organic nutrient solutions; mineral earths and clays; calcium carbonate; gypsum; calcium sulfate; fertilizers such as ammonium sulfate, ammonium phosphate, urea, carborundum, and *Agrobacterium tumefaciens*; and natural products of vegetable origin such as, for example, grain, meals and flours, bark meals; and the like.

The compounds of this invention may be provided in a composition with one or more anti-viral, anti-fungal, anti-bacterial, anti-parasitic, anti-protozoan or anthelminthic agents, herbicides, pesticides or the like, for example as described in the Merck Index (1989) 11th Edition, Merck & Co. Inc.

By way of example only, therapeutic compositions of this invention may be directed against Herpes Simplex virus types 1 and 2, psoriasis, cervical preneoplasia, papilloma disease, and bacterial and prokaryotic infection. Such treatments may, for example, involve topical application of ribozyme to the site of disease. For example, in the treatment of Herpes virus lesions, ribozymes may be formulated into a cream containing a concentration of 0.1 nM to 100 mM ribozyme, preferably 1 nM to 1 mM. The cream may then be applied to the site of infection over a 1 to 14 day period in order to cause amelioration of symptoms of the infection. Prior to the final development of topical formulations for the treatment of virus infection, effectiveness and toxicity of the ribozymes and formulations involving them may, for example, be tested on an animal model, such as scarified mouse ear, to which virus particles, such as $2 \times 10^6$ plaque forming units are added. A titer of infectious virus particles in the ear after treatment can then be determined to investigate effectiveness of treatment, amount of ribozyme required and like considerations. Similar investigations in animal models prior to human trials may also be conducted, for example, in respect of the treatment of psoriasis, papilloma disease, cervical preneoplasia, and in diseases such as HIV infection, bacterial or prokaryotic infection, viral infection and various neoplastic conditions which involve a deleterious RNA species.

Compositions for topical application are generally in the form of creams, where the ribozymes of this invention may be mixed with viscous components. The compounds of this invention may be incorporated into liposomes or other barrier type preparations to shield the ribozymes from nuclease attack or other degradative agents (such as nucleases and adverse environmental conditions such as UV light).

Compositions may be provided as unit dosages, such as capsules (for example gelatin capsules), tablets, suppositories and the like. Injectable compositions may be in the form of sterile solutions of ribozyme in saline, dextrose or other media. Compositions for oral administration may be in the form of suspensions, solutions, syrups, capsules, tablets and the like. Ribozymes may also be provided in the form of an article for sustained release, impregnated bandages, patches and the like. The compounds of this invention may be embedded in liposomes or biodegradable polymers such as polylactic acid. Pharmaceutical compositions which may be used in this invention are described, for example, in Remington's Pharmaceutical Sciences, see above.

The present invention is further directed to a plant DNA expression cassette comprising a gene sequence flanked by promoter and terminator sequences at its 5' and 3' ends respectively wherein said genetic sequence on expression provides a ribozyme RNA. The DNA cassette may further be part of a DNA transfer vector suitable for transferring the DNA cassette into a plant cell and insertion into a plant genome. In a most preferred embodiment of the present invention, the DNA cassette is carried by broad host range plasmid which is capable of transformation into plant cells using Agrobacterium comprising Ti DNA on the left and right borders, a selectable marker for prokaryotes, a selectable marker for eukaryotes, a bacterial origin of replication and optional plant promoters and terminators. The present invention also includes other means of transfer such as genetic bullets (e.g. DNA-coated tungsten particles, high-velocity micro projectile bombardment) and electroporation amongst others.

The present invention is also directed to a transgenic plant resistant to a virus, its genome containing a sequence which gives rise, on transcription, to the nucleic acid molecule mentioned above. This transgenic plant, including fruits, and seeds thereof, may be from alfalfa, apple, arabidopsis, barley, bean, canola (oilseed rape), cantaloupe, carnation, cassava, casuarina, clover, corn, cotton, courgette, cucumber, eucalyptus, grape, melon, papaya, pepper, potato, rice, rose, snap dragon, soybean, squash, strawberry, sunflower, sweet pepper, tobacco, tomato, walnut, wheat or zucchini. Also included are the plant cells transformed by the above-mentioned transfer vector comprising a nucleotide sequence which is, or on transcription gives rise to, the nucleic acid molecule.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

Further features of the present invention are more fully described in the following Example(s). It is to be understood, however, that this detailed description is included solely for the purposes of exemplifying the present invention, and should not be understood in any way as a restriction on the broad description of the invention as set out above.

BRIEF DESCRIPTION OF THE FIGURES

FIG. 2. (a) Scheme for in vitro selection. The transcribed random pool RNA was directed in trans against a 29 mer synthetic RNA substrate (IL2bioS) comprising a 13 nt segment of human IL2 mRNA. Annealed duplexes were immobilised to an MPG-avidin solid phase via a 3' substrate biotin. Unbound material was removed and active structures were eluted by adding $MgCl_2$. Molecules capable of supporting $Mg^{2+}$ dependent cleavage became selectively disassociated from the solid phase due to reduced helical stability (ie. 'm helix I<'m helix I+III; 'm is melting temperature). (b) Shows IL2bioS (substrate) and random (N18) RNA, in trans. (c) Shows the structure of the N4 random population. The selected fraction was amplified (RT-PCR) using primers P1/P2 (N18) and P1/P3 (N4). P2 and P3 encoded T7 promoters, enabling transcription of the subsequent generation.

FIG. 4. Sequence alignment showing composition of the N18 domain in the selected populations. Variable regions are highlighted. (a) Shows a sampling of the cloned fraction of the g4 population and indicates the state of enrichment after 4 rounds of low stringency selection. Linker positions are numbered 10.1, L.1–L.4, and 11.1 (SEQ ID NOS. :77–107) (b). The sampled fraction of the g6 populations showing the impact of high stringency selection on the identity of the variable (linker) region (position 10.1–11.1 inclusive). (SEQ ID NOS.: 108–153)

FIG. 6. Sequence data acquired from the N4g3 population. All sequences correspond to the derivation; 5' NNHH (linker positions L.1–L.4). Three classes of molecule can be identified; YRHH, WYHH, GHHA (Y=C/U; R=G/A; W=A/U; H=A/U/C). Numbers after sequences indicate the incidence of that particular motif in N4g3. A highly represented pyrimidine rich subset (UUHH) of class II was identified.

EXAMPLE

Figure 1:
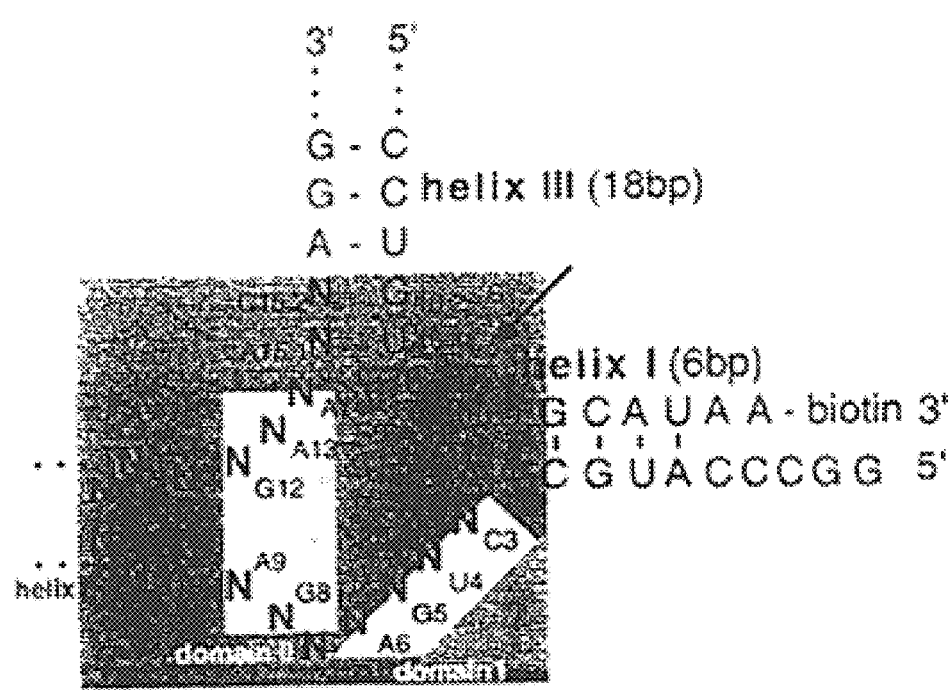
FIG. 1. N18g0 RNA (SEQ ID NO:75) plus substrate showing construction of the size constrained random (N=18) domain. The diversity of g0 was $4^{18}$ ($6.9 \times 10^{10}$). The design is a bimolecular configuration analogous to that proposed by Haseloff and Gerlach (13), comprising two antisense regions separated by a metal dependent. catalytic domain. Helix I and III were formed by association with a biotinylated RNA substrate (SEQ ID NO:76) (IL2bioS). Helix III is not shown in full. Notation on the random positions indicates correspondent nucleotide base identity and positions for the hammerhead (53). In the hammerhead, helix II is an extended RNA hairpin comprising 3-6 Watson-Crick base pairs. The Enzyme strand (E) promotes 2'-O mediated cleavage of the substrate strand (S) immediately 3' to C17 (indicated by arrow.

In vitro selection was used to enrich for highly efficient RNA phosphodiesterases within a size constrained (18 nt) ribonucleotide domain. The starting population (g0) was directed in trans against an RNA oligonucleotide substrate immobilised to an avidin-magnetic phase. 4 rounds of selection were conducted using 20 mM Mg$^{2+}$ to fractionate the population on the basis of divalent metal ion dependent phosphodiesterase activity. The resulting generation 4 (g4) RNA was then directed through a further 2 rounds of selection using low concentrations of Mg$^{2+}$. Generation 6 (g6) was composed of sets of active, trans cleaving minimised ribozymes, containing recognised hammerhead motifs in the conserved nucleotides, but with highly variable linker domains (loop II-L.1–L.4). Cleavage rate constants in the g6 population ranged from 0.004–1.4 min$^{-1}$ at 1 mM Mg$^{2+}$ (pH 8.0, 37° C.). Selection was further used to define conserved positions between G(10.1) and C(11.1) required for high cleavage activity at low Mg$^{2+}$ concentration. The kinetic phenotype of these molecules was superior to a hammerhead ribozyme with 4 bp in helix II. At low Mg$^{2+}$ concentration, the disparity in cleavage rate constants increases in favour of the minimised ribozymes. Favourable kinetic traits appeared to be a general property for specific selected linker sequences, as the observation of high rates of catalysis were transferable to a different substrate system.

Materials and Methods

Oligonucleotides Oligonucleotides were synthesised on an Applied Biosystems model 394 DNA synthesiser. DNA Phosphoramidite monomers were supplied by PE-Applied Biosystems. RNA phosphoramidites were from Glen Research (Sterling, Virginia). Deprotection and purification was as described previously (25,27). Gel purified oligonucleotides were resuspended in sterile, autoclaved H$_2$O. Concentrations were determined by UV spectroscopy and samples were stored at −20° C. Zero generation (g0) RNA was transcribed in vitro from a synthetic DNA template (N18g0T) containing a T3 promoter sequence. (lower case= deoxyribonucleotide; upper case=ribonucleotide). N18g0T 65 mer DNA; 5' ctc ggt acc gtt gat cct (n18) ftg cat tgg gcc ttt agt gag ggt taa ft, (SEQ ID NO:3) (minus strand) T3 promoter underlined. RNA substrate (IL2bioS) was produced directly by solid phase synthesis. Biotin was incorporated using 3' BioTEG phosphoramidite (12 carbon linker) supplied by Auspep (Melbourne, Australia). IL2bioS 29 mer RNA; 5' CUC GGU ACC GUU GAU CCU GUC UUG CAU M-biotin 3' (SEQ ID NO:4) (putative cleavage triplet underlined). N4g0T 66 mer 5' ctc ggt acc gtt gat cct gtt tcg (n4) ctc atc agt tgc aft ggg <u>ccc tat agt gag tcgtat ta,</u> (SEQ ID NO:5), N5g0T 67-mer ctc ggt acc gtt gat cct gft tcg (n5) ctc atc agt tgc att ggg <u>ccc tat agt gag tcg tat ta,</u> (SEQ ID NO:6) (minus strand) T7 promoter underlined. Primers used were; T3 15 mer 5' aat taa ccc tca cta (SEQ ID NO:7); P1 17 mer 5' ctc ggt acc gtt gat cc (SEQ ID NO:8); P2 38 mer 5' gag gga tcc <u>taa tac gac tcacta tag gcc</u> caa tgc aa (SEQ ID NO:9); P3 40 mer 5' gag gga tcc <u>taa tac gac tca cta tag</u> ggc cca atg caac (SEQ ID NO:10), T7 promoters (plus strand) underlined. A number of substrates, plus ribozymes with full length helix II, and ribozymes with evolved linkers, were produced by solid phase synthesis to test the comparative efficacy of the evolved miniribozymes versus conventional hammerhead ribozymes in different substrate backgrounds. These were; KrS17 5' UUG CGA <u>GUC</u> CAC ACU Gg (SEQ ID NO:11)(17 mer substrate); IL2S19 5' AAC UCC U <u>GU C</u>UU GCA UUGc(SEQ ID NO:12) (19 mer substrate); IL2S15 UCC U<u>GU C</u>UU GCA UUg (SEQ ID NO:13) (15 mer substrate); KrMc10 5' UCC AGU GUG CUG AUG AGG UM CGA MC UCG CAAa (SEQ ID NO:14) (34 mer miniribozyme); KrRz 5' CUC CAG UGU GCU GAU GAG UCC UUU UGG ACG AM CUC GCA Mt (SEQ ID NO:15) (42 mer ribozyme); IL2Mc10 5' GCA AUG CM CUG AUG AGG UM CGA MC AGG AGUt (SEQ ID NO:16) (34 mer miniribozyme); IL2Rz 5' GCA AUG CM CUG AUG AGU CCU UUU GGA CGA MC AGG AGUt (SEQ ID NO:17) (40 mer ribozyme). PDGF293 MR1 5' CAG CUU CCU C CUGAUGA GGUMC GAAAU GCU UCU Ct (SEQ ID NO:18) (36-mer miniribozyme); PDGF293 MR2 5' CAG CUU CCU C CUGAUGA ggtaac GAAAU GCU UCU Ct (SEQ ID NO:19) (36-mer miniribozyme); PDGF293 MR3 5' cag ctt cot c CUGAUGA ggtaac GAAAU gct tct ct (SEQ ID NO:20) (36-mer miniribozyme); PDGF293 MR4 5' cag ctt cct c CUGAUGA GgUaAc GAAAU GCU UCU Ct (SEQ ID NO:21) (36-mer miniribozyme); PDGF293 MR5 5' CAG CUU CCU C CUGAUGA Gg(mU)aA(fC) GAAAU GCU UCU Ct (SEQ ID NO:22) (36-mer miniribozyme); PDGF293 MR6 5' (mC)AG (mC)(mU)(mU) (mC)(mC) (mU) (mC) (mC)UpsGA(mU)GA ggtaac GAAA(mU) G(mC)(mU) (mU)(mC)(mU) (mC)tpstpst (SEQ ID NO:23) (38-mer miniribozyme); PDGF293 MR7 5' (mU)(mU) (mC) (mC)(mU) (mC) (mC)UpsGA(mU)GA ggtaac GAAA(mU) G(mC)(mU) t (SEQ ID NO:24) (28-mer miniribozyme); PDGF293 MR8 5' G (mC)(mU)(mU) (mC)(mC)(mU) (mC) (mC)UpsGA(mU)GA ggtaac GAAA(mU) G(mC)(mU) (mU)(mC)t (SEQ ID NO:25) (32-mer miniribozyme); PDGF293 MR9 5' (mC)AG (mC)(mU)(mU) (mC)(mC) (mU) (mC) (mC)UpsGA(mU)GA ggtaac GAAA(mU) G(mC)(mU) (mU)(mC)(mU) (mC)t (SEQ ID NO:26) (36-mer miniribozyme); PDGF293 MR10 5' GA (mC)AG (mC) (mU)(mU) (mC)(mC)(mU) (mC) (mC)UpsGA(mU)GA ggtaac GAAA(mU) G(mC)(mU) (mU)(mC)(mU) (mC) (mU)(mU)c (SEQ ID NO: 27) (40-mer miniribozyme); PDGF293 MR11 5' GGGA (mC)AG (mC)(mU)(mU) (mC) (mC)(mU) (mC) (mC)UpsGA(mU)GA ggtaac GAAA(mU) G(mC)(mU) (mU)(mC)(mU) (mC)(mU) (mU) (mC)(mC)t (SEQ ID NO:28) (44-mer miniribozyme); PDGF293 MR12 5' (mC)AG (mC)(mU)(mU) (mC)(mC)(mU) (mC) (mC) UpsGA(mU)GA GG(mU)M(mC) GMA(mU) G(mC)(mU)

(mU)(mC)(mU) (mC)t (SEQ ID NO:29) (36-mer miniribozyme); PDGF293 MR13 5' (mC)AG (mC)(mU)(mU) (mC)(mC)(mU) (mC) (mC)UpsGA(mU)GA ggtaac GAGA(mU) G(mC)(mU) (mU)(mC)(mU) (mC)t (SEQ ID NO:30) (36-mer inactive miniribozyme); PDGF S25 5' AGG MG AGA AGC AUC GAG GAA GCU g 3' (SEQ ID NO:31); PDGF293 Antisense (all linkages are phosphorothioate) 5' agc ttc ctc gat gct tct c 3' (SEQ ID NO:32).

Abbreviations: Upper case letters are RNA; Lower case letters are DNA; mU=2' O-methyl uridine; mC=2' O-methyl cytidine; fC=2' fluorocytidine; ps=phosphorothioate linkage (where not otherwise indicated phosphate diesfer linkages are assumed).

Transcription An optimal transcription reaction contained; 0.3–1.0 μM template, 40 mM Tris-HCl pH 8.0, 12–25 mM MgCl$_2$, 2 mM spermidine, 10 mM DTT, 50 μg/μl BSA, 0.01% v/v triton-X 100, 5 mM of each NTP (Boehringer Mannheim), and 20 U/μl T3 RNA polymerase (Promega) or 10 U/μl T7 RNA polymerase (New England Biolabs). Reactions were incubated at 37° C. To generate labelled ($^{32}$P) sample, UTP was reduced to 0.4 mM, and α$^{32}$P UTP (DuPont) was added to 1.0 μCi/μl. N18g0 templates were prepared for transcription by annealing 65 pmoles N18g0T (65 mer) with an excess (75 pmoles) of T3 primer (15 mer) and extending with 2 units of Kienow enzyme (Boehringer Mannheim) using standard conditions, followed by phenol/chloroform extraction and ethanol precipitation. N4g0 template was prepared by annealing 400 pmoles of N4g0T with 800 pmoles of P3. Subsequent generation RNA was transcribed from PCR products with primer incorporated T7 promoters (P2 for N18, and P3 for N4). All transcribed ribozymes were purified by Sephadex G-50 (Pharmacia) chromatography, followed by phenol/chloroform extraction and ethanol precipitation. Purified RNA was dissolved in H$_2$O and stored at −20° C.

N18 selection Pool RNA (50 pmoles) and IL2bioS substrate (25 pmoles) were annealed in 1 mM EDTA/50 mM Tris-HCl (pH 8.0, 37° C.) by heating to 85° C. for 2 minutes and cooling slowly to room temperature (to promote duplex formation). The annealing reaction was incubated in 100 μl 1 M NaCl/1 mM EDTA/50 mM Tris-HCl (pH 8.0 37° C.) for 15 minutes at room temperature with 200 μg avidin paramagnetic porous glass (MPG-Avidin) CPG Inc. (Lincoln Park, N.J.). Excess ribozyme was used to prevent the binding of free substrate. The solid magnetic phase was captured and the supernatant containing the unbound material was removed. Bound material was equilibrated using 3 washes at 40° C. and 3 washes at 25° C. (80 μl 1 M NaCl/1 mM EDTA/50 mM Tris-HCl, pH 8.0). This was followed by a 15 minute incubation in 80 μl 1 M NaCl/1 mM EDTA/50 mM Tris-HCl (pH 8.0) at 37° C. Supernatant from this treatment provided a negative control (negative selection) which was used to establish a base line for calculating the noise/signal ratio (background/cleavage product) in the selected fraction. Positive selection was initiated by resuspending the solid phase in 80 μl 1 M NaCl/50 mM Tris-HCl (pH 8.0, 37° C.), supplemented with 20 mM MgCl$_2$ (g0–g4), or 1–4 mM MgCl$_2$ (g5–g6). Incubation in the selection buffer was for 15 minutes (g0–g4), or 1 minute (g5–g6).

N4 selection N4 pool RNA (300 pmoles) and IL2bioS (150 pmoles) were annealed in 50 mM Tris-HCl/1 mM EDTA, pH 7.6, and bound to 400 μg MPG-Avidin. The selection protocol was as described for N18 above. High concentrations of pool RNA and IL2bioS were used to eliminate the effect of possible contamination from N18g4 or g6. Binding and wash buffer was 100 mM NaCl/100 mM KCl/50 mM Tris-HCl/0.2 mM EDTA, pH 7.6. Selection buffer was 1 mM MgCl$_2$ /100 mM NaCl/100 mM KCl/50 mM Tris-HCl, pH 7.6. A total of five rounds of selection were conducted, with 1 minute incubation at 37° C.

N5 selection N5 pool RNA was selected and amplified for five rounds using the same protocol and conditions as described above for the N4 population.

Amplification and cloning The supernatant representing selected RNA was ethanol precipitated in the presence of a glycogen carrier (Sigma). Precipitated RNA was dissolved in 10 μl H$_2$O and reverse transcribed with a large excess of P1 (100 pmoles). Reverse transcription (RT) reactions contained 1 U/μl AMV reverse transcriptase (Boehringer Mannheim), 1×RT buffer (Boehringer Mannheim), 2 mM of each dNTP (Promega), and 0.5 U/μl RNAsin (Promega) in a 20 μl final volume. The RT reaction was incubated for 15 minutes at 37° C. 0.5 μl of the RT product was used directly for PCR. Thermal cycling was performed using a Corbett Research FTS-1 thermal sequencer (Corbett Industries, Sydney). Reactions contained 0.01 U/μl Taq DNA polymerase (Boehringer Mannheim), 1×Taq reaction buffer (Boehringer Mannheim), 1.5 mM MgCl$_2$, 0.25 mM each dNTP, 0.625 μM primers (P1 and P2). Parameters for thermal cycling were 1× (94° C., 45 seconds; 45° C., 30 seconds; 72° C., 2 minutes), 4–20 × (94° C., 30 seconds; 55° C., 30 seconds; 72° C., 2 mi number of cycles required was inversely proportional to the quantity of starting material, i.e. less cycles were required as the quantity of starting template increased due to ensuing rounds of selection and enrichment of the active component. P2 (N18) and P3 (N4) engineered T17 promoters in the PCR product enabling subsequent transcription as described above. PCR products encoding g4, g6b, g6c, g6d, and N4g1, N4g2 and N4g3, were cloned separately into pBluescript SK+ (Stratagene) using BamHI and KpnI restriction sites. Sequence data was obtained by dideoxy sequencing using Sequenase version 2.0 (United States Biochemical). Cloned material from g4 and g6 was transcribed from pBluescript SK+ linearised with Acc65 I for kinetic assays of individual molecules.

Substrate excess kinetics Kinetic assays were conducted on pooled transcripts from each generation to determine changes in cleavage efficiency. Measurements were made with substrate in excess. Conditions were; 10 nM ribozyme, 4 μM of $^{32}$P labelled 15 mer IL2 RNA substrate (IL2S15), 50 mM Tris-HCl (pH 8.0, 37° C.). Reactions were in 25 μl volumes and were initiated by adding MgCl$_2$ (final concentration 10 mM). Samples (2 μl) were taken at 10 minute intervals and quenched immediately in 4 μl of stop solution (95% formamide, 20 mM EDTA, 0.025% tracking dyes). Samples were separated in 15% polyacrylamide/7 M urea (1×TBE) and the amount of cleavage quantified using ImageQuant (Molecular Dynamics). The V$_{max}$ was obtained from the slope of a linear plot of product formation versus time, and converted to k$_{cat}$; where k$_{cat=Vmax}$/[Rz].

Ribozyme excess kinetics Cleavage rates were also measured for individual molecules from the cloned samples using ribozyme in excess of the substrate. The ribozyme was used at 100 nM, and substrate was 5 nM of $^{32}$P labelled IL2bioS 29 mer RNA. In early experiments the ribozyme concentration was varied to confirm saturating conditions. Reactions were at 37° C. in 50 mM Tris-HCl (pH 8.0 or pH 7.6, as indicated) or 50 mM Mops, pH 7.63, and were initiated by the addition of MgCl$_2$ to a final concentration of 10 mM or 1 mM, as indicated. Samples (2 μl) were removed at 0, 20, 40, 60, 120, 300, 600 seconds, and quenched immediately in 4 μl of stop solution (95% of formamide, 20 mM EDTA, 0.01% tracking dyes). Samples were separated in 15% polyacrylamide/7 M urea (1×TBE) and the amount of cleavage quantified using ImageQuant (Molecular Dynamics). Rate constants ($k_1$) for single-phase reactions were derived by fitting the data to the equation; $P_t=P\infty-(exp(-k_1 t)P_A)$, where $P_t$ is the amount of product at time=t, $P\infty$ is the amount of product at time=∞, $k_1$ is the first order rate constant for the reaction, and $P_{66}$ is the difference between the percentage of product at t=∞ and t=0. For biphasic reactions, the data was fitted to a double-exponential equation; $P_t=[P_1-(exp(-k_1 t)P_{A1})]+[P_2-(exp(-k_2 t)P_2)]$ wherein $k_1$ is the rate constant for the first phase, $k_2$ is the rate constant for the second phase, $P_1$ is the extent of the first phase, $P_{A1}$ is the difference between the percentage of product at $P_1$ and t=0, and $P_2$ is the extent of the second phase of the reaction.

Testing of Miniribozymes in Transgenic CHO Cells Expressing Human PDGF A.

The following procedure was used:

2. Grow 2.5×10⁵ cells (54) in 6 well tissue culture dishes overnight.
3. Wash cells with 2 ml of PBS, followed by 2 ml of Serum Free Medium (SFM) (Dulbecco's MEM/Nutrient mix F12(Coon's modification)(CSL, Melbourne, Australia))
4. Add 300 µl of SFM to each of two polystyrene tubes, to the first tube add 6.25 µl of lipofectamine (Gibco BRL-Life Technologies, Gaithersburg, Md.) and to the second tube add 9.6 ul of a 25 µM stock oligonucieotide. This gave a final oligonucleotide concentration of 0.4 µM, the volume of oligonucleotide added was varied in some experiments.
5. Combine the contents of the 2 tubes and incubate for 10 minutes at room temperature to allow lipid/oligonucleotide complex to form.
6. Aspirate SFM from washed cells and overlay with the 600 µl of SFM containing the lipid/oligo complex.
7. Incubate cells for 4 hours in a $CO_2$ incubator, then harvest total RNA using Sigma (St. Louis, Mo.) Tri-reagent.
8. Analyze PDGF gene expression by ribonuclease protection assay (RPA).

Detection of Miniribozyme Cleavage Products by Ribonuclease Protection Assay.

Ribonuclease protection assays were carried out of total mRNA isolated from PDGF A expressing CHO cells essentially by the method as described by Ausubel et al (55). The probe for RPA was produced by cloning the coding region of the PDGF SA gene into the Bluescribe M13(+) vector (Stratagene, La Jolla, Calif. )and transcribing full length antisense transcripts using T7 RNA polymerase. After RNase digestion this resulted in a full length protected fragment migrating at 637 bp and miniribozyme cleavage fragments migrating at 274 nucleotides (5' fragment) and 363 nucleotides (3' fragment).

Results and Discussion

The central feature of the selection scheme depicted in FIG. 2 is that $Mg^{2+}$ dependent cleavage results in the formation of a ribozyme and 5' cleavage product complex which can be recovered by selective denaturation. The duplex formed between the 3' biotinylated substrate (IL2bioS) and the generation 0 (g0) molecules had an 18 bp double helix 5' of the targeted cleavage site (helix III), and a 6 bp double helix to the 3' of this site (helix I). Using thermodynamic parameters for helix initiation and propagation, provided by Freier et al (34), the $t_m$ for the release of active species carrying the 5' portion of a cleaved substrate was predicted to be ~40° C. The predicted $t_m$ for any given member of the randomised population hybridised to an uncleaved substrate was greater than 90° C. The difference in $t_m$ provided a strong basis of selection for molecules showing trans $Mg^{2+}$ dependent phosphodiesterase activity at, or near, the targeted GUC site in the substrate, allowing quantitative recovery of active species. RNA released from the avidin solid phase, into the supernatant, was collected by ethanol precipitation, amplified (RT-PCR), and transcribed for reiterative enrichment (see Methods section).

Figure 3:
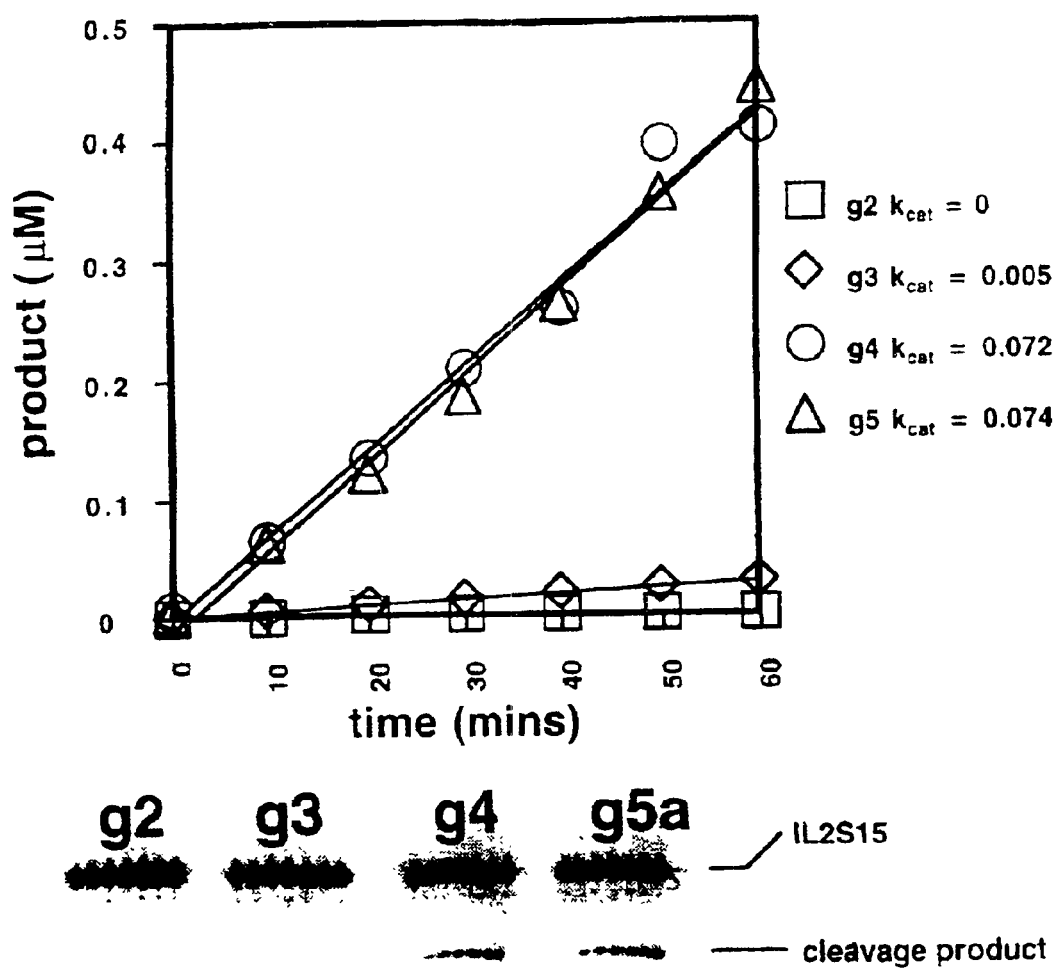
FIG. 3. Enrichment of $Mg^{2+}$ dependent phosphodiesterase activity in the N18pool RNA using a non-stringent high $MgCl_2$ (20 mM) regime. The activity of separate RNA pools generated by iterative in vitro selection was assayed in conditions of substrate excess. Cleavage assay conditions were; ribozyme 100 nM, substrate (IL2S15 15 mer RNA) 40 $\mu$M, 10 mM $MgCl_2$, pH 8.0, 37° C. Cleavage activity ($k_{cat}$) displayed by the random pool RNA became detectable after 3 rounds of selection (g3), and peaked in g4, ie. further enrichment of the $k_{cat}$ phenotype could not be obtained.

Selection at 20 mM $Mg^{2+}$: generation 4 (N18g4) The structure of the starting population (g0) is depicted in FIG. 1. Starting from g0 RNA, 5 rounds of selection using 20 mM $MgCl_2$ for 15 minutes at 37° C. were performed. The populations of RNA resulting from each round of selection were tested for their ability to cleave a radiolabelled RNA substrate in vitro. Generation 3 was the first to show detectable levels of cleavage activity. This activity was improved in generation 4 (g4), but was not increased by additional selection at 20 mM $MgCl_2$, ie. the $k_{cat}$ phenotype of g4 was identical to g5a (FIG. 3).

Amplified material from g4 was cloned and sequenced, revealing a complex population (FIG. 4a). Nonetheless, it was overwhelmingly composed of molecules sharing conserved nucleotides with the hammerhead ribozyme. Molecules exhibiting the conserved hammerhead-like motifs showed high variability between positions 10.1 and 11.1 (inclusive) and at position 7 (although this last position showed a strong pyrimidine bias). The upper limit of diversity for a population which varies randomly in the linker region (10.1–11.1) is $4^6$. The random distribution (0.25) of identities at these positions in g4 was compromised to some extent by a high occurrence of U at position 11.1 and A at position L.3. There is also a lower than expected occurrence of G at positions 10.1, L.2, L.3, and 11.1. However, this effect was slight. The same sequence was not sampled more than once, and the distribution of nucleotides in the linker is significantly random. It was therefore reasonable to maintain that the diversity of g4 approached a substantial part of the $4^6$ maximum (with some additional variation being contributed by position 7). Presumably this diversity reflected the lack of highly stringent demand on the phenotype.

Several molecules which deviated from the hammerhead design were sequenced. No detectable cleavage activity was observed for any of these molecules when tested independently, nor did they exhibit any pooled activity (results not shown). The selection was conducted in trans allowing the possibility of isolating molecules exhibiting dimer dependent activity. Non-hammerhead sequences sampled, could therefore plausibly represent truncations of potentially active structures whose additionally required components have not been observed in the cloned and sequenced sample. Alternatively, these may represent inactive molecules released due to the equilibrium position of the trans RNA duplex. Notable also in g4 is molecule 4.31 (see FIG. 4a) which incorporates an extraneous U, presumably as a bulge in helix Ill. An additional nucleotide can be incorporated between positions 11.1 and 12 (35), and also between 10.1 and 9 (36). In these instances, the additional nucleotide perturbs the structure of helix II, causing reduction, but not loss of activity. In our study, molecule 4.31 exhibited moderate activity at 1 mM $Mg^{2+}$ (Table 1), indicating that a bulge can be accepted here. Whilst 4.31 did not exhibit a high cleavage rate constant, it is not known whether this is attributable to the extraneous nucleotide, or the linker identity (10.1–11.1). Molecule 4.31 and several others have only 5 nucleotides in the linker, and generally these cleaved poorly.

Selection at low $Mg^{2+}$ concentrations: generation 6 (N18g6) To select populations of molecules displaying further enhanced kinetic properties, three high stringency lineages were established from g4 RNA, employing shorter cleavage times and reduced $Mg^{2+}$ concentration (FIG. 5a), producing g6b, g6c, and g6d. These populations showed rate constants ($k_1$) significantly higher than those obtained for g4 (data not shown). Cloning and sequencing amplified material from the generation 6populations revealed that they were much less diverse than N18g4. The reduced diversity was largely accounted for by a significant increase in the frequency of species carrying the sequence 5' G(10.1) NNNNC(11.1) in the linker region. In g4 the occurrence of 5' G(10.1)NNNNC(11.1) was 0.065, ie. close to the expected random incidence (0.25×0.25=0.0625). The occurrence of GNNNNC in the g6 populations was 0.72 (72%), representing a 10-fold enrichment. Of the 72% of the sequences exhibiting the identity GNNNNC, 93.9% are GNNHHC. This identity is concentrated in g6c and g6d families, ie. those populations evolved under the most stringent conditions of $Mg^{2+}$ supply.

N18g6 ribozymes exhibit a variable tolerance to low $Mg^{2+}$ concentrations Cleavage kinetics at 1 mM $MgCl_2$, pH 8.0, 37° C. with ribozyme in excess, were obtained for 28 molecules (24 of which were g6 individuals). Measurements were also made at 10 mM $MgCl_2$, pH 8.0, 37° C. for a subset of 14 molecules (Table 1). The reactions were distinctly biphasic for most molecules both at 1 mM and at 10 mM $Mg^{2+}$. The activity of different molecules could clearly be delineated by rate constants observed for the first rapid phase. While most molecules exhibited a more uniform slower second phase, where $k_2$ was in the range 0.05±0.02 $min^{-1}$ (data not shown), the extent ($P_1$) and rate constant ($k_1$) of the first phase was highly variable. This variation in rate constants for a set of molecules which differed only in the nucleotide composition of the linker between positions A9 and G12, suggested an important role for the linker in structural and catalytic outcomes, where these requirements are only fully satisfied by some, and not other, linker identities. For some molecules, very high rate constants were observed during the first phase of the reaction at both 10 mM and 1 mM $Mg^{2+}$ (see Table 1). It is possible that the linker exerts influence on the equilibrium position between variably active conformations, and that some linkers can cause a redistribution in favour of a more active conformation resulting in high $k_1$ and The rate constants and the extents of the first phase were substantially reduced when $Mg^{2+}$ was lowered from 10 mM to 1 mM. However, the reduction in cleavage activity was not uniform. For some molecules k, dropped dramatically (20–50 fold). In several instances this reduction involved complete extinguishment of the biphasic character of the reaction. At 1 mM these molecules exhibited slow monophasic kinetics. Other molecules experienced only a moderate reduction in extent and rate of the initial cleavage reaction (ie. in the range of 2–5 fold) when $Mg^{2+}$ was lowered to 1 mM. A subset of linkers could therefore be identified which imparted tolerance to low concentrations of $Mg^{2+}$ (shown above the dotted line in Table 1). This group was distinguished on the basis of exhibiting $k_1 \geq 0.5$ $min^{-1}$, and $P_1 > 10\%$ at 1 mM $MgCl_2$ pH 8.0, 37° C.

N4 linker selection at 1 mM $Mg^{2+}$ The result of the initial phase of selection at 20 mM $Mg^{2+}$ is given in FIG. 4a (showing generation 4). This population was directed through further rounds of selection at reduced $Mg^{2+}$ concentration producing populations g6b, g6c, g6d (FIG. 4b). Cleavage rate constants for a set of these molecules suggested that variants which show high activity at low $Mg^{2+}$ concentration, comprise a discrete fraction of the entire set. The nature of this set was investigated by renewed selection, devised specifically to optimise identity between positions 10.1 and 11.1 (ie. L.1–L.4).

Figure 5:
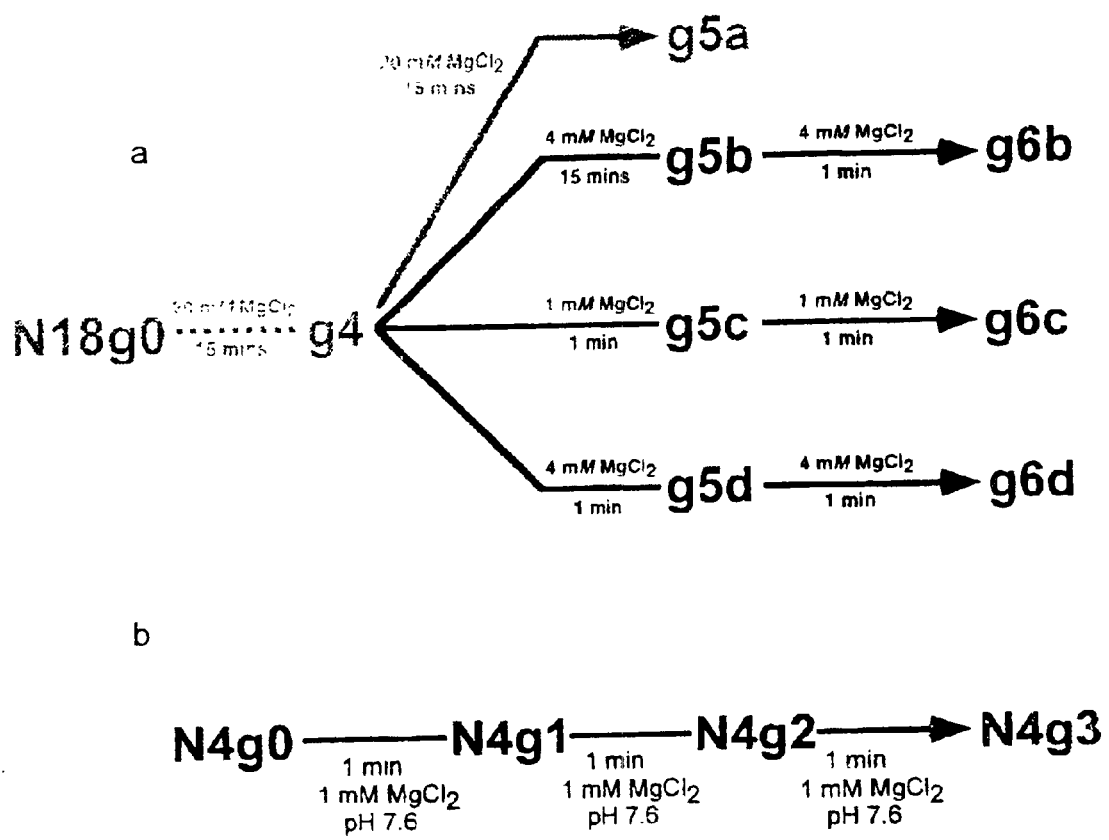
FIG. 5. $MgCl_2$ concentration and incubation time used during selection, showing (a) the inception and differences between the three high stringency lineages established from the N18g4 pool, and (b) the protocol used for the N4 experiment.

Table 1 reveals that the composition of the linker region in minimised hammerheads is enormously significant. Most sequences will only support very low rates of cleavage. In the most highly evolved populations (g6c and g6d) the dramatic enrichment of molecules bearing the sequence motif G(10.1)NNNNC(11.1) was correlated to significantly improved cleavage rate constants for those populations (data not shown). However, kinetic analysis of individual members of these populations revealed that the G(10.1)NNNNC (11.1) motif, of itself, is insufficient to confer a robust cleavage phenotype ($k_1$ determined at 1 mM range from 0.04–1.4 $min^{-1}$). Rather it predisposed molecules towards having moderate to high cleavage kinetics (10 out of 17 molecules bearing this motif, displayed first phase $k_1$ values $\geq 0.5$ $min^{-1}$, with only 4 having values $\leq 0.1$, at 1 mM $Mg^{2+}$, pH 8.0, 37° C.). The data indicated that only a very small number of linker permutations satisfy the requirement for very high cleavage activity. Assuming that a G. at position 10.1 and a C at position 11.1 represents a kinetically favourable scaffold, we prepared a new randomised population of molecules, N4g0 (FIG. 2c), comprising all 256 GNNNNC possibilities, and subjected this population to three rounds of selection with $Mg^{2+}$ supply limited to 1 mM (FIG. 5b). Amplified material from the resulting N4g 1, N4g2, and N4g3, was cloned and sequenced. All the sampled molecules fit the description 5' NNHH in the linker region (L.1–L.4) as originally suggested by the N18g6 consensus. The set includes some molecules which were previously observed plus additional representatives. Sequence data obtained from N4g3 allowed us to recognise three distinct classes of molecule within the NNHH family (FIG. 6). The high activity group identified among the N18g6 molecules, shown above the dofted line in Table 1, can be ascribed to these three classes. The data contained within the low $Mg^{2+}$ evolved N4 populations therefore supports the finding from the low $Mg^{2+}$ evolved N18g6 populations, that there is a discrete composition of linker which is required for high activity at low $Mg^{2+}$ concentration.

TABLE 1

Kinetic paramaters for selected ribozymes at 1 mM and 10 mM $MgCl_2$. Substrate was IL2biosS (29mer RNA).

| Ribo- | Linker Position | | | Cleavage Kinetics 1 mM (10 mM)$^a$ $MgCl_2$, pH 8.0, 37° C. | | |
|---|---|---|---|---|---|---|
| zyme | 10.1 | L.1–L.4 | 11.1 | $k_1^b$ | $P_1^c$ | $P\infty^d$ |
| 6.18 | | CACC | | 0.9 | 13.0 | 81.3 |
| 6.21 | | UUUU | | 0.9(4.8)$^d$ | 47.3(59.5) | 77.3(91.3) |
| 6.24 | | UUAA | | 1.0(1.9) | 36.6(51.8) | 84.4(80.8) |
| 6.17 | | UCCA | | 1.1(5.5) | 14.5(23.3) | 83.9(62.1) |
| 6.14 | | UCUA | | 0.5(2.3) | 36.1(50.3 | 70.8(77.6) |
| 6c10 | | GUAA | | 0.6(3.0) | 44.9(41.5) | 81.4(76.6) |
| 6.22 | | CAUA | | 0.9 | 8.8 | 72.8 |

TABLE 1-continued

Kinetic paramaters for selected ribozymes at 1 mM and 10 mM MgCl$_2$.
Substrate was IL2biosS (29mer RNA).

| Ribo-zyme | Linker Position 10.1 | L.1–L.4 | 11.1 | Cleavage Kinetics 1 mM (10 mM)$^a$ MgCl$_2$, pH 8.0, 37° C. $k_1^b$ | $P_1^c$ | $P\infty^d$ |
|---|---|---|---|---|---|---|
| 6.19 | | CUAA | | 0.5 | 5.2 | 65.3 |
| 6.11 | | CAAA | | 1.1(4.3) | 4.4(37.3) | 98.0(88.9) |
| 6.7 | | CUAA | | 1.4 | 2.3 | 54.4 |
| 6.2 | | ACCA | | 0.7 | 7.5 | 74.0 |
| 6.5 | | GGGA | | 0.07 | — | 79.7 |
| 6.10 | | GGGA | | 0.04(0.4) | — | 75.5 |
| 6.16 | | GCAA | | 0.32(2.7) | 7.2(38.4) | 88.1(82.6 |
| 6.20 | | CUCC | | 0.9 | 5.1 | 37.0 |
| 6.23 | | AAAC | | 0.02 | — | 76.6 |
| 4.14 | | AAU | | 0.04(0.6) | — (11.6) | 68.0(73.6) |
| 4.13 | G | UAU | U | 0.02(0.7) | — (7.9) | 73.7(69.4) |
| 6b9 | A | UAU | U | 0.01 | — | 67.2 |
| 6.3 | A | GAAA | U | 1.1(1.7) | 6.5(31.4) | 43.2(55.8) |
| 6.4 | A | UUUU | G | 0.007 | — | 32.1 |
| 6.12 | C | UUGG | A | 0.01(0.04) | — | 49.1(64.2) |
| 4.31 | U | UAU | U | 0.007 | — | 44.7 |
| 6.6 | U | UUGG | U | 0.01 | — | 97.1 |
| 4.21 | U | CCAC | U | 0.006 | — | 67.7 |
| 6.9 | U | AUUU | U | 0.5(1.0) | 6.6(52.8) | 76.4(93.8) |
| 6.13 | U | AUUA | U | 0.009(1.1) | — (4.2) | 76.4(94.2 |
| 6d10 | U | GGUA | U | 0.008 | — | 77.4 |

$^a$values in parenthesis () were obtained using 10 mM MgCl$_2$ in the cleavage reaction.
$^b k_1$ = first order rate constant (min$^{-1}$).
$^c P_1$ = extent of the first phase (percentage cleaved).
$^d P\infty = P_1 + P_2$, estimated endpoint (percentage cleaved).
$^e$highlighted block are those molecules that a G at position 10.1 and a C at position 11.1.

Refining the Consensus Sequence for the 4-nucleotide Linker.

In the initial experiment three rounds of selection were performed with products cloned after each selection. In this latter experiment, two further rounds of selection were performed as described. The pcr products after the fifth selection step were cloned and sequenced using the SUPAMAC sequence facility and dye-terminator based sequencing. The sequences obtained are presented in Table 2.

TABLE 2

Sequence data obtained from N4g5 clones

| Clone number | Sequence |
|---|---|
| N4g5-1 | CTGATGAGTTATCGAAAC |
| N4g5-2 | CTGATGAGGTAACGAAAC |
| N4g5-3 | CTGATGAGACCCCGAAAC |
| N4g5-4 | CTGATGAGATAACGAAAC |
| N4g5-5 | CTGATGAGACCCCGAAAC |
| N4g5-7 | CTGATGAGACCCCGAAAC |
| N4g5-9 | CTGATGAGATACCGAAAC |
| N4g5-11 | CTGATGAGATACCGAAAC |
| N4g5-13 | CTGATGAGTTTCCGAAAC |
| N4g5-14 | CTGATGAGTTTTCGAAAC |
| N4g5-15 | CTGATGAGTTACCGAAAC |
| N4g5-16 | CTGATGAGACACCGAAAC |
| N4g5-17 | CTGATGAGTTAACGAAAC |
| N4g5-18 | CTGATGAGTTACCGAAAC |
| N4g5-19 | CTGATGAGACCCCGAAAC |
| N4g5-21 | CTGATGAGTTTACGAAAC |
| N4g5-23 | CTGATGAGACCCCGAAAC |
| N4g5-24 | CTGATGAGTTACCGAAAC |
| N4g5-26 | CTGATGAGTTACCGAAAC |
| N4g5-27 | CTGATGAGACCCCGAAAC |
| N4g5-28 | CTGATGAGTTATCGAAAC |
| N4g5-30 | CTGATGAGTTTACGAAAC |
| N4g5-31 | CTGATGAGTTTACGAAAC |
| N4g5-32 | CTGATGAGACCCCGAAAC |

TABLE 3

Summary of N4g5 Sequence Data (as RNA).

| Sequence | Frequency | Clone IDs |
|---|---|---|
| GUAA | 1 | 2 |
| ACAC | 1 | 16 |
| ACCC | 7 | 3, 5, 7, 19, 23, 27, 32 |
| AUAA | 1 | 4 |
| AUAC | 2 | 9, 11 |
| UUAA | 1 | 17 |
| UUAC | 4 | 15, 18, 24, 26 |
| UUAU | 2 | 1, 28 |
| UUUA | 3 | 21, 30, 31 |
| UUUC | 1 | 13 |
| UUUU | 1 | 14 |

The sequences obtained from the N4g5 population are remarkable for a lack of guanosine in any position. There is a single guanosine residue present in the sample population of 24 different sequences. With the exception of that GUM sequence, the consensus sequence for the selected linker is WYHH. With the GUM sequence included, the consensus sequence is DYHH. There are a number of sequences that appear multiple times, the most notable being ACCC which occurs seven times. The next most common being UUAC which occurred four times. Both these sequences occurred in the N4g3 population analysed earlier. The WYHH class of linkers which were the most common (19/25) in the N4g3 population have become more dominant by the 5th generation (23/24). Only the highly active GUM linker remains from the other classes. Although not measured directly in this experiment, it is reasonable to assume that this class of linker, particularly those members which have been selected and sequenced, would impart high cleavage activity upon a miniribozyme which possessed it.

Novel classes of RNA tetraloop Rate enhancement of hydrolysis of the scissile RNA phosphodiester bond in a miniribozyme/substrate complex, is presumably dependent on specific tertiary architecture. Effective linkers may exhibit structure which supports the catalytic core and whose sequence identity reduces the scope for misfolding. We would expect some linker structures to favour the adoption of an active conformation by reducing the number of steric possibilities, limiting the occurrence of events which constitute freedom to explore unreactive configurations. Others might suppress it by imposing torsion on the architecture or promoting an inactive structure, eg. through misfolding induced by inadvertent intramolecular homology.

Linkers supporting improved kinetic activity presumably act by providing a scaffold which will promote the correct folding of the conserved G-A base pair stack which constitutes domain II in the hammerhead crystal structures (29). The formation of this domain was proposed as the first of two tertiary folding movements required for progression to the catalytic ground state (21). Our data suggests that a G(10.1).C(11.1) base pair provides a key component of this scaffold. We propose that the other key component of an optimal scaffold in a miniribozyme is a linker sequence able to form a stable tetraloop between positions 10.1 and 11.1, ie. a structure which is able to turn around a narrow enough radius without creating torsion on the complex base-paired structure which stacks above it. This hypothesis is supported by the statistically high occurrence of the known tetraloop GNRA in the g6 populations (0.15 as compared to 0.03 expected random occurrence). The GNRA motif forms a sheared G-A base pair which enables it to reverse the direction of the RNA backbone within an extremely narrow radius (37). It is also thought to assist in the initiation of hairpin folding (38–41). This folding dynamic in a miniribozyme would assist in providing a favourable equilibrium position, allowing a higher proportion of the molecules to be in an active conformation at any one time. However, there is evidence that some known stable tetraloops do not satisfy the requirement for high cleavage rates in a miniribozyme. For instance, the stable tetraloop CUUG, when incorporated into a G(10.1).C(11.1) miniribozyme, exhibited poor cleavage kinetics (28). Tetraloops are therefore effective within a context and do not necessarily transfer this effect when incorporated in a different context. The most effective molecules characterised here were GUUUC (6.21), GGUMC (6c10), and GUCUAC (6.14). Related molecules occurred at high frequency in the low $Mg^{2+}$ selected N4 populations. Presumably these sequences are able to execute an effective turn through a narrow space without disrupting the correct base paired structure essential for optimum catalysis. Three classes of molecule were delineated in the N4g3 sequence data (FIG. 6). All conform to the 5' NNHH consensus identified previously. Class I consensus (5' YRHH) includes UGAA (a known tetraloop (42). Class III has significant homology with the GNRA family. Class II does not resemble any known tetraloops, and therefore represents a novel and highly represented classification.

Tolerance to low $Mg^{2+}$ concentration The hammerhead ribozyme appears to be dependent on $Mg^{2+}$ for a structural transition within the ribozyme/substrate complex, which leads to the formation of the ground state. In the reaction, $Mg^{2+}$ is thought to directly catalyse both the activation of the 2' nucleophile for attack on the phosphate centre, and the rate of departure of the 5' oxo leaving group. The composition of the linker in a miniribozyme could lower the $Mg^{2+}$ dependence for any of these functions. Bassi and co-workers (19–21) have studied a structural equilibrium of the hammerhead as a function of $Mg^{2+}$ concentration. High magnesium ion concentration favours the more active conformation (20). The biphasic kinetics we observe here suggest that there is a kinetic barrier between active and inactive forms of the ribozyme-substrate complex, and that the position of the equilibrium, as well as the activity of the active form, is dependent on the nature of the linker between positions A9 and G12.

Crystal structures indicate a $Mg^{2+}$ binding site at the apex of helix II in the hammerhead (22,29,30,43). Coordinating ligands indicated by Scott et al (30) are G8 (2'O), A9 (P1-O), G10.1 (N7), and G12 (N2). Whilst the miniribozyme is a novel structure, these positions are conserved (including G10.1 in the highly active species), therefore maintaining this binding potential. This binding site is suggested in all crystal structures for the conventional hammerhead, and has been proposed as a significant determinant of activity (29). The Kd of $Mg^{2+}$ for this site will presumably be affected by the sequence of the linker region which lies immediately beneath it, and whose composition will affect the structure of the binding pocket. It is possible that some of the linkers provide optimal support for this function or that they provide an additional, or alternative high affinity $Mg^{2+}$ binding site.

Another view is that stable and structurally appropriate tetraloop formation between positions 10. 1–11.1 is able to facilitate a high $K_d$ for $Mg^{2+}$ in the catalytic core itself. This could involve the catalytic ion(s) or other specifically bound ions involved in structure. One proposed metal binding site involves A14 (20,44), and has a plausible role in influencing the formation of the core purine stack A9-G12 and GB-A13 (domain II, see FIG. 1). Also, several studies (19,22,30, 45–47) have indicated a metal binding site associated with G5 and A6 in the CUGA unpaired motif between helices I and II (positions 3–6) in the hammerhead, associated with the folding of domain 2. In structures by Scoft et al (22,30, 43) there are additional sites, one involving C3 and U4 and C17. This ion appears to coordinate with the 5'-O leaving group, and has a plausible role in catalysing its departure. A further ion is positioned to allow direct coordination with the pro-R oxygen adjacent to the scissile bond, and -is plausibly implicated in activating the 2'-O nucleophile. In miniribozymes, the composition and proximity of the 10.1–11.1 linker must have considerable bearing on the structure of this core region, and could therefore determine the $Mg^{2+}$ sensitivity of the catalytic outcome.

KrMc10 and IL2Mc10 (miniribozymes with evolved linkers) versus KrRz and IL2Rz (hammerhead ribozymes with full length helix II) The data we have obtained suggests that the capacity for high cleavage rate constants in a miniribozyme is imparted by specific linker sequences. We next wished to see if a linker we identified could impart favourable kinetic properties when it was incorporated into a miniribozyme targeted to a different substrate. Miniribozymes with a 6c10 GGUAAC identity in the linker were chemically synthesised with 9 nucleotides in each hybridising arm to target a 19 mer human IL2 mRNA substrate (IL2S19) and a 17 mer Drosophila melanogaster Krüppel mRNA substrate (KrS17). These substrates provided targets with 9 nucleotides (IL2S19) and 8 nucleotides (KrS17) arranged symmetrically on either side of the unpaired C adjacent to the scissile phosphodiester bond. Rate constants for these miniribozymes were measured at 1 mM and 10 mM MgCl$_2$ (pH 7.6, 37° C.) and compared to those obtained for hammerhead ribozymes (KrRz and IL2Rz). KrRz was constructed with 10 nucleotides in each arm and IL2Rz was constructed with 9 nucleotides in each arm. Both KrRz and IL2Rz had 4 Watson-Crick base pairs in helix II.

Table 4 illustrates that the favourable kinetic traits exhibited by the 6c10 motif were equally observed in both the Krüppel and IL2 substrate backgrounds. KrMc10 and IL2Mc10 (miniribozymes with 6c10 linkers) were also more active than similarly constructed molecules with full length helix II. When cleaving gene length substrates, optimum results for both minimised and conventional hammerhead ribozymes are obtained when helix I and helix III are each ~9 bp (48,49). However, cleavage rate constants for conventional hammerheads-on-short substrates vary markedly in response to the length of helix I, and appear to be highest when helix I is 5–6 bp (31). Rate constants for miniribozymes appear to be less susceptible to changes in arm length (32). When helix I is 9 bp or 8 bp, rate constants for the hammerhead ribozyme were poor as compared to the optimised miniribozymes described here. Furthermore, the difference between miniribozymes and hammerheads becomes greater when Mg$^{2+}$ concentration is low.

Relation to other work The most recent communication involving hexanucleotide replacement of helix II, reported G(10.1)CGNGC(11.1) as a highly active set of motifs identified using in vitro selection (50). Rate constants for the most active motif (GCGUGC) were 0.64 min$^{-1}$ (0° C., 1 mM MgCl$_2$, pH 8.0), and 0.23 min$^{-1}$ (37° C. 1 mM MgCl$_2$, pH 8.0). Zillmann et al clearly indicate that C(L.1).G(L.4) is a preferred identity according to their scheme of selection. In the context of the bacterial rRNA CUUG tetraloop, the C-G form a buckled base pair allowing an efficient and stable turn in the stable turn in the RNA backbone (51). However, this motif has been indicated to provide an inadequate scaffold for a miniribozyme (28), and our results suggests that a G at position L.4 is unfavourable. The differences between the Zillmann result and those reported here is no doubt due to the design of the selection protocol. Their study reports that selection was conducted at 0° C. and with very long helices I and III. The observation that the GCGUGC molecule cleaves its substrate more rapidly at a lower temperature is unusual. This perhaps illustrates the need to formulate conditions of selection which are consistent with the intended use of the molecule. At a physiologically relevant temperature (37° C.) the molecules we have identified in this study cleave between 2 and 10 times more rapidly than those identified by Zillmann et al. Previous studies have demonstrated that the replacement of stem-loop II in the hammerhead with a six nucleotide linker resulted in a reduction of catalytic activity. Tuschl and Eckstein (28) report an order of magnitude reduction in k$_{cat}$ (ie. 3.1 min$^{-1}$ to 0.3 min$^{-1}$) when a 4 bp helix II was replaced by the linker sequence G(10.1)CUUGC(11.1). Similarly, Long and Uhlenbeck (52) report a 10-fold decrease in k$_{cis}$ (1.0 to 0.09 min$^{-1}$) and k$_{cat}$ (1.5 to 0.12 min$^{-1}$) when they compare a 4 bp helix II molecule to G(10.1)UUUGC(11.1).

TABLE 4

Kinetic parameters for cleavage of IL2S19 by IL2Mc10 (GGUAAC linker) and IL2Rz, and KrS17 by KrMc10 (GGUAAC linker) and KrRz, at 1 mM and 10 mM MgCl$_2$.

| | | Cleavage Kinetics 1 mM (10 mM)$^a$ MgCl$_2$, pH 7.6, 37° C. | | |
|---|---|---|---|---|
| Ribozyme | 10.1–11.1 | k$_1$$^b$ | P$_1$$^c$ | p∞$^d$ |
| IL2Mc10 | GGUAAC | 1.3(3.6)$^a$ | 22.2(60.0) | 74.8(75.6) |
| IL2Rz | GUCCUUUUGGAC | 0.3(3.9) | —(27.9) | 31.7(44.2) |
| KrMc10 | GGUAAC | 1.3(3.8) | 21.0(54.9) | 75.4(75.6) |
| KrRz | GUCCUUUUGGAC | 0.1(2.4) | —(39.5) | 55.4(59.3) |

$^a$values in parenthesis ( ) were obtained using 10 mM MgCl$_2$ in the cleavage reaction.
$^b$k$_1$ = first order rate constant (min$^{-1}$).
$^c$P$_1$ = extent of the first phase (percentage cleaved).
$^d$p∞ = P$_1$ + P$_2$, estimated endpoint (percentage cleaved).

Consensus Sequence for the 5-nucleotide Linker.

Having observed the high activity of the hexanucleotide linker (GNNNNC), we investigated the activity of the 7-nucleotide linker (GNNNNNC). An exactly analogous experiment was performed for five rounds of selection and amplification prior to cloning and sequencing. The sequencing results of the N5g5 population are shown in Table 5.

TABLE 5

Sequence data obtained from N5g5 clones

| Clone number | Sequence |
|---|---|
| N5g5-2 | CTGATGAGTCCTACGAAAC |
| N5g5-7 | CTGATGAGTCCCACGAAAC |
| N5g5-10 | CTGATGAGAATTTCGAAAC |
| N5g5-11 | CTGATGAGTCCCACGAAAC |
| N5g5-16 | CTGATGAGTTAAACGAAAC |
| N5g5-19 | CTGATGAGTCCCACGAAAC |
| N5g5-20 | CTGATGAGTCCCCCGAAAC |
| N5g5-21 | CTGATGAGCACCCCGAAAC |
| N5g5-22 | CTGATGAGTCCCACGAAAC |
| N5g5-25 | CTGATGAGTGTCCCGAAAC |
| N5g5-26 | CTGATGAGTTTTACGAAAC |

TABLE 5-continued

Sequence data obtained from N5q5 clones

| Clone number | Sequence |
| --- | --- |
| N5q5-27 | CTGATGAGAATTTCGAAAC |
| N5q5-31 | CTGATGAGTCCCACGAAAC |
| N5q5-32 | CTGATGAGTGTTACGAAAC |
| N5q5-33 | CTGATGAGTCCCACGAAAC |
| N5q5-36 | CTGACGAGTCCCACGAAAC |

TABLE 6

Summary of N5q5 Sequence Data (as RNA).

| Linker Sequence (as RNA) | Frequency | Clone numbers |
| --- | --- | --- |
| UCCUA | 1 | 2 |
| UCCCA | 7 | 7, 11, 19, 22, 31, 33, 36 |
| AAUUU | 2 | 10, 27 |
| UUAAA | 1 | 16 |
| UCCCC | 1 | 20 |
| CACCC | 1 | 21 |
| UGUCC | 1 | 25 |
| UUUUA | 1 | 26 |
| UGUAA | 1 | 32 |

The selected sequences in the N5 linker population, like the N4 population, display a scarcity of guanosine nucleotide, there are only 2 guanosines in the 80 sequenced bases. The next notable feature of the selected sequences is the frequency with the bases at positions L2.1 and 2.5 (as defined by Hertel et at, 53) are complementary. Of the 16 sequences, 13 of them have the potential to create U-A base pairs between the terminal nucleotides in the sequence. Interestingly, U(L2.1)-A(L2.5) is much more common (11 times) than A(L2.1)-U(L2.5) (2 times). It is also noteworthy that no potential G-C pairs in that position were observed. Taken as a whole there is a consensus of HNHHH for the linker sequence. The population can be divided into three classes, one class is based on the very common sequence UCCCA and allowing for single base changes at any position makes up 9 of the 16 observed sequences, ie UCCCA, UCCCC and UCCUA. The second class of linker is composed solely of adenine and uridine nucleotides and includes AAUUU, UUAAA and UUUUA and occurs a total of four times. Finally there are three sequences that fall outside these other two classes and are UGUCC, UGUUA and CACCC.

Synthesis and Testing of DNA Containing Analogues.

Figure 7:
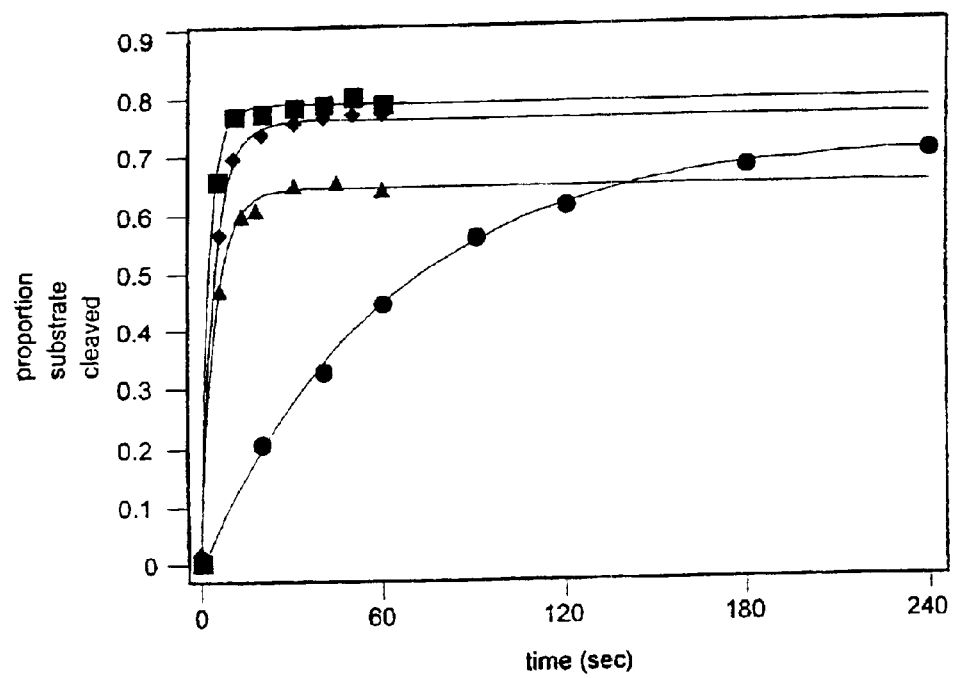
FIG. 7 Cleavage of PDGF293-S25 by Miniribozymes PDGF293-MR1 ( ), PDGF293-MR2 (■), PDGF-MR3 (♦) and PDGF-MR4 (▲). Conditions 50 mM Mops pH 7.63, 37° C., 10 mM $MgCl_2$, [Miniribozymes]=1 $\mu$M, [Substrate]=5 nM.
Figure 8:
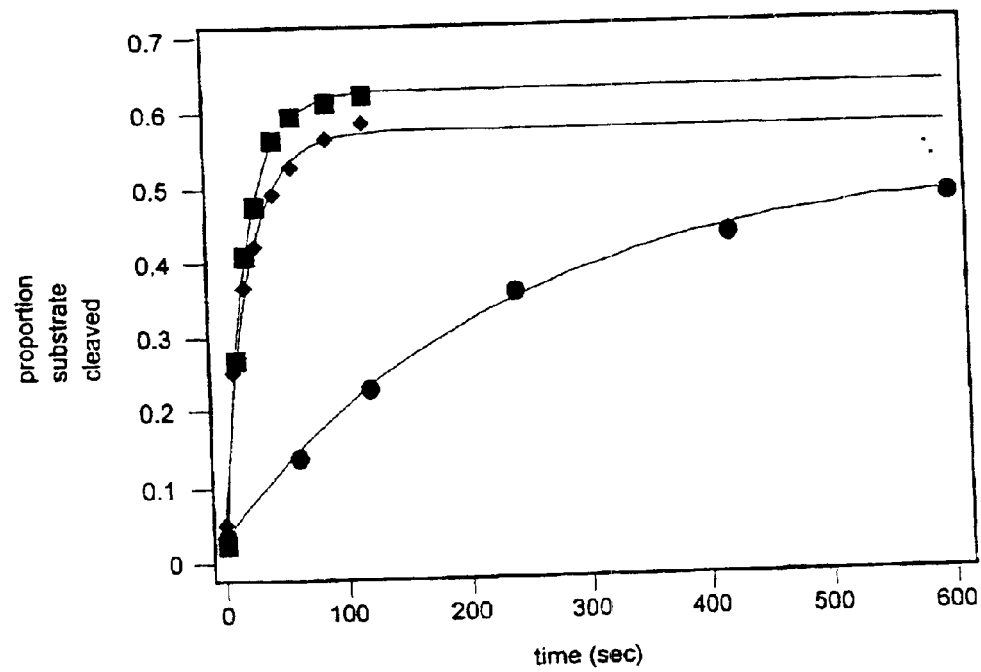
FIG. 8 Cleavage of PDGF293-S25 by Miniribozymes PDGF293-MR1 ( ), PDGF293-MR2 (■), and PDGF-MR3 (♦). Conditions 50 mM Mops pH 7.63, 37° C., 1 mM MgCl$_2$, [Miniribozymes]=1 μM, [Substrate]=5 nM.

A miniribozyme (PDGF293 MR1) targeting a site in the human platelet derived growth factor A mRNA was synthesised by solid phase methods. The linker sequence was one of the selected sequences, GUAA. The miniribozyme was all-RNA except that the 3' terminal nucleotide was a deoxy-nucleotide for convenience of synthesis. Analogues (PDGF293 MR2, PDGF293 MR3 and PDGF293 MR4) containing further deoxy-nucleotide substitutions were synthesised. MR2 contained the linker sequence d(ggtaac) in an otherwise all-RNA molecule (except for the 3' terminal deoxythymidine), MR3 was composed of a DNA linker and DNA hybridising arms, MR4 had one hybridising arm that was DNA, another as RNA and the linker sequence alternated DNA and RNA. All three extensively DNA substituted analogues were even more active that the largely RNA miniribozyme, FIGS. 7 and 8).

Solid lines are lines of best fit to single exponential equations as described earlier. Cleavage rate constants and $P_\infty$ values for the reactions are given in Table 7.

TABLE 7

Kinetic constants for in vitro cleavage of PDGF S25
Conditions: 37° C., pH 7.63.

| Miniribozyme | [$Mg^{2+}$] | $k_{obs}$ (min$^{-1}$) | $P_\infty$ |
| --- | --- | --- | --- |
| PDGF293 MR1 | 10 | 1.02 ± 0.05 | 0.72 |
| PDGF293 MR2 | 10 | 21 ± 2 | 0.80 |
| PDGF293 MR3 | 10 | 17 ± 5 | 0.78 |
| PDGF293 MR4 | 10 | 10 ± 2 | 0.70 |
| PDGF293 MR1 | 1 | 0.26 ± .01 | 0.52 |
| PDGF293 MR2 | 1 | 2.8 ± 0 | 0.63 |
| PDGF293 MR3 | 1 | 2.5 ± 0.2 | 0.58 |

It is apparent from these data that this (GUM) selected linker sequence conveys good cleavage activity at both 10 and 1 mM $MgCl_2$ to a miniribozyme with different cleavage specificity from the one in which the selection was performed. In addition, incorporation of DNA into the linker sequence further improves the cleavage activity of the miniribozyme. This observation holds for a miniribozyme with either DNA (MR3) or RNA (MR2) in its hybridising arms.

Synthesis and Testing of Analogues Containing Modified Nucleotides.

Figure 9:
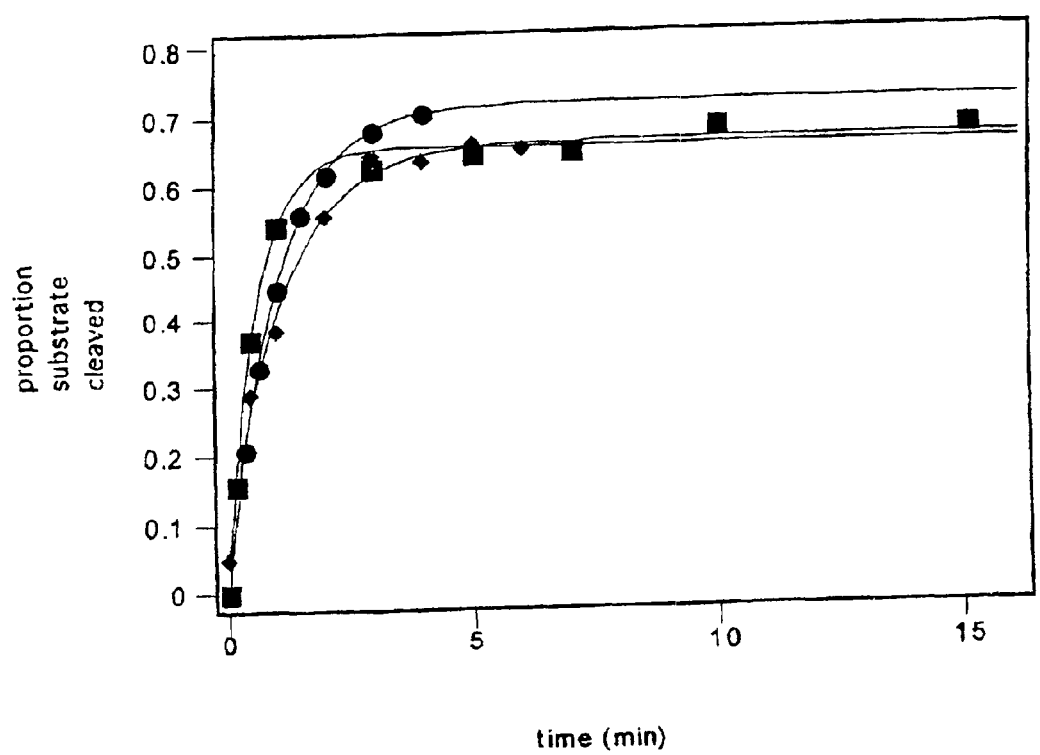
FIG. 9 Cleavage of PDGF293-S25 by Miniribozymes PDGF293-MR1 (●), PDGF293-MR5 (■), and PDGF-MR6 (♦). Conditions 50 mM Mops pH 7.63, 37° C., 10 mM MgCl$_2$, [Miniribozymes]=1 μM, [Substrate]=5 nM.

Miniribozymes (PDGF293 MR 5, and PDGF293 MR6) containing modified nucleotides were synthesised and tested for in vitro cleavage ability against the short (25 mer) PDGF substrate. PDGF293 MR5 was composed largely of RNA but contained a 2' O-methyl substituted uridine and a 2'-fluoro cytidine in the linker sequence in addition to the usual 3' terminal deoxythymidine. PDGF293 MR6 was designed to be tested in living cells and as such had extensive modification throughout the sequence, most of the pyrimidine nucleotides in the molecule were 2' O-methyl modified, the linker was all DNA and the position U4 was phosphorothioate modified. Both these miniribozymes were able to cleave the 25-mer PDGF substrate as efficiently as the unmodified miniribozyme (MR1) (FIG. 9).

Figure 10:
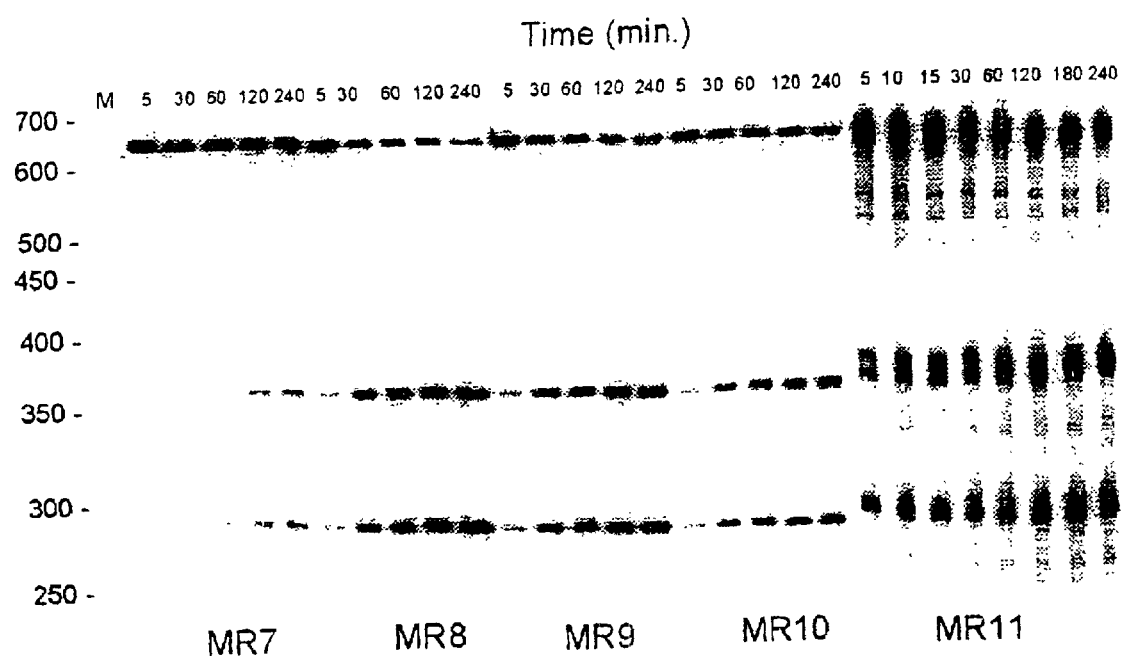
FIG. 10 Cleavage of PDGF transcript (637 nt) Miniribozymes MR7, MR8, MR9, MR10 and MR11 with hybridising arm varying from 6 nucleotides each (MR6) to 14 nucleotides each (MR11); cleavage conditions 37° C., 1 mM MgCl$_2$, 50 mM Tris pH 8.0, [Miniribozymes]=1.25 mM, [Substrate]<10 nM.

A series of miniribozymes (PDGF293 MR7–11) were synthesised in which the hybridising arms varied in length from six in each arm to fourteen in each arm. In addition having 2' O-methyl pyrimidines in the hybridising arms an at C3 and U7, the U4 position was protected with a phosphorothioate and the linker sequence ggtaac, was DNA. The ability of these ribozymes to cleave the 637 nt PDGF transcript was tested in vitro at pH 8.0, 1 mM $MgCl_2$ and 37° C. The results of those cleavage reactions are shown in FIG. 10 and calculated kinetic parameters are given in Table 8. All the miniribozymes are able to cleave the PDGF transcript, the miniribozyme with only six nucleotides in each hybridising arm being the least efficient.

TABLE 8

Kinetic parameters for reactions shown in FIG. 10, cleavage of PDGF transcript by Miniribozymes with varying hybridising arm length; cleavage conditions 37° C., 1 mM $MgCl_2$, 50 mM Tris pH 8.0, [Miniribozyme] = 1.25 µM, [Substrate] < 10 nM.

| Miniribozyme | $k_{obs}$ (min$^{-1}$) | $P_\infty$ |
| --- | --- | --- |
| PDGF293 MR7 | 0.0025 | 0.35 |
| PDGF293 MR8 | 0.038 | 0.848 |
| PDGF293 MR9 | 0.048 | 0.733 |
| PDGF293 MR10 | 0.033 | 0.465 |
| PDGF293 MR11 | 0.023 | 0.639 |

Activity of Miniribozymes in Cells.

Figure 11:
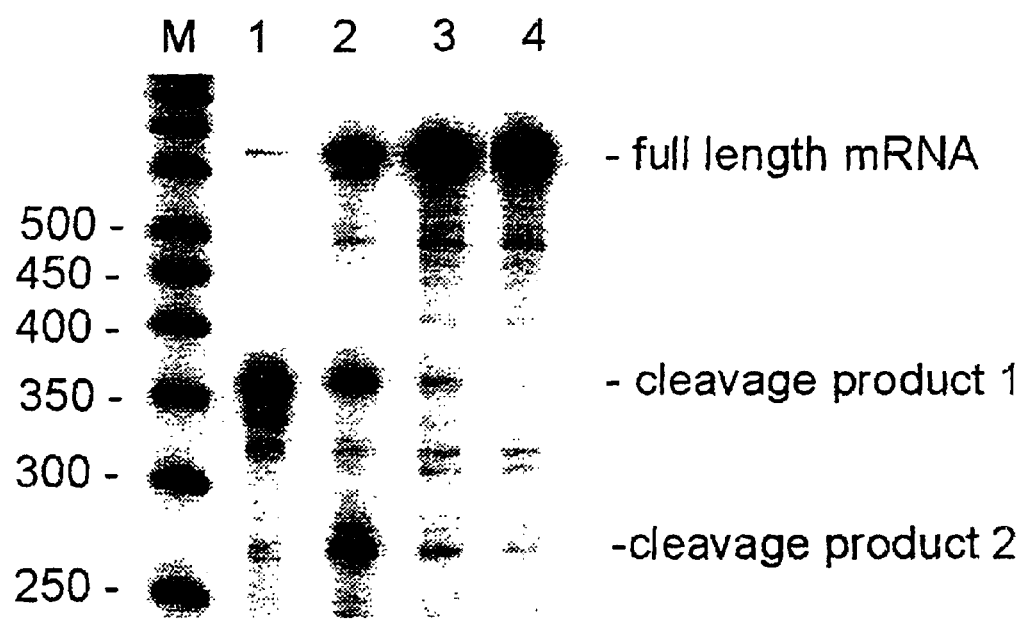
FIG. 11 Ribonuclease protection analysis of RNA extracted from PDGF expressing CHO cells treated as described with:
1 Phosphorothioate antisense (1.0 mM)
2 PDGF293 MR9 (0.4 μM)
3 PDGF293 MR12 (0.4 μM)
1. 4 no treatment FIG. 12 Ribonuclease protection analysis of RNA extracted from PDGF expressing CHO cells treated varying concentrations (as indicated) of PDGF293 MR9, PDGF293 MR13 and no treatment (n/t).

CHO cells constitutively expressing PDGF-A (55) were transfected with solid-phase synthesised miniribozymes (PDGF293 MR9 and MR12) designed to cleave at position 293 in the PDGF-A mRNA. In addition, a phosphorothioate antisense molecule was tested. After four hours RNA was extracted from the cells and analysed by an RNAse Protection Assay. The radioactive probe for the assay covered each side of the predicted cleavage site, so both cleavage fragments of the PDGF-A mRNA, if present would be detected. This cell line contains appreciable amounts of the enzyme RNAse H, and so the phosphorothioate antisense molecule is a good positive control in this experiment. The miniribozymes in these experiments were designed so that the hybridising arms when bound to the target, would not form a substrate for RNAse H. This was done in order to be able to unequivocally demonstrate the intrinsic cleavage ability of the miniribozymes. The results of the experiments are shown in FIG. 11, the two active miniribozymes generate distinct cleavage products in the RPA which are consistent with cleavage occurring within the cells during the experiment. Untreated cells did not show any such cleavage products. The RNA from cells treated with phosphorothioate antisense showed a single major band in the RPA. This is consistent with expected size of the 3' cleavage fragment of the PDGF-A mRNA. Since it is expected that the RNAse H would digest away much of the RNA that was initially bound to the antisense molecule, the two remaining RNA fragments would become free in solution, and apparently the 5' cleavage product, which now contains an unprotected 3' terminus is not stable in the cell and is rapidly degraded. In contrast, cleavage by the miniribozyme occurs discretely at a single bond and it appears likely that both ends of the PDGF cleavage product remain bound to the hybridising arms of the miniribozyme (by virtue of their length and composition) and both fragments are thereby protected from cellular exonucleases, and both are observed. In four separate experiments the amount of cleaved PDGF RNA observed as a proportion of the total was: phosphorothioate antisense 92±2%, MR9 35±6%, MR12 4.5±0.3% and untreated cells 2.7±0.3%.

Figure 12:
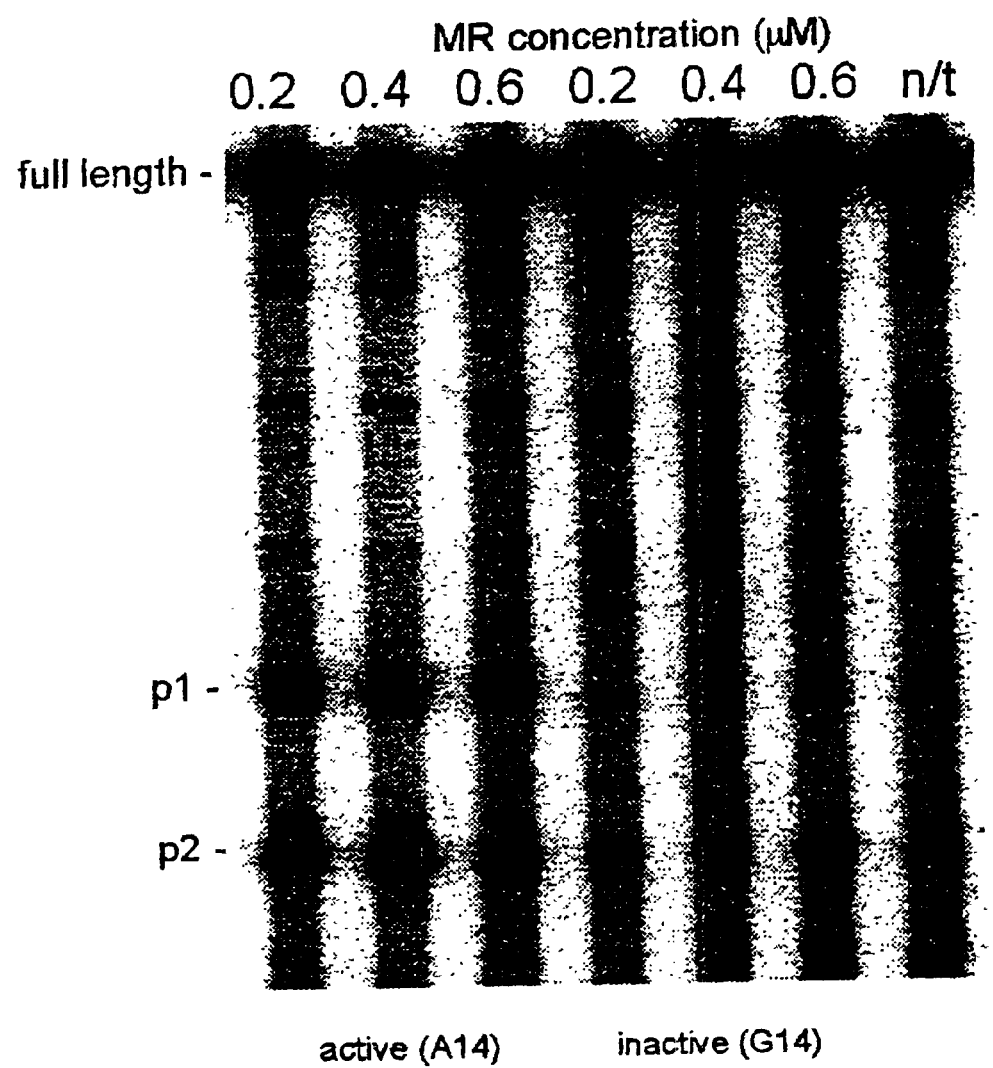

In a separate experiment a range of concentrations of MR9 were used, using a fixed amount (6.25 µL) of lipofectamine. In this experiment a mutant miniribozyme containing a A14 to G14 inactivating substitution (MR13) was used as a negative control molecule. Miniribozymes with this base substitution do not show any in vitro cleavage activity. FIG. 12 shows the results of the RPA. All three concentrations of active (MR9) miniribozyme show extensive cleavage of cellular PDGF RNA, with 0.4 µM being the most effective concentration. The analogous miniribozyme with the single base inactivating mutation (MR13) showed negligible increase in specific cleavage products as compared with the untreated cells (n/t).

CONCLUSION

The results here show that there is no implicit or necessary reduction of activity associated with the minimisation of helix III to a single Watson-Crick base pair. The activity of a miniribozyme is dependent on linker composition. Rate constants in excess of those observed for conventional hammerhead ribozymes can be achieved by appropriately engineered linker motifs. The composition of this linker region has been thoroughly assayed in this study by means of in vitro evolution. Three classes of linker design have been elucidated via in vitro selection using low $Mg^{2+}$ concentrations. The high activities displayed by some of these miniribozymes, and the transferability of these observations into different substrate backgrounds, has resulted in generalised designs for oligonucleotide reagents that retain high catalytic activity at physiological concentrations of $Mg^{2+}$ ion. Whilst the relative activities of miniribozymes and more conventional hammerheads will almost certainly vary with the length of helix 1, the superiority of the miniribozyme at a physiological concentration of $Mg^{2+}$, using helix lengths devised for optimum results on gene length substrates, suggests that miniribozymes offer a first choice design for in vivo studies.

Similar conclusions can be drawn from the results of the selection of 7-nucleotide (GNNNNNC) linker. There is a subset of sequences that appear to impart distinct kinetic advantages to the miniribozymes that possess them. It seems likely that many of the sequences although selected as RNA will also impart high cleavage activity upon miniribozymes which incorporate the analogous DNA sequences. It is possible to incorporate various modified nucleotides into miniribozymes of these designs, which may for example have the effect-of stabilising them against nuclease attack, without significant loss of cleavage activity. Finally, it has been demonstrated that miniribozymes of this design are able to specifically cleave mRNA within the cellular environment, the cleavage observed being due solely to the intrinsic cleavage activity posssessed by the miniribozyme.

Persons skilled in this art will appreciate that variations and modifications may be made to the invention as broadly described herein, other than those specifically described without departing from the spirit and scope of the invention. It is to be understood that this invention extends to include all such variations and modifications.

References

1. Williams, K. P. and Bartel, D. P. (1996) In Eckstein, F., and Lilley, D. M. J. (eds.), Catalytic RNA. Springer-Verlag, Berlin.
2. Pan, T., Long, D. M. and Uhlenbeck, O. C. (1993) In Gesteland, R. F., and Atkins, J. F. (eds.), The RNA World. Cold Spring Harbor Laboratory Press, New York.
3. Pyle, A. M. and Green, J. B. (1995) Curr. Opin. Struct. Biol., 5, 303–310.
4. Long, D. M. and Uhlenbeck, O. C. (1993) FASEB J., 7, 25–30.
5. Joyce, G. F. (1989) Nature, 338, 217–224.
6. Orgel, L. E. (1986) J. theor. Biol., 123, 127–149.
7. Scott, W. G. and Klug, A. (1996) Trends Biochem Sci, 21(6), 220–224.
8. Cowan, J. A. (1997) JBIC, 2, 168–176.
9. Yarus, M. (1993) FASEB J., 7, 31–39.
10. Pyle, A. M. (1993) Science, 261, 709–714.
11. Symons, R. H. (1992) Annu. Rev. Biochem., 61, 641–671.
12. Uhlenbeck, O. C. (1987) Nature, 328, 596–600.

13. Haseloff, J. and Gerlach, W. L. (1988) *Nature*, 334, 585–591.
14. Perriman, R., Delves, A. and Gerlach, W. L. (1992) *Gene*, 113, 157–163.
15. Shimayama, T., Nishikawa, S. and Taira, K. (1995) *Biochemistry*, 34, 3649–3654.
16. Zoumadakis, M. and Tabler, M. (1995) *Nucleic Acids Res.*, 23, 1192–1196.
17. Dahm, S. C. and Uhlenbeck, O. C. (1991) *Biochemistry*, 30, 9464–9469.
18. Laing, G. L., Gluick, T. C. and Draper, D. E. (1994) *J. Mol. Biol.*, 237, 577–587.
19. Bassi, G. S., Mollegaard, N.-E., von Kitzing, E. and Lilley, D. M. J. (1995) *Structural Biol.*, 2, 45–55.
20. Bassi, G. S., Murchie, A. I. H. and Lilley, D. M. J. (1996) *RNA*, 2(8), 756–768.
21. Bassi, G. S., Murchie, A. I. H., Walter, F., Clegg, R. M. and Lilley, D. M. J. (1997) *EMBO J*, 16(24), 7481–7489.
22. Scott, W. G., Murray, J. B., Arnold, J. R. P., Stoddard, B. L. and Klug, A. (1996) *Science*, 274(5295), 2065–2069.
23. Zhou, D. M., Zhang, L. H. and Taira, K. (1997) *Proc Natl Acad Sci USA*, 94(26), 14343–14348.
24. Pontius, B. W., Lott, W. B. and vonHippel, P. H. (1997) *Proc Natl Acad Sci USA*, 94(6), 2290–2294.
25. McCall, M. J., Hendry, P. and Jennings, P. A. (1992) *Proc. Natl. Acad. Sci. USA*, 89, 5710–5741.
26. Hendry, P., Moghaddam, M. J., McCall, M. J., Jennings, P. A., Ebel, S. and Brown, T. (1994) *Biochim. Biophys. Acta*, 1219, 405–412.
27. Hendry, P. and McCall, M. (1995) *Nucleic Acids Res.*, 23, 3922–3927.
28. Tuschl, T. and Eckstein, F. (1993) *Proc. Natl. Acad. Sci. USA*, 90, 6991–6994.
29. Pley, H. W., Flaherty, K. M. and McKay, D. B. (1994) *Nature*, 372, 68–74.
30. Scott W. G., Finch, J. T. and Klug, A. (1995) *Cell*, 81, 991–1002.
31. Hendry, P. and McCall, M. (1996) *Nucleic Acids Res*, 24(14), 2679–2684.
32. McCall, M. J., Hendry, P. and Lockett, T. J. (1997) In Turner, P. C. (ed.), Ribozyme Protocols. Humana Press Inc, 999 Riverview Dr, Ste 208, Totowa, N.J. 07512-1165, Vol. 74, pp. 151–159.
33. Flatman, P. W. (1991) *Annu. Rev. Physiol.*, 53, 259–271.
34. Freier, S. M., Kierzek, R., Jaeger, J. A., Sugimoto, N., Caruthers, M. H., Neilson, T. and Turner, D. H. (1986) *Proc. Natl. Acad. Sci. USA*, 83, 9373–9377.
35. Thomson, J. B., Sigurdsson, S. T., Zeuch, A. and Eckstein, F. (1996) *Nucleic Acids Res*, 24(22), 4401–4406.
36. Forster, A. C. and Symons, R. H. (1987) *Cell*, 49, 211–220.
37. Heus, H. A. and Pardi, A. (1991) *Science*, 253, 191–194.
38. Abramovitz, D. L. and Pyle, A. M. (1997) *J. Mol Biol*, 266(3), 493–506.
39. Jucker, F. M. and Pardi, A. (1995) *RNA*, 1, 219–222.
40. Murphy, F. L. and Cech, T. R. (1994) *J. Mol. Biol.*, 236, 49–63.
41. Uhlenbeck, O. C. (1990) *Nature*, 346, 613–614.
42. Butcher, S. E., Dieckmann, T. and Feigon, J. (1997) *J. Mol. Biol.*, 268, 348–358.
43. Murray, J. B., Terwey, D. P., Maloney, L., Karpeisky, A., Usman, N., Beigelman, L. and Scott, W. G. (1998) *Cell*, 92(5), 665–673.
44. Chartrand, P., Leclerc, F. and Cedergren, R. (1997) *RNA*, 3(7), 692–696.
45. Fu, D. J. and McLaughlin, L. W. (1992) *Biochemistry*, 31, 10941–10949.
46. Fu, D. J., Rajur, S. B. and McLaughlin, L. W. (1993) *Biochemistry*, 32, 10629–10637.
47. Grasby, J. A., Butler, P. J. G. and Gait, M. J. (1993) *Nucleic Acids Res.*, 21, 4444–4450.
48. Sioud, M. (1997) *Nucleic Acids Res*, 25(2), 333–338.
49. Sioud, M., Opstad, A., Hendry, P., Lockett, T. J., Jennings, P. A. and McCall, M. J. (1997) *Biochem Biophys Res Commun*, 231(2), 397–402.
50. Zillmann, M., Limauro, S. E. and Goodchild, J. (1997) *RNA*, 3(7), 734–747.
51. Jucker, F. M. and Pardi, A. (1995) *Biochemistry*, 34, 14416–14427.
52. Long, D. M. and Uhlenbeck, O. C. (1994) *Proc. Natl. Acad. Sci. USA*, 91, 6977–6981.
53. Hertel, K. J., Pardi, A., Uhlenbeck, O. C., Koizumi, M., Ohtsuka, E., Uesugi, S., Cedergren, R., Eckstein, F., Gerlach, W. L., Hodgson, R. and Symons, R. H. (1992) *Nucleic Acids Res.*, 20, 3252.
54. Kelly, J. L., Sanchez, A., Brown, G.S., Chesterman, C. N. and Seigh, M. J. (1993). *Journal of Cell Biology*, 121, 1153–1163.
55. Ausubel, F. M., Brent, R., Kingston, R. E., Moore, D. D., Seidman, J. G., Smith, J. A., Struhl, K. (editors), *Current Protocols in Molecular Biology*, Greene-Wiley Interscience 1993.

What is claimed is:

1. A miniribozyme of the formula IA or IB:

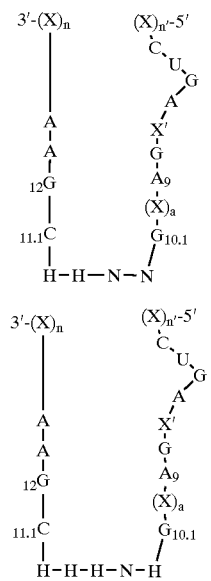

wherein each X represents a nucleotide which may be the same or different and may be substituted or modified in its sugar, base or phosphate; and wherein $G_{10.1}$ and $C_{11.1}$ each represent a nucleotide which may be substituted or modified in its sugar (which may be ribose or deoxyribose), base or phosphate;

wherein each of C, G, A and U represents a ribonucleotide which may be substituted or modified in its sugar, base or phosphate;

wherein each of $(X)_n$ and $(X)_{n-1}$-A and $(X)_{n'}$ represents an oligonucleotide having a pre-determined sequence which is capable of hybridizing with an RNA target sequence to be cleaved, such RNA target sequence not being present within the compound, and each of n and n' represents an integer which defines the number of nucleotides in the oligonucleotide;

wherein X' represents a ribonucleotide selected from C, G, A and U which may be substituted or modified in its sugar, base or phosphate;

wherein a defines the number of nucleotides in $(X)_a$ and may be 0 or 1 and if 0, the A located 5' of $(X)_n$ is bonded to the G located 3' of $(X)_{n'}$;

wherein each solid line represents a chemical linkage providing covalent bonds between the nucleotides located on either side thereof;

wherein each N represents a nucleotide selected from C, G, A and U/T which may be substituted or modified in its sugar (which may be ribose or deoxyribose), base or phosphate and wherein each H represents a nucleotide selected from C, A and U/T, which may be substituted or modified in its sugar (which may be ribose or deoxyribose), base or phosphate; with the proviso that the sequence 5'-NNHH-3' is not UUUU or TTTT, CUCC, MUU or GGCA.

2. A miniribozyme of claim 1, wherein in the formula IB the oligonucleotide 3'-$(X)_n$- is 3'-$(X)_{n-1}$-A-.

3. A miniribozyme of claim 1, wherein $(X)_a$ is absent.

4. A miniribozyme of claim 1, wherein the sum of n+n' is greater than 14.

5. A miniribozyme of claim 1, wherein the sequence 5'-NNHH-3' is a linker sequence selected from the following classes of linker sequences:

Class I: YRHH, wherein Y is C or U, R is G or A, and H is C, A or U;

Class II: DYHH, wherein D is G, A or U, Y is C or U, and H is C, A or U;

Class III: GHHA, wherein H is C, A or U; and

Class IV: WYHH, wherein W is A or U, Y is C or U, and H is C, A or U.

6. A miniribozyme of claim 5, wherein the linker sequence is selected from the sequences CGUU, UGUU and UAAC.

7. A miniribozyme of claim 5, wherein the linker sequence is a sequence of the class WYHH, wherein W is A or U, Y is C or U, and H is C, A or U.

8. A miniribozyme of claim 7, wherein the linker sequence is selected from the sequences ACCC, AUUU, UCCC, AUUC, AUUA, ACAC, AUAA and AUAC.

9. A miniribozyme of claim 7, wherein the linker sequence is the sequence UUHH, wherein H is C, A or U.

10. A miniribozyme of claim 9, wherein the linker sequence is selected from the sequences UUAC, UUCC, UUUC, UUUA, UUAA and UUAU.

11. A miniribozyme of claim 5, wherein the linker sequence is selected from the sequences GUAA and GAUA.

12. A miniribozyme of claim 1, wherein the sequence 5'-HNHHH-3' in the miniribozyme of formula IB is selected from the sequences UCCCA, UCCCC, UCCUA, AAUUU, UUAAA, UUUUA, UGUCC, UGUUA and CACCC.

13. A miniribozyme of claim 12, wherein the sequence 5'-HNHHH-3' in the miniribozyme of formula IB is selected from the sequences UCCCC, UGUCC and CACCC.

14. A miniribozyme of claim 1, wherein each nucleotide in the linker sequence 5'-NNHH-3' or the linker sequence 5'-HNHHH-3' is a deoxyribonucleotide.

15. A composition which comprises the miniribozyme of claim 1 in association with an acceptable carrier.

16. A composition which comprises the miniribozyme of claim 5 in association with an acceptable carrier.

17. An oligonucleotide transfer vector containing a nucleotide sequence which on transcription gives rise to the miniribozyme of claim 1 or claim 5.

18. A oligonucleotide transfer vector of claim 17, wherein the transfer vector is a bacterial plasmid, a bacteriophage DNA, a cosmid, or an eukaryotic viral DNA.

19. A oligonucleotide transfer vector of claim 17, wherein the oligonucleotide transfer vector is a plant DNA virus, a geminivirus or an infective phage particle.

20. A oligonucleotide transfer vector of claim 17, wherein the oligonucleotide transfer vector is packaged and contains the promoter sequences for RNA polymerase II or RNA polymerase III.

21. A host cell transformed in vitro by the transfer vector of claim 17.

22. A host cell of claim 21, wherein the host cell is a prokaryotic host cell or an eukaryotic host cell.

23. A prokaryotic host cell of claim 22, wherein the prokaryotic host cell is an *E. coli* host cell.

24. A eukaryotic host cell of claim 22, wherein the eukaryotic host cell is a monkey COS host cell, a Chinese hamster ovary host cell, a mammalian host cell or a plant host cell.

25. A method of cleaving a target mRNA in a host cell in vitro which comprises administering to the host cell an effective amount of the miniribozyme of claim 1 or claim 5, or a transfer vector which on transcription expresses the miniribozyme of claim 1 or claim 5.

26. A miniribozyme of claim 1 or claim 5 which further comprises an antisense nucleic acid which hybridizes with an RNA target sequence.

27. A miniribozyme of claim 1 or claim 5 which further comprises at least one additional non-naturally occurring oligonucleotide compound which comprises nucleotides whose sequence defines a conserved catalytic region and nucleotides whose sequence hybridizes with a predetermined target sequence.

28. A miniribozyme of claim 27, wherein the additional non-naturally occurring oligonucleotide compound is a hammerhead ribozyme, a miniribozyme, a hairpin ribozyme, a hepatitis delta ribozyme, an RNAase P ribozyme, a Group I intron, or a combination thereof.

29. A miniribozyme of claim 1 having the formula:

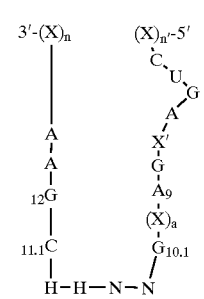

IA

30. A miniribozyme of claim 1 having the formula:

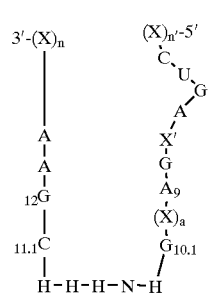

IB

* * * * *